(12) United States Patent
Larsen et al.

(10) Patent No.: US 7,304,033 B2
(45) Date of Patent: Dec. 4, 2007

(54) METHODS FOR PROTECTING ALLOGENEIC ISLET TRANSPLANT USING SOLUBLE CTLA4 MUTANT MOLECULES

(75) Inventors: Christian P. Larsen, Atlanta, GA (US); Thomas C. Pearson, Atlanta, GA (US); Andrew B. Adams, Atlanta, GA (US); Robert J. Peach, San Diego, CA (US); Peter S. Linsley, Seattle, WA (US); Joseph Roy Naemura, Bellevue, WA (US); Jurgen Bajorath, Bonn (DE)

(73) Assignee: Bristol-Myers Squibb Company, Princeton, NJ (US)

( * ) Notice: Subject to any disclaimer, the term of this patent is extended or adjusted under 35 U.S.C. 154(b) by 272 days.

(21) Appl. No.: 10/155,514

(22) Filed: May 23, 2002

(65) Prior Publication Data

US 2003/0022836 A1    Jan. 30, 2003

Related U.S. Application Data

(60) Provisional application No. 60/293,402, filed on May 23, 2001.

(51) Int. Cl.
*A61K 38/16*    (2006.01)
*C07K 14/00*    (2006.01)

(52) U.S. Cl. .................. 514/12; 424/134.1; 530/350; 530/387.3

(58) Field of Classification Search ............ 424/134.1, 424/377; 530/387.3
See application file for complete search history.

(56) References Cited

U.S. PATENT DOCUMENTS

| | | | |
|---|---|---|---|
| 4,399,216 A | 8/1983 | Axel et al. | |
| 5,434,131 A | 7/1995 | Linsley et al. | |
| 5,521,288 A | 5/1996 | Linsley et al. | |
| 5,580,756 A | 12/1996 | Linsley et al. | |
| 5,637,481 A | 6/1997 | Ledbetter et al. | |
| 5,770,197 A | 6/1998 | Linsley et al. | |
| 5,773,253 A | 6/1998 | Linsley et al. | |
| 5,844,095 A | 12/1998 | Linsley et al. | |
| 5,851,795 A | 12/1998 | Linsley et al. | |
| 5,883,223 A | 3/1999 | Gray | |
| 5,885,579 A | 3/1999 | Linsley et al. | |
| 5,885,796 A | 3/1999 | Linsley et al. | |
| 5,916,560 A | 6/1999 | Larsen et al. | |
| 5,958,403 A | 9/1999 | Strom et al. | |
| 5,968,510 A | 10/1999 | Linsley et al. | |
| 5,977,318 A | 11/1999 | Linsley et al. | |
| 5,993,800 A | 11/1999 | Linsley et al. | |
| 6,080,412 A | 6/2000 | Jordan et al. | |
| 6,090,914 A | 7/2000 | Linsley et al. | |
| 6,113,898 A | 9/2000 | Anderson et al. | |
| 6,132,992 A | 10/2000 | Ledbetter et al. | |
| 6,280,957 B1 | 8/2001 | Sayegh et al. | |
| 6,352,694 B1 | 3/2002 | June et al. | |
| 6,444,792 B1 | 9/2002 | Gray et al. | |
| 6,534,055 B1 | 3/2003 | June et al. | |
| 6,641,809 B1 | 11/2003 | Brady et al. | |
| 6,685,941 B1 | 2/2004 | Thompson et al. | |
| 6,719,972 B1 | 4/2004 | Gribben et al. | |
| 6,750,334 B1 | 6/2004 | Gray et al. | |
| 6,830,937 B1 | 12/2004 | Brady et al. | |
| 2001/0053361 A1 | 12/2001 | Thompson et al. | |
| 2002/0031510 A1 | 3/2002 | Larsen et al. | |
| 2002/0039577 A1 | 4/2002 | Todderud et al. | |
| 2002/0115214 A1 | 8/2002 | June et al. | |
| 2002/0182211 A1* | 12/2002 | Peach et al. ............. | 424/143.1 |
| 2003/0007968 A1 | 1/2003 | Adams et al. | |
| 2003/0083246 A1 | 5/2003 | Cohen et al. | |
| 2003/0099622 A1 | 5/2003 | Hering et al. | |
| 2003/0219863 A1 | 11/2003 | Peach et al. | |
| 2004/0014171 A1 | 1/2004 | Peach et al. | |
| 2004/0022787 A1 | 2/2004 | Cohen et al. | |
| 2004/0047890 A1* | 3/2004 | Weber et al. ................ | 424/423 |
| 2005/0214313 A1* | 9/2005 | Peach et al. ............. | 424/185.1 |

FOREIGN PATENT DOCUMENTS

| | | |
|---|---|---|
| EP | 0 613 944 A2 | 9/1994 |
| EP | 0 682 039 A1 | 11/1995 |
| WO | WO 90/05541 | 5/1990 |
| WO | WO 93/00431 | 1/1993 |
| WO | WO 93/19767 | 10/1993 |
| WO | WO94/01547 | 1/1994 |
| WO | WO 94/28912 | 12/1994 |
| WO | WO 94/29436 | 12/1994 |

(Continued)

OTHER PUBLICATIONS

Merriam-Webster Online Dictionary: entry for "Regimen" (Mar. 8, 2005).*

(Continued)

*Primary Examiner*—Phillip Gambel
*Assistant Examiner*—Ilia Ouspenski
(74) *Attorney, Agent, or Firm*—Mandel & Adriano

(57) ABSTRACT

The present invention is a method of inhibiting islet cell transplant rejection, particularly to treat diabetes, such as type-1 and type-2 diabetes, by administering to a subject an effective amount of a soluble CTLA4 mutant molecule. One example of a soluble CTLA4 mutant molecule is L104EA29YIg.

32 Claims, 24 Drawing Sheets

FOREIGN PATENT DOCUMENTS

| | | |
|---|---|---|
| WO | WO95/06481 | 3/1995 |
| WO | WO95/28957 | 11/1995 |
| WO | WO02/02638 A2 | 12/1995 |
| WO | WO95/33770 | 12/1995 |
| WO | WO 95/33823 | 12/1995 |
| WO | WO 95/34320 | 12/1995 |
| WO | WO 96/14865 | 5/1996 |
| WO | WO 96/23071 | 8/1996 |
| WO | WO 97/28267 | 8/1997 |
| WO | WO 98/31820 | 7/1998 |
| WO | WO 98/33513 | 8/1998 |
| WO | WO 98/56417 | 12/1998 |
| WO | WO99/39726 | 8/1999 |
| WO | WO99/39727 | 8/1999 |
| WO | WO 00/23115 | 4/2000 |
| WO | WO 01/54732 A1 | 8/2001 |
| WO | WO 01/90122 A2 | 11/2001 |
| WO | WO 01/92337 | 12/2001 |
| WO | WO02/083187 | 10/2002 |
| WO | WO 2004/058800 | 7/2004 |
| WO | WO 2004/058944 | 7/2004 |
| WO | WO 2005/016266 | 2/2005 |

OTHER PUBLICATIONS

Shapiro et al., New England Journal of Medicine, 2000, 343: 230-238.*

Komelli et al., 2000, J. Cell. Biol., 151: 863-878.*

ElAntak et al., 2005, J. Biol. Chem., 280: 36802-36808.*

Kuhnt et al., Enzyme Microb. Technol., 1997, 21 : 405-412 (reference provided by Applicant).*

Abrams, Judith R. et al., "CTLA4Ig-mediated blockade of T-cell costimulation in patients with psoriasis vulgaris," The Journal of Clinical Investigation, 1999, 103:1243-52 (Exhibit 13).

Azuma, Miyuki et al., "B70 antigen is a second ligand for CTLA-4 and CD28," Nature, 1993, 366:76-9 (Exhibit 14).

Broach, James R., "Construction of High Copy Yeast Vectors Using 2-μm Circle Sequences," Methods of Enzymology, 1983, 101:307-25 (Exhibit 15).

Byrn, Randal A. et al., "Characterization of In Vitro Inhibition of Human Immunodeficiency Virus by Purified Recombinant CD4," Journal of Virology, 1989, 63:4370-5 (Exhibit 16).

Clarke, Louise et al., "Selection Procedure for Isolation of Centromere DNAs from Saccharomyces cerevisiae," Methods of Enzymology, 1983, 101:300-7 (Exhibit 17).

Cohen, Stanley N. et al., "Nonchromosomal Antibiotic Resistance in Bacteria: Genetic Transformation of Escherichia coli by R-Factor DNA," Proc. Natl. Acad. Sci. USA, 1972, 69:2110-4 (Exhibit 18).

Dash, Bret et al., "Deletion of a single N-linked glycosylation site from the transmembrane envelope protein of human immunodeficiency virus type 1 stops cleavage and transport of gp160 preventing env-mediated fusion," Journal of General Virology, 1994, 75:1389-97 (Exhibit 19).

European Mycophenolate Mofetil Cooperative Study Group, "Placebo-controlled study of mycophenolate mofetil combined with cyclosporine and corticosteroids for prevention of acute rejection," The Lancet, 1995, 345:1321-5 (Exhibit 20).

Falk, Kirsten et al., "Both Human and Mouse Cells Expressing H-2K$^b$ and Ovalbumin Process the Same Peptide, SIINFEKL," Cellular Immunology, 1993, 150:447-52 (Exhibit 21).

Fiers, W. et al., "Complete nucleotide sequence of SV40 DNA," Nature, 1978, 273:113-20 (Exhibit 22).

Freeman, Gordon J. et al., "B7, A New Member of the Ig Superfamily with Unique Expression on Activated and Neoplastic B Cells," The Journal of Immunology, 1989, 143:2714-22 (Exhibit 23).

Freeman, Gordon J. et al., "Cloning of B7-2: A CTLA-4 Counter-Receptor that Costimulates Human T Cell Proliferation," Science, 1993, 262:909-11 (Exhibit 24).

Fujikawa, Kiyomi et al., "Short Communications: Nuclear Localization and Transforming Activity of Human Papillomavirus Type 16 E7-β-Galactosidase Fusion Protein: Characterization of the Nuclear Localization Sequence," Virology, 1994, 204:789-93 (Exhibit 25).

Gérard, C. et al., "Production and Characterization of Polyclonal Antibodies Recognizing the Intracytoplasmic Third Loop of the 5-Hyrdroxytryptamine$_{Ia}$ Receptor," Neuroscience, 1994, 62:721-39 (Exhibit 26).

Goeddel, David V. et al., "Synthesis of human fibroblast interferon by E. coli," Nucleic Acids Research, 1980, 8:4057-74 (Exhibit 27).

Greene, JoAnne L. et al., "Covalent Dimerization of CD28/CTLA-4 and Oligomerization of CD80/CD86 Regulate T Cell Costimulatory Interactions," Journal of Biological Chemistry, 1996, 271:26762-71 (Exhibit 28).

Hansen, John A. et al., "Monoclonal Antibodies Identifying a Novel T-Cell Antigen and Ia Antigens of Human Lymphocytes," Immunogenetics, 1980, 10:247-60 (Exhibit 29).

Hess B. et al., "Cooperation of Glycolytic Enzymes," Adv. Enzyme Reg., 1968, 7:149-67 (Exhibit 30).

Hitzeman, Ronald A. et al., "Isolation and Characterization of the Yeast 3-Phosphoglycerokinase Gene (PGK) by and Immunological Screening Technique," The Journal of Biological Chemistry, 1980, 255:12073-80 (Exhibit 31).

Holland, Michael J. et al., "Isolation and Identification of Yeast Messenger Ribonucleic Acids Coding for Enolase, Glyceraldehyde-3-phosphate Dehydrogenase, and Phosphoglycerate Kinase," Biochemistry, 1978, 17:4900-7 (Exhibit 32).

Ikeda, Toshio et al., "Isolation of a cDNA encoding the chicken p508/p97 (Lyt-10) transcription factor," Gene, 1994, 138:193-6 (Exhibit 33).

Johnsson, Bo et al., "Immobilization of Proteins to a Carboxymethyldextran-Modified Gold Surface for Biospecific Interaction Analysis in Surface Plamon Resonance Sensors," Analytical Biochemistry, 1991, 198:268-77 (Exhibit 34).

Jones, Nancy H. et al., "Isolation of complementary DNA clones encoding the human lymphocyte glycoprotein T1/Leu-1," Nature, 1986, 323:346-9 (Exhibit 35).

Kahan, Barry D., "Cyclosporine," The New England Journal of Medicine, 1989, 321:1725-38 (Exhibit 36).

Karin, Michael and Robert I. Richards, "Huyman metallothionein genes—primary structure of the metallothionein-II gene and a related processed gene," Nature, 1982, 299:797-802 (Exhibit 37).

Kenyon, Norma S. et al., "Long-term survival and function of the intrahepatic islet allografts in rhesus monkeys treated with humanized anti-CD154," Proc. Natl. Acad. Sci. USA, 1999, 96:8132-7 (Exhibit 38).

Khilko, Sergei N. et al., "Direct Detection of Major Histocompatibility Complex Class I Binding to Antigenic Peptides Using Surface Plasmon Resonance," Journal of Biological Chemistry, 1993, 268:15425-34 (Exhibit 39).

Kirk, Allan D. et al., "Treatment with humanized monoclonal antibody against CD154 prevents acute renal allograft rejection in nonhuman primates," Nature Medicine, 1999, 5:686-93 (Exhibit 40).

Knapp, L. A. et al., "A high frequency of Mamu-A *01 in the rhesus macaque detected by polymerase chain reaction with sequence-specific primers and direct sequencing," Tissue Antigens, 1997, 50:657-61 (Exhibit 41).

Kolhekar, Aparna S. et al., "Peptidylglycine α-Hydroxylating Monooxygenase: Active Site Residues, Disulfide Linkages, and a Two-Domain Model of the Catalytic Core," Biochemistry, 1997, 36:10901-9 (Exhibit 42).

Lasky, Laurence A. et al., "Neutralization of the AIDS Retrovirus by Antibodies to a Recombinant Envelope Glycoprotein," Science, 1986, 233:209-12 (Exhibit 43).

Levisetti, Matteo G. et al., "Immunosuppressive Effects of Human CTLA4Ig in a Non-Human Primate Model of Allogeneic Pancreatic Islet Transplantation," The Journal of Immunology, 1997, 159:5187-91 (Exhibit 44).

Li, Yongsheng et al., "Blocking both signal 1 and signal 2 of T-cell activation prevents apoptosis of alloreactive T cells and induction of peripheral allograft tolerance," Nature Medicine, 1999, 5:1298-1302 (Exhibit 45).

Linetsky, Elina et al., "Improved Human Islet Isolation Using a New Enzyme Blend, Liberase," *Diabetes*, 1997, 46:1120-3 (Exhibit 46).

Linsley, Peter S. et al., "Coexpression and Functional Cooperation of CTLA-4 and CD28 on Activated T Lymphocytes," *Journal of Experimental Medicine*, 1992, 176:1595-604 (Exhibit 47).

Linsley, Peter S. et al., "Human B7-1 (CD80) and B7-2 (CD86) Bind with Similar Avidities but Distinct Kinetics to CD28 and CTLA-4 Receptors," *Immunity*, 1994, 1:793-801 (Exhibit 48).

Linsley, Peter S. et al., "Binding Stoichiometry of the Cytotoxic T Lymphocyte-associated Molecule-4 (CTLA-4)," *Journal of Biological Chemistry*, 1995, 270:15417-24 (Exhibit 49).

Lobashevsky, A. et al., "Identification of DRB alleles in rhesus monkeys using polymerase chain reaction-sequence-specific primers (PCR-SSP) amplification," *Tissue Antigens*, 1999, 54:254-63 (Exhibit 50).

Maini, Ravinder et al., "Infliximab (chimeric anti-tumour necrosis factor α monoclonal antibody) versus placebo in rheumatoid arthritis patients receiving concomitant methotrexate: a randomized phase III trial," *The Lancet*, 1999, 354:1932-9 (Exhibit 51).

Malik Najma et al., "Molecular Cloning, Sequence Analysis, and Functional Expression of a Novel Growth Regulator, Oncostatin M," *Molecular and Cellular Biology*, 1989, 9:2847-53 (Exhibit 52).

Martin, Paul J. et al., "Preincubation of Donor Bone Marrow Cells with a Combination of Murine Monoclonal Anti-T-Cell Antibodies Without Complement Does Not Prevent Graft-Versus-Host Disease After Allogeneic Marrow Transplantation," *Journal of Clinical Immunology*, 1984, 4:18-22 (Exhibit 53).

Mathiesen, T. et al., "Prolonged survival and vascularization of xenografted human glioblastoma cells in the central nervous system of Cyclosporine A treated rats," *Cancer Letters*, 1989, 44:151-6 (Exhibit 54).

Metzler, William J. et al., "Solution structure of human CTLA-4 and delineation of a CD80/CD86 binding site conserved in CD28," *Nature Structural Biology*, 1997, 4:527-31 (Exhibit 55).

Moreland, Larry W. et al., "Etanercept Therapy in Rheumatoid Arthritis: A Randomized, Controlled Trial," *Annals of Internal Medicine*, 1999, 130:478-86 (Exhibit 56).

O'Shannessy, Daniel J. et al., "Determination of Rate and Equilibrium Binding Constants for Macromolecular Interactions Using Surface Plasmon Resonance: Use of Nonlinear Least Squares Analysis Methods," *Analytical Biochemistry*, 1993, 212:457-68 (Exhibit 57).

Oaks, Martin K. et al., "A Native Soluble Form of CTLA-4," *Cellular Immunology*, 2000, 201:144-53 (Exhibit 58).

Peach, Robert J. et al., "Complementarity Determining Region 1 (CDR-1)- and CDR3-analogous Regions in CTLA-4 and CD28 Determine the Binding to B7-1," *Journal of Experimental Medicine*, 1994, 180:2049-58 (Exhibit 59).

Ricordi, Camillo et al., "Automated Method of Isolation of Human Pancreatic Islets," *Diabetes*, 1988, 37:413-20 (Exhibit 60).

Ryan, Edmond A. et al., "Clinical Outcomes and Insulin Secretion After Islet Transplantation with the Edmonton Protocol," *Diabetes*, 2001, 50:710-9 (Exhibit 61).

Shapiro, A. M. James et al., "Islet Transplantation in Seven Patients with Type 1 Diabetes Mellitus Using a Glucocorticoid-Free Immunosuppressive Regimen," *European Journal of Immunology*, 2000, 343:230-8 (Exhibit 62).

Shimatake, Hiroyuki and Martin Rosenberg, "Purified λ regulatory protein cll positively activates promoters for lysogenic development," *Nature*, 1981, 292:128-32 (Exhibit 63).

Smith, Douglas H. et al., "Blocking of HIV-1 Infectivity by a Soluble, Secreted Form of the CD4 Antigen," *Science*, 1987, 238:1704-7 (Exhibit 64).

Stinchcomb, D. T. et al., "Isolation and characterization of a yeast chromosomal replicator," *Nature*, 1979, 282:39-43 (Exhibit 65).

Thomas, Judith M. et al., "Successful Reversal of Streptozotocin-Induced Diabetes with Stable Allogeneic Islet Function in a Preclinical Model of Type 1 Diabetes," *Diabetes*, 2001, 50:1227-36 (Exhibit 66).

Toyama, Reiko and Hiroto Okayama, "Human chorionic gonadotropin α and human cytomegalovirus promoters are extremely active in the fission yeast Schizosaccharomyces pombe," *FEBS Letters*, 1990, 268:217-21 (Exhibit 67).

Tschumper, Gary and John Carbon, "Sequence of a yeast DNA fragment containing a chromosomal replicator and the *TRP1* gene," *Gene*, 1980, 10:157-65 (Exhibit 68).

U.S. Multicenter FK506 Liver Study Group, "A Comparison of Tacrolimus (FK506) and Cyclosporine for Immunosuppression in Liver Trasnplantation," *The New England Journal of Medicine*, 1994, 331:1110-5 (Exhibit 69).

Urlaub, Gail et al., "Effect of Gamma Rays at the Dihydrofolate Reductase Locus: Deletions and Inversions," *Somatic Cell and Molecular Genetics*, 1986, 12:555-66 (Exhibit 70).

Weinblatt, Michael E. et al., "A Trial of Etanercept, A Recombinant Tumor Necrosis Factor Receptor: Fc Fusion Protein, in Patients with Rheumatoid Arthritis Receiving Methotrexate," *New England Journal of Medicine*, 1999, 340:253-9 (Exhibit 71).

Yokochi, Takashi et al, "B Lymphoblast Antigen (BB-1) Expressed on Epstein-Barr Virus-Activated B Cell Blasts, B Lymphoblastoid Cell Lines, And Burkitt's Lymphomas," *Journal of Immunology*, 1982, 128:823-7 (Exhibit 72).

Zeng, Yijun et al., "The effect of prednisone on pancreatic islet autografts in dogs," *Surgery*, 1993, 113:98-102 (Exhibit 73).

de Mattos, Angelo M. et al., "Nephrotoxicity of Immunosuppressive Drugs: Long-Term Consequences and Challenges for the Future" *American Journal of Kidney Diseases*, 2000, 35:333-46 (Exhibit 169).

Montgomery, Sean P. et al., "Toxicity of Rapamycin, Tacrolimus, and Daclixumab in the Non-Human Primate," *American Journal of Transplantation*, 2001, P157-III, p. 438 (Exhibit 170).

Ranuncoli, Alessandra et al., "Islet Cell Transplantation: In Vivo and In Vitro Functional Assessment of Nonhuman Primate Pancreatic Islets" *Cell Transplantation*, 2000, 9:409-14 (Exhibit 171).

Ricordi, Camillo et al., "Islet Isolation Assessment in Man and Large Animals" *Acta Diabetologica Latina*, 1990, 27:185-95 (Exhibit 172).

Watkins, David I., "The Evolution of Major Histocompatibility Class I Genes in Primates" *Critical Reviews in Immunology*, 1995, 15:1-29 (Exhibit 173).

Bluestone, Jeffrey A., "New Perspectives of CD28-B7-Mediated T Cell Costimulation," *Immunity*, 1995, 2:555-9 (Exhibit 222).

Bluestone, J. A., "Costimulation and its role in organ transplantation," *Clin. Transplantation*, 1996, 10:104-9 (Exhibit 223).

Chen, Fang-An et al., "Human Antibody Response in Human Peripheral Blood Leukocyte/Severe Combined Immunodeficient Chimeric Model is Dependent on B and T Cell Costimulation via CD40/CD40 Ligand," *Journal of Immunology*, 1995, 155:2833-40 (Exhibit 224).

Durie, Fiona H. et al., "Prevention of Collagen-Induced Arthritis with an Antibody to gp39, the Ligand for CD40," *Science*, 1993, 261:1328-30 (Exhibit 225).

Durie, Fiona H. et al., "Antibody to the Ligand of CD40, gp39, Blocks the Occurrence of the Acute and Chronic Forms of Graft-vs-Host Disease," *Journal of Clinical Investigation*, 1994, 94:1333-8 (Exhibit 226).

Griggs, Nathan et al., "Contribution of CD28/CTLA4/B7 and gp39/CD40 Costimulation Pathways in Clonal Expansion and Functional Acquisition of Self Reactive T Cells," *Journal of Cellular Biochemistry*, 1995, Supplement, p. 141, C2-427 (Exhibit 227).

Jenkins, Marc K. et al., "CD28 Delivers a Costimulatory Signal Involved in Antigen-Specific IL-2 Production by Human T Cells," *Journal of Immunology*, 1991, 147:2461-6 (Exhibit 228).

Lenschow, Deborah J. et al., "Inhibition of Transplant Rejection Following Treatment with Anti-B7-2 and Anti-B7-1 Antibodies," *Transplantation*, 1995, 60:1171-8 (Exhibit 229).

Rossini, Aldo A. et al., "Induction of Immunological Tolerance to Islet Allografts," *Cell Transplantation*, 1996, 5:49-52 (Exhibit 230).

Roy, Meenakshi et al., "Studies on the interdependence of gp39 and B7 expression and function during antigen-specific immune response," *European Journal of Immunology*, 1995, 25:596-603 (Exhibit 231).

Schaub, M. et al., "Synergistic effect of CD40L/CD40 and CD28/B7 Blockade in murine EAE," *Journal of Allergy and Clinical Immunology*, 1997, 99:5206, Abstract 843 (Exhibit 232).

Tang, Aimin et al., "Suppression of Murine Allergic Contact Dermatitis by CTLA4Ig: Tolerance Induction of Th2 Responses Requires Additional Blockade of CD40-Ligand," *Journal of Immunology*, 1996, 157:117-25 (Exhibit 233).

Linsley, Peter S. et al., "CTLA-4 Is a Second Receptor for the B Cell Activation Antigen B7" *The Journal of Experimental Medicine*, 1991, 174:561-9 (Exhibit 76).

Gimmi, Claude D. et al., "Human T-cell clonal anergy is induced by antigen presentation in th absence of B7 costimulation" *Proc. Natl. Acad. Sci. USA*, 1993, 90:6586-90 (Exhibit 77).

Ronchese, Franca et al., "Mice Transgenic for a Soluble Form of Murine CTLA-4 Show Enhanced Expansion of Antigen-specific CD4+T Cells and Defective Antibody Production In Vivo" *The Journal of Experimental Medicine*, 1994, 179:809-17 (Exhibit 78).

Griggs, Nathan D. et al., "The Relative Contribution of the CD28 and gp39 Costimulatory Pathways in the Clonal Expansion and Pathogenic Acquisition of Self-reactive T Cells" *The Journal of Experimental Medicine*, 1996, 183:801-10 (Exhibit 79).

Verwilghen, Jo et al., "Expression of Functional B7 and CTLA4 on Rheumatoid Synovial T Cells" *The Journal of Immunology*, 1994, 153:1378-85 (Exhibit 80).

Blazar, Bruce R. et al., "In Vivo Blockade of CD28/CTLA4: B7/BB1 Interaction With CTLA4-lg Reduces Lethal Murine Graft-Versus-Host Disease Across the Major Histocompatibility Complex Barrier in Mice" *Blood*, 1994, 83:3815-25 (Exhibit 81).

Finck, Barbara K., et al., "Treatment of Murine Lupus with CTLA4Ig" *Science*, 1994, 265:1225-7 (Exhibit 82).

Perrin, Peter J. et al., "Role of B7:CD28/CTLA-4 in the Induction of Chronic Relapsing Experimental Allergic Encephalomyelitis" *The Journal of Immunology*, 1995, 154:1481-90 (Exhibit 83).

Pearson, Thomas C. et al., "Transplantation Tolerance Induced By CTLA4-Ig" *Transplantation*, 1994, 57:1701-6 (Exhibit 84).

Baliga, Prabhakar et al., "CTLA4Ig Prolongs Allograft Survival While Suppressing Cell-Mediat d Immunity" *Transplantation*, 1994, 58:1082-90 (Exhibit 85).

Tepper, M. A. et al., "Tolerance Induction by Soluble CTLA4 in a Mouse Skin Transplant Model" *Transplantation Proceedings*, 1994, 26:3151-4 (Exhibit 86).

Perico, Norberto et al., "Toward novel antirejection strategies: In vivo immunosuppressive properties of CTLA4Ig" *Kidney International*, 1995, 47:241-6 (Exhibit 87).

Finck, B. K. et al., "Effects of CTLA4Ig in Murine Lupus" *Arthritis and Rheumatism*, 1994, 37:S222 (Exhibit 88).

Nishikawa, Kazuhiro et al., "Effect of CTLA-4 chimeric protein on rat autoimmune anti-glomerular basement membrane glomerulonephritis" *Eur. J. Immunol*, 1994, 24:1249-54 (Exhibit 89).

Wallace, Philip M. et al., "CTLA4Ig Treatment Ameliorates the Lethality of Murine Graft-Versus-Host Disease Across Major Histocompatibility Complex Barriers" *Transplantation*, 1994, 58:602-10 (Exhibit 90).

Damle, Nitin K. et al., "Costimulation of T Lymphocytes with Integrin Ligands Intercellular Adhesion Molecule-1 or Vascular Cell Adhesion Molecule-1 Induces Functional Expression of CTLA-4, a Second Receptor for B7" *The Journal of Immunology*, 1994, 152:2686-97 (Exhibit 91).

Milich, David R. et al., "Soluble CTLA-4 Can Suppress Autoantibody Production and Elicit Long Term Unresponsiveness in a Novel Transgenic Model," *The Journal of Immunology*, 1994, 153:429-35 (Exhibit 92).

Webb, Louise M. C. et al., "Prevention and amelioration of collagen-induced arthritis by blockade of the CD28 co-stimulatory pathway: requirement for both B7-1 and B7-2" *European Journal of Immunology*, 1996, 26:2320-8 (Exhibit 93).

Van Oosterhout, A. J. M. et al., "Murine CTLA4-IgG Treatment Inhibits Airway Eosinophilia and Hyperresponsiveness and Attenuates IgE Upregulation in a Murine Model of Allergic Asthma," *American Journal of Respiratory Cell and Molecular Biology*, 1997, 17:386-92 (Exhibit 94).

Ibrahim, Sherif et al., "CTLA4Ig Inhibits Alloantibody Responses to Repeated Blood Transfusions," *Blood*, 1996, 88:4594-600 (Exhibit 95).

Lenschow, Deborah J. et al., "Differential Effects of Anti-B7-1 and Anti-B7-2 Monoclonal Antibody Treatment on the Development of Diabetes in the Nonobese Diabetic Mouse," *J. Exp. Med.*, 1995, 181:1145-55 (Exhibit 96).

Lenschow, Deborah J. et al., "Long-Term Survival of Xenogeneic Pancreatic Islet Grafts Induced by CTLA4Ig," *Science*, 1992, 257:789-92 (Exhibit 97).

Sayegh, Mohamed H., "Finally, CTLA4lg graduates to the clinic," *The Journal of Clinical Investigation*, 1999, 103:1223-5 (Exhibit 98).

Wolfe, Frederick, "The epidemiology of drug treatment failure in rheumatoid arthritis," *Baillière's Clinical Rheumatology*, 1995, 9:619-32 (Exhibit 99).

Hochberg, Marc C. and Timothy D. Spector, "Epidemiology of Rheumatoid Arthritis: Update," *Epidemiologic Reviews*, 1990, 12:247-52 (Exhibit 100).

Spector, Tim D., "Rheumatoid Arthritis," *Rheumatic Disease Clinics of North America*, 1990, 16:513-37 (Exhibit 101).

Liu, Ming Fei, et al., "The Presence of Costimulatory Molecules CD86 and CD28 in Rheumatoid Arthritis Synovium," *Arthritis &Rheumatism*, 1996, 39:110-4 (Exhibit 102).

Sfikakis, Petros P. and Charles S. Via, "Expression of CD28, CTLA4, CD80, and CD86 Molecules in Patients with Autoimmune Rheumatic Diseases: Implications for Immunotherapy," *Clinical Immunology and Immunopathology*, 1997, 83: 195-8 (Exhibit 103).

Sayegh, Mohamed H., et al., "CD28-B7 Blockade after Alloantigenic Challenge In Vivo Inhibits Th1 Cytokines but Spares Th2," *J. Exp. Med.*, 1995, 181: 1869-74 (Exhibit 104).

Racusen, Lorraine C., et al., "The Banff 97 working classification of renal allograft pathology," *Kidney International*, 1999, 55: 713-23 (Exhibit 105).

Parkin, David, et al., "Treatment of multiple sclerosis with interferon β: an appraisal of cost-effectiveness and quality of life," *J. Neurol. Neurosurg. Psychiatry*, 2000, 68:144-9 (Exhibit 106).

Nortvedt, Monica W. et al., "Quality of life in multiple sclerosis: Measuring the disease effects more broadly," *Neurology*, 1999, 53:1098-1103 (Exhibit 107).

Liao, Hua-Xin and Barton F. Haynes, "Role of Adhesion Molecules in the Pathogenesis of Rheumatoid Arthritis," *Rheumatic Disease Clinics of North America*, 1995, 21:715-40 (Exhibit 108).

Thomas, Ranjeny and Christopher Quinn, "Functional Differentiation of Dendritic Cells in Rheumatoid Arthritis: Role of CD86 in the Synovium," *The Journal of Immunology*, 1996, 156:3074-86 (Exhibit 109).

Verhoeven, A. C. et al., "Combination Therapy in Rheumatoid Arthritis: Update Systematic Review," *British Journal of Rheumatology*, 1998, 37:612-9 (Exhibit 110).

Schiff, Michael, "Emerging Treatments for Rheumatoid Arthritis" *Am. J. Med.*, 1997, 102: 11S-15S (Exhibit 111).

Balsa, A, et al., "Differential Expression of the Costimulatory Molecules B7.1 (CD80) and B7.2 (CD86) in Rheumatoid Synovial Tissue," *British Journal of Rheumatology*, 1996, 35:33-7 (Exhibit 112).

Ranheim, Erik A. and Thomas J. Kipps, "Elevated Expression of CD80 (B7/BB1) and Other Accessory Molecules on Synovial Fluid Mononuclear Cell Subsets in Rheumatoid Arthritis," *Arthritis &Rheumatism*, 1994, 37:1637-46 (Exhibit 113).

Becker, J.C., Abstract and Presentation of "A multi-center, randomized, double-blind, placebo controlled study to evaluate the safety and preliminary clinical activity of multiple doses of CTLA4Ig and LEA29Y administration intravenously to subjects with rheumatoid arthritis," presented at American College of Rheumatology Conference: "2001 Innovative Therapies in Autoimmune Diseases," San Francisco, California, Mar. 8, 2001 (Exhibit 114).

Aruffo, S., Presentation of "Approaches to Immune Regulation" at BIO 2000 in Boston, Massachusetts, Mar. 27, 2000 (Exhibit 115).

Abrams, Judith R. et al., "Blockade of T Lymphocyte Costimulation with Cytotoxic T Lymphocyte-associated Antigen 4-Immunogloblin (CTLA4Ig) Reverse the Cellular Pathology of Psoriatic plaques, Including the Activation of Keratinocytes, Dendritic Cells, and Endothelial Cells," *Journal of Experimental Medicine*, 2000, 192:681-93 (Exhibit 116).

Srinivas, N. R. et al., "Pharmacokinetics and Pharmacodynamics of CTLA4Ig (BMS-188667), a Novel Immunosuppressive Agent, in Monkeys following Multiple Doses," *Journal of Pharmaceutical Sciences*, 1996, 85:1-4 (Exhibit 117).

Gandhi, Rajesh B. et al., Abstract and Presentation of "Physical and Chemical Characterization of BMS-224818, A Recombinant Fusion Protein," in San Francisco, California, *PharmSci Supplement*, Nov. 18, 1998, 1:S-535 (Exhibit 118).

Flesher, Alan R., Presentation of Transgenic Production, A Comparative Study at Bio 99 in Seattle, Washington, Apr. 15, 1999 (Exhibit 119).

Greve, Kimberly F., "Capillary electrophoretic examination of underivatized oligosaccharide mixtures released from immunoglobulin G anitbodies and CTLA4Ig fusion protein," *Journal of Chromatography*, 1996, 749:237-245 (Exhibit 120).

Srinivas, Nuggehally R. et al., "Assessment of Dose Proportionality, Absolute Bioavailability, and Immunogenicity Response of CTLA4Ig (BMS-188667), a Novel Immunosuppressive Agent, Following Subcutaneous and Intravenous Administration to Rats," *Pharmaceutical Research*, 1997, 14:911-6 (Exhibit 121).

Weiner, R. et al., Abstract and Presentation of "Validation and PK Application of a Double Antibody Sandwich Enzyme Immunoassay For the Quantitation of Human CTLA4Ig Fusion Protein (BMS-188667) in Mouse Serum," Nov. 6-10, 1994 (Exhibit 122).

Weiner Russell S. et al., "A sensitive enzyme immunoassay for the quantitation of human CTLA4Ig fusion protein in mouse serum: pharmacokinetic application to optimizing cell line selection," *Journal of Pharmaceutical and Biomedical Analysis*, 1997, 15:571-579 (Exhibit 123).

Warner, G. L. et al., Abstract and Presentation of "Bioactivity of BMS-188667 (CTLA4Ig) in Cynomolgus Monkeys," in Seattle, Washington, Mar. 16-22, 1995 (Exhibit 124).

Weiner, Russell S., Abstract and Presentation of "Industrial Perspectives of Primary Analytical Tools for Macromolecules—Principles and Applications with Examples" Mar. 1, 2000 (Exhibit 125).

Weiner, Russell et al., Abstract and Presentation of "Validation of an Enzyme Immunoassay for the Quantitation of Human CTLA4Ig Fusion Protein in Human Serum," in Miami, Florida, Nov. 1995 (Exhibit 126).

Weiner, Russell, Abstract and Presentation of "Automation and Validation of An EIA For Quantitation of Human CTLA4Ig in Monkey Serum," in Miami, Florida, Nov. 1995 (Exhibit 127).

Knoerzer, Debbie Barney et al., "Collagen-induced Arthritis in the BB Rat: Prevention of Disease by Treatment with CTLA-4Ig," *Journal of Clinical Investigation*, 1995, 96:987-93 (Exhibit 128).

Larsen, Christian P. et al., Abstract of "Prolongation of Renal Allograft Survival by a Chimeric Anti-Human CD40 Monoclonal Antibody in Nonhuman Primates," in *Transplantation*, 2000, 69:S123, #45 (Exhibit 129).

Larsen, Christian P. et al., Presentation of "Prolongation of Renal Allograft Survival With Blockade of the CD28 Pathway Using A Novel Mutant CTLA4-Ig Fusion Protein In Non-Human Primates" at th American Society of Transplantation Meeting in Chicago, Illinois, Mar. 3-4, 2000 (Exhibit 130).

Larsen, Christian P., Presentation of "Manipulation of Costimulatory Pathways: Targeting CD80 and CD86" at the XVII congress of the Transplantation Society in Rome, Italy, Aug. 27-Sep. 1, 2000 (Exhibit 131).

Larsen, Christian P., Presentation of "Costimulation blockade: progress toward clinical application" at Canadian Society of Transplantation Annual Scientific meeting in Mont Tremblant, Quebec, Canada, Mar. 3-4, 2000 (Exhibit 132).

Larsen, Christian P. Presentation of "Costimulation blockade: Progress toward clinical application" at the American Society of Transplantation Meeting in Las Croabas, Puerto Rico, Jan. 13-17, 2000 (Exhibit 133).

Hathcock, Karen S. et al., "Identification of an Alternative CTLA-4 Ligand Costimulatory for T Cell Activation," *Science*, 1993, 262:905-911 (Exhibit 134).

Sfikakis, Peter P. et al., "CD28 Expression On T Cell Subsets In Vivo and CD28-Mediated T Cell Response In Vitro in Patients with Rheumatoid Arthritis," *Arthritis & Rheumatism*, 1995, 38:649-54 (Exhibit 135).

Lakkis, Fadi G. et al., "Blocking the CD28-B7 T Cell Costimulation Pathway Induces Long T rm Cardiac Allograft Acceptance in the Absence of IL-4," *The Journal of Immunology*, 1997, 158:2443-8 (Exhibit 136).

Pearson, Thomas C. et al., "Analysis of the B7 Costimulatory Pathway in Allograft Rejection," *Transplantation*, 1997, 63:1463-9 (Exhibit 137).

Alexander, Diane Z. et al., "Analysis of a Functional Role for Chimerism in CTLA4-Ig Plus Bon Marrow-Treaded Cardiac Allograft Recipients," *Transplantation*, 1994, 91:416-8 (Exhibit 138).

Larsen, Christian P. et al., "CD40-gp39 Interactions Play a Critical Role During Allograft Rej ction," *Transplantation*, 1996, 61:4-9 (Exhibit 139).

Pearson, Thomas C. et al., "CTLA4-Ig Plus Bone Marrow Induces Long-Term Allograft Survival and Donor-Specific Unresponsiveness in the Murine Model," *Transplantation*, 1996, 61:997-1004 (Exhibit 140).

Weber, C. J. et al., "CTLA4-Ig Prolongs Survival of Microencapsulated Rabbit Islet Xenografts in Spontaneously Diabetic Nod Mice," *Transplantation Proceedings*, 1996, 28:821-3 (Exhibit 141).

Alexander, D. Z. et al., "Analysis of effector mechanisms in murine cardiac allograft rejection," *Transplant Immunology*, 1996, 4:46-8 (Exhibit 142).

Larsen, Christian P. et al., "Long-term acceptance of skin and cardiac allografts after blocking CD40 and CD28 pathways," *Nature*, 1996, 381:434-8 (Exhibit 143).

Elwood, Eric T. et al., "Microchimerism and rejection in clinical transplantation," The Lancet, 1997, 349:1358-60 (Exhibit 144).

Larsen, Christian P. and Thomas C. Pearson, "The CD40 pathway in allograft rejection, acc ptance, and tolerance," Current Opinion in Immunology, 1997, 9:641-7 (Exhibit 145).

Konieczny, Bogumila T. et al., "IFN-γ Critical for Long-Term Allograft Survival Induced by Blocking the CD28 and CD40 Ligand T Cell Constimulation Pathways," The Journal of Immunology, 1998, 160:2059-64 (Exhibit 146).

Elwood, Eric T. et al., "Prolonged Accpetance of Concordant and Discordant Xenografts with Combined CD40 and CD28 Pathway Blockade," Transplantation, 1998, 65:1422-8 (Exhibit 147).

Niimi, Masanori et al., "The Role of the CD40 Pathway in Alloantigen-Induced Hyporesponsiveness In Vivo," The Journal of Immunology, 1998, 161:5331-7 (Exhibit 148).

Whitmire, Jason K. et al., "CD40-CD40 Ligand Costimulation is Required for Generating Antiviral CD4 T Cell Responses But Is Dispensable for CD8 T Cell Responses," Journal of Immunology, 1999, 163:3194-201 (Exhibit 149).

Bingaman, Adam W. et al., "Vigorous Allograft Rejection in the Absence of Danger," The Journal of Immunology, 2000, 164:3065-71 (Exhibit 150).

Bingaman, Adam W. et al., "Transplantation of the Bone Marrow Microenvironment Leads to Hematopoietic Chimerism Without Cytoreductive Conditioning," Transplantation, 2000, 69:2491-6 (Exhibit 151).

Durham, Megan M. et al., "Cutting Edge: Administration of Anti-CD40 Ligand and Donor Bone Marrow Leads to Hemopoietic Chimerism and Donor-Specific Tolerance Without Cytoreductive Conditioning," *The Journal of Immunology*, 2000, 165:1-4 (Exhibit 152).

Williams, Matthew A. et al., "Genetic Characterization of Strain Differences in the Ability to Mediate CD40/CD28-Independent Rejection of Skin Allografts," *The Journal of Immunology*, 2000, 165:6849-57 (Exhibit 153).

Bingaman, Adam W. et al., "The role of CD40L in T cell-dependent nitric oxide production by murine macrophages," *Transplant Immunology*, 2000, 8:195-202 (Exhibit 154).

Adams, Andrew B. et al., "Costimulation Blockade, Busulfan, and Bone Marrow Promote Titratable Macrochimerism, Induce Transplantation Tolerance, and Correct Genetic Hemoglobinopathies with Minimal Myelosuppression," *Journal of Immunology*, 2001, 167:1103-11 (Exhibit 155).

Meng, L. et al., "Blockade of the CD40 Pathway Fails to Prevent CD8 T Cell-Mediated Intestinal Allograft Rejection," *Transplantation Proceedings*, 2001, 33:418-20 (Exhibit 156).

Guo, Zhong et al., "CD8 T Cell-Mediated Rejection of Intestinal Allografts is Resistant to Inhibition of the CD40/CD154 Costimulatory Pathway," *Transplantation*, 2001, 71:1351-4 (Exhibit 157).

Ha, Jongwon et al., "Aggressive skin allograft rejection in CD28/ mice independent of the CD40/CD40L costimulatory pathway," *Transplant Immunology*,2001, 9:13-7 (Exhibit 158).

Bingaman, Adam W. et al., "Analysis of the CD40 and CD28 Pathways on Alloimmune Responses by CD4+ T Cells In Vivo," *Transplantation*, 2001, 72:1286-92 (Exhibit 159).

Adams, Andrew B. et al., "Calcineurin Inhibitor—Free CD28 Blockade-Based Protocol Protects Allogeneic Islets in Nonhuman Primates," *Diabetes*, 2002, 51:265-70 (Exhibit 160).

Whelchel, J. D. et al. "Evolving Strategies in Immunosuppressive Therapy: The Emory Experience," *Clinical Transplants*, 1996, J. Michael Cecka, Ph.D. and Paul I. Terasaki, Ph.D., (eds.), 249-55 (Exhibit 161).

Ritchie, Shannon C. et al., "Regulation of Immunostimulatory Function and B7 Molecule Expression on Murine Dendritic Cells," *Journal of Cellular Biochemistry*, 1995, 21A:C1-215 (Exhibit 162).

Alexander, Diane Z. et al., "Analysis of the Mechanisms of CTLA4-Ig Plus Bone Marrow Induced Tramsplantation Tolerance," *Journal of Cellular Biochemistry*, 1995, 21A:C1-301 (Exhibit 163).

Alexander, Diane Z. et al., "CTLA4-lg-Induced Transplantation Tolerance: Analysis of Donor Cell Chimerism," *Surgical Forum*, 1994, 45:402-4 (Exhibit 164).

Pearson, Thomas C. et al., "CTLA4-Ig + Bone Marrow Induces Transplantation Tolerance in the Murine Model," *Journal of Cellular Biochemistry*, 1995, 21A:C1-327 (Exhibit 165).

Lakkis, Fadi G. et al., "CTLA4Ig Induces Longterm Cardiac Allograft Survival in the Absence of Interleukin-4," *Journal of the American Society of Nephrology*, 1996, 7:1887 (Exhibit 166).

Linsley, Peter S. et al., "Immunosuppression in Vivo by a Soluble Form of the CTLA-4 T Cell Activation Molecule," *Science*, 1992, 257:792-795 (Exhibit 201).

Morton, Phillip A. et al., "Differential Effects of CTLA-4 Substitutions on the Binding of Human CD80 (B7-1) and CD86 (B7-2)," *Journal of Immunology*, 1996, 156:1047-1054 (Exhibit 202).

Sun, Hong et al., "Prevention of Chronic Rejection in Mouse Aortic Allografts by Combined Treatment with CTLA4-Ig and Anti-CD40 Ligand Monocional Antibody," *Transplantation*, 1997, 64:1838-56 (Exhibit 203).

Souza, D. et al., "Synergistic Inhibition of Established Collagen Induced Arthritis (CIA) Through Dual Inhibition of ICAM-1 and CD40L Pathways," *Arthritis and Rheumatism*, 1999, 42:S60 (Exhibit 204).

Blazar, Bruce R. et al., "Coblockade of the LFA1:ICAM and CD28/CTLA4:B7 Pathways Is a Highly Effective Means of Preventing Acute Lethal Graft-Versus-Host Disease Induced by Fully Major Histocompatibility Complex-Disparate Donor Grafts," *Blood*, 1995, 85:2607-18 (Exhibit 205).

Alegre, Maria-Luisa et al., "Immunomodulation of Transplant Rejection Using Monoclonal Antibodies and Soluble Receptors," *Digestive Diseases and Sciences*, 1995, 40:58-64 (Exhibit 206).

Murakami, Masaaki et al., "Identification and characterization of an alternative cytotoxic T lymphocyte-associated protein 4 binding molecule on B cells," *Proceedings of the National Academy of Sciences USA*, 1996, 93:7838-7842 (Exhibit 207).

Peach, Robert J. et al., "Both Extracellular Immnunoglobin-like Domains of CD80 Contain Residues Critical for Binding T Cell Surface Receptros CTLA-4 and CD28," *Journal of Biological Chemistry*, 1995, 270:21181-21187 (Exhibit 208).

Fargeas, Christine et al., "Identification of Residues in the V Domain of CD80 (B7-1) Implicated in Functional Interactions with CD28 and CTLA4," *Journal of Experimental Medicine*, 1995, 182:667-675 (Exhibit 209).

Steurer, Wolfgang et al., "Ex Vivo Coating of Islet Cell Allografts with Murin CTLA4/Fc Promotes Graft Tolerance," *Journal of Immunology*, 1995, 155:1165-1174 (Exhibit 210).

Guo, Yong et al., "Mutational Analysis and an Alternatively Spliced Product of B7 Defines Its CD28/CTLA4-binding Site on Immunoglobulin C-like Domain," *Journal of Experimental Medicine*, 1995, 181:1345-1355 (Exhibit 211).

Peach, Robert J. and Peter S. Linsley, "CTLA4Ig: A Novel Immunoglobulin Chimera with Immunosuppressive Properties," *Methods*, 1995, 8:116-123 (Exhibit 212).

Rattis, Frédérique-Marie et al., "Expression and function of B7-1 (CD80) and B7-2 (CD86) on human epidermal Langerhans cells," *European Journal of Immunology*, 1996, 26:449-453 (Exhibit 213).

Najafian, Nader and Mohamed H. Sayegh, "CTLA4-Ig: a novel immunosuppressive agent," *Exp. Opin. Invest. Drugs*, 2000, 9:2147-2157 (Exhibit 214).

Tan, Patrick et al., "Induction of Alloantigen-specific Hyporesponsiveness in Human T Lymphocytes by Blocking Interaction of CD28 with Its Natural Ligand B7/BB1," *Journal of Experimental Medicine*, 1993, 177:165-173 (Exhibit 215).

Turka, Laurence A. et al., "T-cell activation by the CD28 ligand B7 is required for cardiac allograft rejection in vivo," *Proceedings of the National Academy of Sciences USA*, 1992, 89:11102-11105 (Exhibit 216).

Schartz, R., "Constimulation of T Lymphocytes: The Role of CD28, CTLA-4, and B7/BB1 in Interleukin-2 Production and Immunotherapy," *Cell*, 1992, 71:1085-1088. (Exhibit 217).

\* cited by examiner

```
ONCOSTATIN M SIGNAL PEPTIDE
-25                        -20
M   G   V   L   L   T   Q   R   T   L   L   S   L   V   L
ATG GGT GTA CTG CTC ACA CAG AGG ACG CTG CTC AGT CTG GTC CTT    45

-10                                     -1  +1
A   L   L   F   P   S   M   A   S   M | A   M   H   V   A
GCA CTC CTG TTT CCA AGC ATG GCG AGC ATG GCA ATG CAC GTG GCC    90

+10                                 +20
Q   P   A   V   V   L   A   S   S   R   G   I   A   S   F
CAG CCT GCT GTG GTA CTG GCC AGC AGC CGA GGC ATC GCC AGC TTT    135

+30
V   C   E   Y   A   S   P   G   K   A   T   E   V   R   V
GTG TGT GAG TAT GCA TCT CCA GGC AAA GCC ACT GAG GTC CGG GTG    180

+40                                 +50
T   V   L   R   Q   A   D   S   Q   V   T   E   V   C   A
ACA GTG CTT CGG CAG GCT GAC AGC CAG GTG ACT GAA GTC TGT GCG    225

+60
A   T   Y   M   M   G   N   E   L   T   F   L   D   D   S
GCA ACC TAC ATG ATG GGG AAT GAG TTG ACC TTC CTA GAT GAT TCC    270

+70                                 +80
I   C   T   G   T   S   S   G   N   Q   V   N   L   T   I
ATC TGC ACG GGC ACC TCC AGT GGA AAT CAA GTG AAC CTC ACT ATC    315

+90
Q   G   L   R   A   M   D   T   G   L   Y   I   C   K   V
CAA GGA CTG AGG GCC ATG GAC ACG GGA CTC TAC ATC TGC AAG GTG    360

GLYCOSYLATION SITE
                +100                                +110
E   L   M   Y   P   P   P   Y   Y   L   G   I   G   N   G
GAG CTC ATG TAC CCA CCG CCA TAC TAC CTG GGC ATA GGC AAC GGA    405

+120
T   Q   I   Y   V   I   D   P   E   P   C   P   D   S   D
ACC CAG ATT TAT GTA ATT GAT CCA GAA CCG TGC CCA GAT TCT GAC    450

+130
F   L   L   W   I   L   A   A   V   S   S   G   L   F   F
TTC CTC CTC TGG ATC CTT GCA GCA GTT AGT TCG GGG TTG TTT TTT    495

+140                                +150
Y   S   F   L   L   T   A   V   S   L   S   K   M   L   K
TAT AGC TTT CTC CTC ACA GCT GTT TCT TTG AGC AAA ATG CTA AAG    540

+160
K   R   S   P   L   T   T   G   V   Y   V   K   M   P   P
AAA AGA AGC CCT CTT ACA ACA GGG GTC TAT GTG AAA ATG CCC CCA    585

+170                                +180
T   E   P   E   C   E   K   Q   F   Q   P   Y   F   I   P
ACA GAG CCA GAA TGT GAA AAG CAA TTT CAG CCT TAT TTT ATT CCC    630

+187
I   N
ATC AAT                                                        636
```

FIG. 1

| | |
|---|---|
| ATGGGTGTACTGCTCACACAGAGGACGCTGCTCAGTCTGGTCCTTGCACTCCTGTTTCCA | -19 |
| M~~G~~V~~L~~L~~T~~Q~~R~~T~~L~~L~~S~~L~~V~~L~~A~~L~~L~~F~~P~~ | -7 |
| AGCATGGCGAGCATGGCAATGCACGTGGCCCAGCCTGCTGTGGTACTGGCCAGCAGCCGA | +42 |
| S~~M~~A~~S~~M~~A~~M~~H~~V~~A~~Q~~P~~A~~V~~V~~L~~A~~S~~S~~R~~ | +14 |
| +1 | |
| GGCATCGCTAGCTTTGTGTGTGAGTATGCATCTCCAGGCAAAGCCACTGAGGTCCGGGTG | +102 |
| G~~I~~A~~S~~F~~V~~C~~E~~Y~~A~~S~~P~~G~~K~~A~~T~~E~~V~~R~~V~~ | +34 |
| ACAGTGCTTCGGCAGGCTGACAGCCAGGTGACTGAAGTCTGTGCGGCAACCTACATGATG | +162 |
| T~~V~~L~~R~~Q~~A~~D~~S~~Q~~V~~T~~E~~V~~C~~A~~A~~T~~Y~~M~~M~~ | +54 |
| GGGAATGAGTTGACCTTCCTAGATGATTCCATCTGCACGGGCACCTCCAGTGGAAATCAA | +222 |
| G~~N~~E~~L~~T~~F~~L~~D~~D~~S~~I~~C~~T~~G~~T~~S~~S~~G~~N~~Q~~ | +74 |
| GTGAACCTCACTATCCAAGGACTGAGGGCCATGGACACGGGACTCTACATCTGCAAGGTG | +282 |
| V~~N~~L~~T~~I~~Q~~G~~L~~R~~A~~M~~D~~T~~G~~L~~Y~~I~~C~~K~~V~~ | +94 |
| GAGCTCATGTACCCACCGCCATACTACCTGGGCATAGGCAACGGAACCCAGATTTATGTA | +342 |
| E~~L~~M~~Y~~P~~P~~P~~Y~~Y~~L~~G~~I~~G~~N~~G~~T~~Q~~I~~Y~~V~~ | +114 |
| ATTGATCCAGAACCGTGCCCAGATTCTGATCAGGAGCCCAAATCTTCTGACAAAACTCAC | +402 |
| I~~D~~P~~E~~P~~C~~P~~D~~S~~D~~Q~~E~~P~~K~~S~~S~~D~~K~~T~~H~~ | +134 |
| ACATCCCCACCGTCCCCAGCACCTGAACTCCTGGGGGGATCGTCAGTCTTCCTCTTCCCC | +462 |
| T~~S~~P~~P~~S~~P~~A~~P~~E~~L~~L~~G~~G~~S~~S~~V~~F~~L~~F~~P~~ | +154 |
| CCAAAACCCAAGGACACCCTCATGATCTCCCGGACCCCTGAGGTCACATGCGTGGTGGTG | +522 |
| P~~K~~P~~K~~D~~T~~L~~M~~I~~S~~R~~T~~P~~E~~V~~T~~C~~V~~V~~V~~ | +174 |
| GACGTGAGCCACGAAGACCCTGAGGTCAAGTTCAACTGGTACGTGGACGGCGTGGAGGTG | +582 |
| D~~V~~S~~H~~E~~D~~P~~E~~V~~K~~F~~N~~W~~Y~~V~~D~~G~~V~~E~~V~~ | +194 |
| CATAATGCCAAGACAAAGCCGCGGGAGGAGCAGTACAACAGCACGTACCGGGTGGTCAGC | +642 |
| H~~N~~A~~K~~T~~K~~P~~R~~E~~E~~Q~~Y~~N~~S~~T~~Y~~R~~V~~V~~S~~ | +214 |
| GTCCTCACCGTCCTGCACCAGGACTGGCTGAATGGCAAGGAGTACAAGTGCAAGGTCTCC | +702 |
| V~~L~~T~~V~~L~~H~~Q~~D~~W~~L~~N~~G~~K~~E~~Y~~K~~C~~K~~V~~S~~ | +234 |
| AACAAAGCCCTCCCAGCCCCCATCGAGAAAACCATCTCCAAAGCCAAAGGGCAGCCCCGA | +762 |
| N~~K~~A~~L~~P~~A~~P~~I~~E~~K~~T~~I~~S~~K~~A~~K~~G~~Q~~P~~R~~ | +254 |
| GAACCACAGGTGTACACCCTGCCCCCATCCCGGGATGAGCTGACCAAGAACCAGGTCAGC | +822 |
| E~~P~~Q~~V~~Y~~T~~L~~P~~P~~S~~R~~D~~E~~L~~T~~K~~N~~Q~~V~~S~~ | +274 |
| CTGACCTGCCTGGTCAAAGGCTTCTATCCCAGCGACATCGCCGTGGAGTGGGAGAGCAAT | +882 |
| L~~T~~C~~L~~V~~K~~G~~F~~Y~~P~~S~~D~~I~~A~~V~~E~~W~~E~~S~~N~~ | +294 |
| GGGCAGCCGGAGAACAACTACAAGACCACGCCTCCCGTGCTGGACTCCGACGGCTCCTTC | +942 |
| G~~Q~~P~~E~~N~~N~~Y~~K~~T~~T~~P~~P~~V~~L~~D~~S~~D~~G~~S~~F~~ | +314 |
| TTCCTCTACAGCAAGCTCACCGTGGACAAGAGCAGGTGGCAGCAGGGGAACGTCTTCTCA | +1002 |
| F~~L~~Y~~S~~K~~L~~T~~V~~D~~K~~S~~R~~W~~Q~~Q~~G~~N~~V~~F~~S~~ | +334 |
| TGCTCCGTGATGCATGAGGCTCTGCACAACCACTACACGCAGAAGAGCCTCTCCCTGTCT | +1062 |
| C~~S~~V~~M~~H~~E~~A~~L~~H~~N~~H~~Y~~T~~Q~~K~~S~~L~~S~~L~~S~~ | +354 |
| CCGGGTAAATGA | |
| P~~G~~K~~* | |

FIG. 2

| | |
|---|---|
| ATGGGTGTACTGCTCACACAGAGGACGCTGCTCAGTCTGGTCCTTGCACTCCTGTTTCCA | -19 |
| M~~G~~V~~L~~L~~T~~Q~~R~~T~~L~~L~~S~~L~~V~~L~~A~~L~~L~~F~~P~~ | -7 |
| AGCATGGCGAGCATGGCAATGCACGTGGCCCAGCCTGCTGTGGTACTGGCCAGCAGCCGA | +42 |
| S~~M~~A~~S~~M~~A~~M~~H~~V~~A~~Q~~P~~A~~V~~V~~L~~A~~S~~S~~R~~ | +14 |
| +1 | |
| GGCATCGCTAGCTTTGTGTGTGAGTATGCATCTCCAGGCAAATATACTGAGGTCCGGGTG | +102 |
| G~~I~~A~~S~~F~~V~~C~~E~~Y~~A~~S~~P~~G~~K~~Y~~T~~E~~V~~R~~V~~ | +34 |
| ACAGTGCTTCGGCAGGCTGACAGCCAGGTGACTGAAGTCTGTGCGGCAACCTACATGATG | +162 |
| T~~V~~L~~R~~Q~~A~~D~~S~~Q~~V~~T~~E~~V~~C~~A~~A~~T~~Y~~M~~M~~ | +54 |
| GGGAATGAGTTGACCTTCCTAGATGATTCCATCTGCACGGGCACCTCCAGTGGAAATCAA | +222 |
| G~~N~~E~~L~~T~~F~~L~~D~~D~~S~~I~~C~~T~~G~~T~~S~~S~~G~~N~~Q~~ | +74 |
| GTGAACCTCACTATCCAAGGACTGAGGGCCATGGACACGGGACTCTACATCTGCAAGGTG | +282 |
| V~~N~~L~~T~~I~~Q~~G~~L~~R~~A~~M~~D~~T~~G~~L~~Y~~I~~C~~K~~V~~ | +94 |
| GAGCTCATGTACCCACCGCCATACTACGAGGGCATAGGCAACGGAACCCAGATTTATGTA | +342 |
| E~~L~~M~~Y~~P~~P~~P~~Y~~Y~~E~~G~~I~~G~~N~~G~~T~~Q~~I~~Y~~V~~ | +114 |
| ATTGATCCAGAACCGTGCCCAGATTCTGATCAGGAGCCCAAATCTTCTGACAAAACTCAC | +402 |
| I~~D~~P~~E~~P~~C~~P~~D~~S~~D~~Q~~E~~P~~K~~S~~S~~D~~K~~T~~H~~ | +134 |
| ACATCCCCACCGTCCCCAGCACCTGAACTCCTGGGGGGATCGTCAGTCTTCCTCTTCCCC | +462 |
| T~~S~~P~~P~~S~~P~~A~~P~~E~~L~~L~~G~~G~~S~~S~~V~~F~~L~~F~~P~~ | +154 |
| CCAAAACCCAAGGACACCCTCATGATCTCCCGGACCCCTGAGGTCACATGCGTGGTGGTG | +522 |
| P~~K~~P~~K~~D~~T~~L~~M~~I~~S~~R~~T~~P~~E~~V~~T~~C~~V~~V~~V~~ | +174 |
| GACGTGAGCCACGAAGACCCTGAGGTCAAGTTCAACTGGTACGTGGACGGCGTGGAGGTG | +582 |
| D~~V~~S~~H~~E~~D~~P~~E~~V~~K~~F~~N~~W~~Y~~V~~D~~G~~V~~E~~V~~ | +194 |
| CATAATGCCAAGACAAAGCCGCGGGAGGAGCAGTACAACAGCACGTACCGTGTGGTCAGC | +642 |
| H~~N~~A~~K~~T~~K~~P~~R~~E~~E~~Q~~Y~~N~~S~~T~~Y~~R~~V~~V~~S~~ | +214 |
| GTCCTCACCGTCCTGCACCAGGACTGGCTGAATGGCAAGGAGTACAAGTGCAAGGTCTCC | +702 |
| V~~L~~T~~V~~L~~H~~Q~~D~~W~~L~~N~~G~~K~~E~~Y~~K~~C~~K~~V~~S~~ | +234 |
| AACAAAGCCCTCCCAGCCCCCATCGAGAAAACCATCTCCAAAGCCAAAGGGCAGCCCCGA | +762 |
| N~~K~~A~~L~~P~~A~~P~~I~~E~~K~~T~~I~~S~~K~~A~~K~~G~~Q~~P~~R~~ | +254 |
| GAACCACAGGTGTACACCCTGCCCCCATCCCGGGATGAGCTGACCAAGAACCAGGTCAGC | +822 |
| E~~P~~Q~~V~~Y~~T~~L~~P~~P~~S~~R~~D~~E~~L~~T~~K~~N~~Q~~V~~S~~ | +274 |
| CTGACCTGCCTGGTCAAAGGCTTCTATCCCAGCGACATCGCCGTGGAGTGGGAGAGCAAT | +882 |
| L~~T~~C~~L~~V~~K~~G~~F~~Y~~P~~S~~D~~I~~A~~V~~E~~W~~E~~S~~N~~ | +294 |
| GGGCAGCCGGAGAACAACTACAAGACCACGCCTCCCGTGCTGGACTCCGACGGCTCCTTC | +942 |
| G~~Q~~P~~E~~N~~N~~Y~~K~~T~~T~~P~~P~~V~~L~~D~~S~~D~~G~~S~~F~~ | +314 |
| TTCCTCTACAGCAAGCTCACCGTGGACAAGAGCAGGTGGCAGCAGGGGAACGTCTTCTCA | +1002 |
| F~~L~~Y~~S~~K~~L~~T~~V~~D~~K~~S~~R~~W~~Q~~Q~~G~~N~~V~~F~~S~~ | +334 |
| TGCTCCGTGATGCATGAGGCTCTGCACAACCACTACACGCAGAAGAGCCTCTCCCTGTCT | +1062 |
| C~~S~~V~~M~~H~~E~~A~~L~~H~~N~~H~~Y~~T~~Q~~K~~S~~L~~S~~L~~S~~ | +354 |
| CCGGGTAAATGA | |
| P~~G~~K~~* | |

FIG. 3

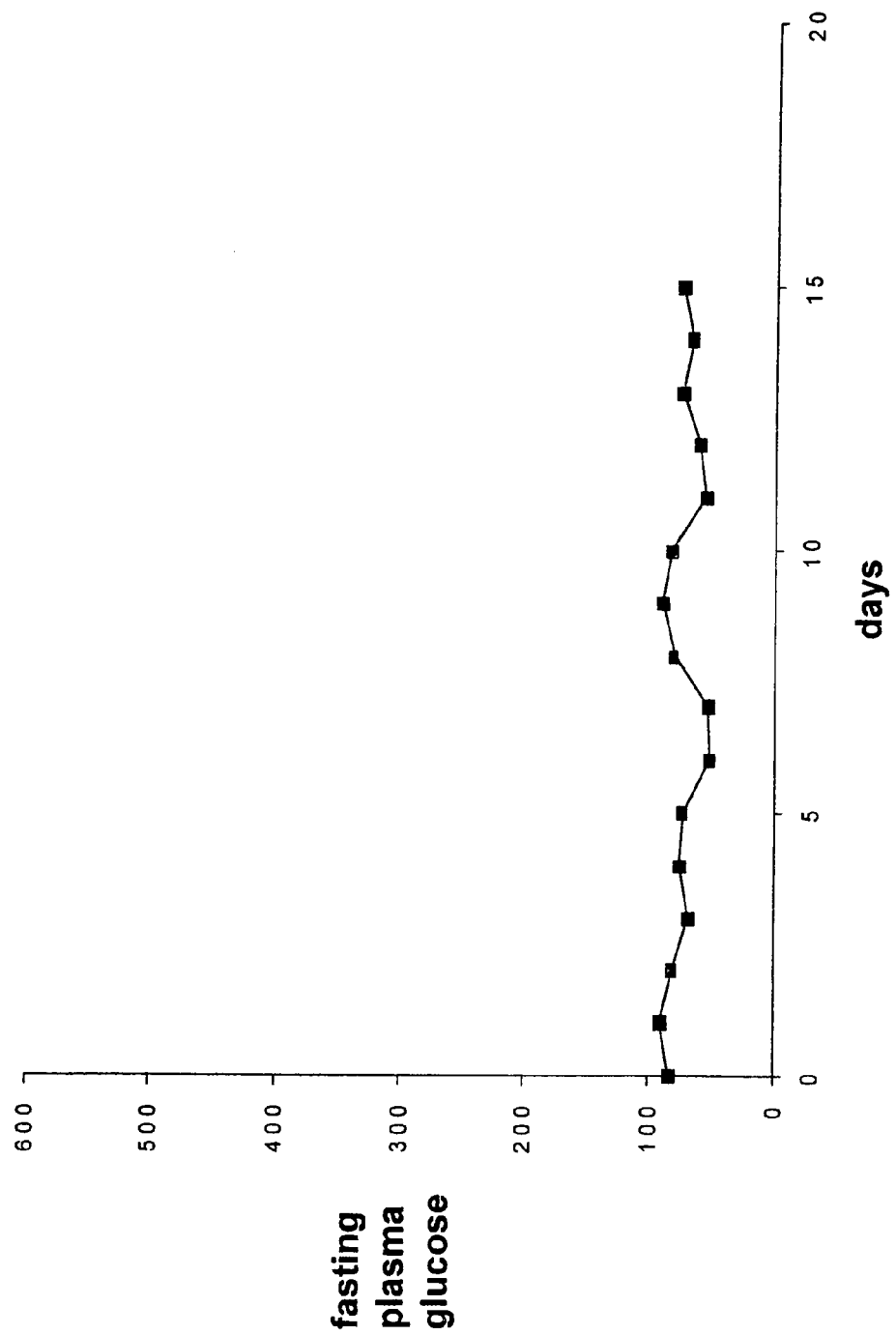

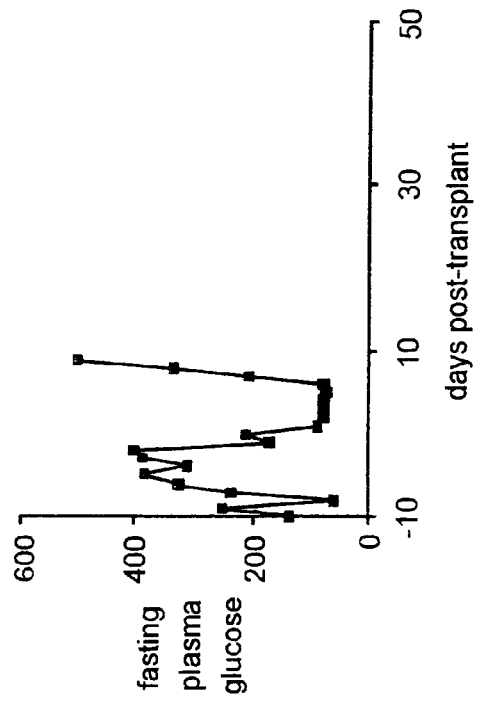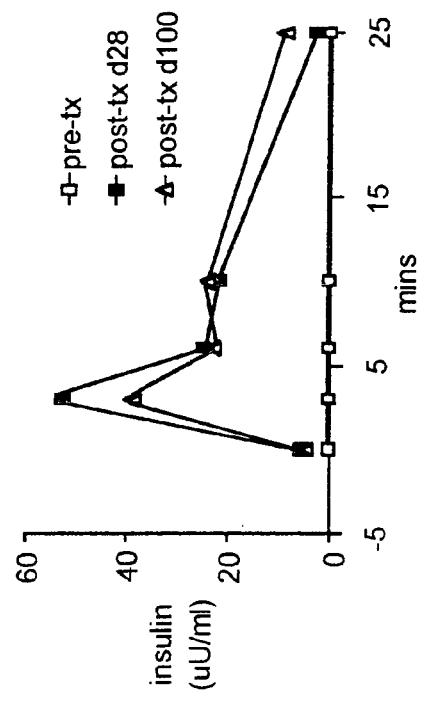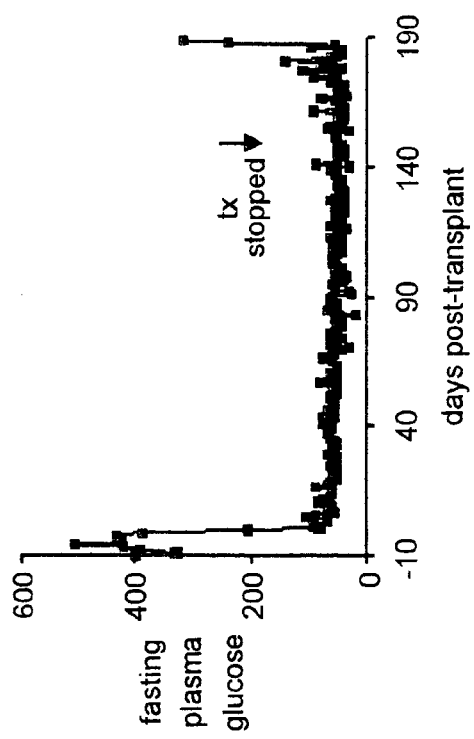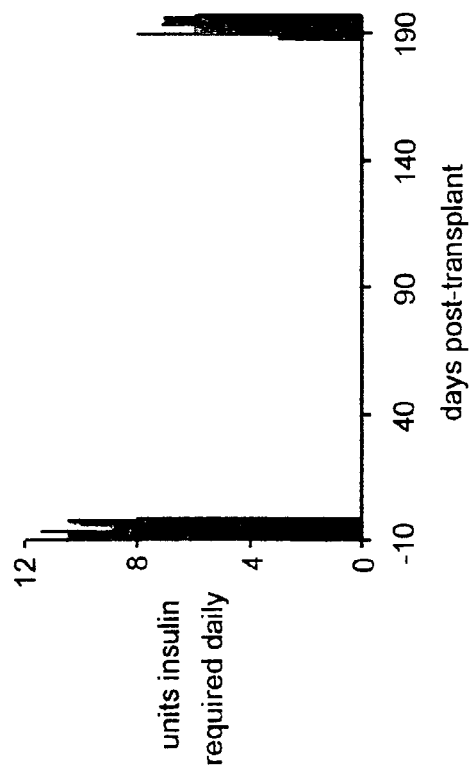

```
ATGGGTGTACTGCTCACACAGAGGACGCTGCTCAGTCTGGTCCTTGCACTCCTGTTTCCA        -19
M~~G~~V~~L~~L~~T~~Q~~R~~T~~L~~L~~S~~L~~V~~L~~A~~L~~L~~F~~P~~         -7

AGCATGGCGAGCATGGCAATGCACGTGGCCCAGCCTGCTGTGGTACTGGCCAGCAGCCGA        +42
S~~M~~A~~S~~M~~A~~M~~H~~V~~A~~Q~~P~~A~~V~~V~~L~~A~~S~~S~~R~~        +14
                 +1

GGCATCGCTAGCTTTGTGTGTGAGTATGCATCTCCAGGCAAAGCCACTGAGGTCCGGGTG       +102
G~~I~~A~~S~~F~~V~~C~~E~~Y~~A~~S~~P~~G~~K~~A~~T~~E~~V~~R~~V~~        +34

ACAGTGCTTCGGCAGGCTGACAGCCAGGTGACTGAAGTCTGTGCGGCAACCTACATGATG       +162
T~~V~~L~~R~~Q~~A~~D~~S~~Q~~V~~T~~E~~V~~C~~A~~A~~T~~Y~~M~~M~~        +54

GGGAATGAGTTGACCTTCCTAGATGATTCCATCTGCACGGGCACCTCCAGTGGAAATCAA       +222
G~~N~~E~~L~~T~~F~~L~~D~~D~~S~~I~~C~~T~~G~~T~~S~~S~~G~~N~~Q~~        +74

GTGAACCTCACTATCCAAGGACTGAGGGCCATGGACACGGGACTCTACATCTGCAAGGTG       +282
V~~N~~L~~T~~I~~Q~~G~~L~~R~~A~~M~~D~~T~~G~~L~~Y~~I~~C~~K~~V~~        +94

GAGCTCATGTACCCACCGCCATACTACGAGGGCATAGGCAACGGAACCCAGATTTATGTA       +342
E~~L~~M~~Y~~P~~P~~P~~Y~~Y~~E~~G~~I~~G~~N~~G~~T~~Q~~I~~Y~~V~~       +114

ATTGATCCAGAACCGTGCCCAGATTCTGATCAGGAGCCCAAATCTTCTGACAAAACTCAC       +402
I~~D~~P~~E~~P~~C~~P~~D~~S~~D~~Q~~E~~P~~K~~S~~S~~D~~K~~T~~H~~       +134

ACATCCCCACCGTCCCCAGCACCTGAACTCCTGGGGGGATCGTCAGTCTTCCTCTTCCCC       +462
T~~S~~P~~P~~S~~P~~A~~P~~E~~L~~L~~G~~G~~S~~S~~V~~F~~L~~F~~P~~       +154

CCAAAACCCAAGGACACCCTCATGATCTCCCGGACCCCTGAGGTCACATGCGTGGTGGTG       +522
P~~K~~P~~K~~D~~T~~L~~M~~I~~S~~R~~T~~P~~E~~V~~T~~C~~V~~V~~V~~       +174

GACGTGAGCCACGAAGACCCTGAGGTCAAGTTCAACTGGTACGTGGACGGCGTGGAGGTG       +582
D~~V~~S~~H~~E~~D~~P~~E~~V~~K~~F~~N~~W~~Y~~V~~D~~G~~V~~E~~V~~       +194

CATAATGCCAAGACAAAGCCGCGGGAGGAGCAGTACAACAGCACGTACCGTGTGGTCAGC       +642
H~~N~~A~~K~~T~~K~~P~~R~~E~~E~~Q~~Y~~N~~S~~T~~Y~~R~~V~~V~~S~~       +214

GTCCTCACCGTCCTGCACCAGGACTGGCTGAATGGCAAGGAGTACAAGTGCAAGGTCTCC       +702
V~~L~~T~~V~~L~~H~~Q~~D~~W~~L~~N~~G~~K~~E~~Y~~K~~C~~K~~V~~S~~       +234

AACAAAGCCCTCCCAGCCCCCATCGAGAAAACCATCTCCAAAGCCAAAGGGCAGCCCCGA       +762
N~~K~~A~~L~~P~~A~~P~~I~~E~~K~~T~~I~~S~~K~~A~~K~~G~~Q~~P~~R~~       +254

GAACCACAGGTGTACACCCTGCCCCCATCCCGGGATGAGCTGACCAAGAACCAGGTCAGC       +822
E~~P~~Q~~V~~Y~~T~~L~~P~~P~~S~~R~~D~~E~~L~~T~~K~~N~~Q~~V~~S~~       +274

CTGACCTGCCTGGTCAAAGGCTTCTATCCCAGCGACATCGCCGTGGAGTGGGAGAGCAAT       +882
L~~T~~C~~L~~V~~K~~G~~F~~Y~~P~~S~~D~~I~~A~~V~~E~~W~~E~~S~~N~~       +294

GGGCAGCCGGAGAACAACTACAAGACCACGCCTCCCGTGCTGGACTCCGACGGCTCCTTC       +942
G~~Q~~P~~E~~N~~N~~Y~~K~~T~~T~~P~~P~~V~~L~~D~~S~~D~~G~~S~~F~~       +314

TTCCTCTACAGCAAGCTCACCGTGGACAAGAGCAGGTGGCAGCAGGGGAACGTCTTCTCA      +1002
F~~L~~Y~~S~~K~~L~~T~~V~~D~~K~~S~~R~~W~~Q~~Q~~G~~N~~V~~F~~S~~       +334

TGCTCCGTGATGCATGAGGCTCTGCACAACCACTACACGCAGAAGAGCCTCTCCCTGTCT      +1062
C~~S~~V~~M~~H~~E~~A~~L~~H~~N~~H~~Y~~T~~Q~~K~~S~~L~~S~~L~~S~~       +354

CCGGGTAAATGA
P~~G~~K~~*
```

FIG. 19

```
ATGGGTGTACTGCTCACACAGAGGACGCTGCTCAGTCTGGTCCTTGCACTCCTGTTTCCA
 M  G  V  L  L  T  Q  R  T  L  L  S  L  V  L  A  L  L  F  P

AGCATGGCGAGCATGGCAATGCACGTGGCCCAGCCTGCTGTGGTACTGGCCAGCAGCCGA
 S  M  A  S  M  A  M  H  V  A  Q  P  A  V  V  L  A  S  S  R

GGCATCGCTAGCTTTGTGTGTGAGTATGCATCTCCAGGCAAATTGACTGAGGTCCGGGTG
 G  I  A  S  F  V  C  E  Y  A  S  P  G  K  L  T  E  V  R  V

ACAGTGCTTCGGCAGGCTGACAGCCAGGTGACTGAAGTCTGTGCGGCAACCTACATGATG
 T  V  L  R  Q  A  D  S  Q  V  T  E  V  C  A  A  T  Y  M  M

GGGAATGAGTTGACCTTCCTAGATGATTCCATCTGCACGGGCACCTCCAGTGGAAATCAA
 G  N  E  L  T  F  L  D  D  S  I  C  T  G  T  S  S  G  N  Q

GTGAACCTCACTATCCAAGGACTGAGGGCCATGGACACGGGACTCTACATCTGCAAGGTG
 V  N  L  T  I  Q  G  L  R  A  M  D  T  G  L  Y  I  C  K  V

GAGCTCATGTACCCACCGCCATACTACGAGGGCATAGGCAACGGAACCCAGATTTATGTA
 E  L  M  Y  P  P  P  Y  Y  E  G  I  G  N  G  T  Q  I  Y  V

ATTGATCCAGAACCGTGCCCAGATTCTGATCAGGAGCCCAAATCTTCTGACAAAACTCAC
 I  D  P  E  P  C  P  D  S  D  Q  E  P  K  S  S  D  K  T  H

ACATCCCCACCGTCCCCAGCACCTGAACTCCTGGGGGGATCGTCAGTCTTCCTCTTCCCC
 T  S  P  P  S  P  A  P  E  L  L  G  G  S  S  V  F  L  F  P

CCAAAACCCAAGGACACCCTCATGATCTCCCGGACCCCTGAGGTCACATGCGTGGTGGTG
 P  K  P  K  D  T  L  M  I  S  R  T  P  E  V  T  C  V  V  V

GACGTGAGCCACGAAGACCCTGAGGTCAAGTTCAACTGGTACGTGGACGGCGTGGAGGTG
 D  V  S  H  E  D  P  E  V  K  F  N  W  Y  V  D  G  V  E  V

CATAATGCCAAGACAAAGCCGCGGGAGGAGCAGTACAACAGCACGTACCGTGTGGTCAGC
 H  N  A  K  T  K  P  R  E  E  Q  Y  N  S  T  Y  R  V  V  S

GTCCTCACCGTCCTGCACCAGGACTGGCTGAATGGCAAGGAGTACAAGTGCAAGGTCTCC
 V  L  T  V  L  H  Q  D  W  L  N  G  K  E  Y  K  C  K  V  S

AACAAAGCCCTCCCAGCCCCCATCGAGAAAACCATCTCCAAAGCCAAAGGGCAGCCCCGA
 N  K  A  L  P  A  P  I  E  K  T  I  S  K  A  K  G  Q  P  R

GAACCACAGGTGTACACCCTGCCCCCATCCCGGGATGAGCTGACCAAGAACCAGGTCAGC
 E  P  Q  V  Y  T  L  P  P  S  R  D  E  L  T  K  N  Q  V  S

CTGACCTGCCTGGTCAAAGGCTTCTATCCCAGCGACATCGCCGTGGAGTGGGAGAGCAAT
 L  T  C  L  V  K  G  F  Y  P  S  D  I  A  V  E  W  E  S  N

GGGCAGCCGGAGAACAACTACAAGACCACGCCTCCCGTGCTGGACTCCGACGGCTCCTTC
 G  Q  P  E  N  N  Y  K  T  T  P  P  V  L  D  S  D  G  S  F

TTCCTCTACAGCAAGCTCACCGTGGACAAGAGCAGGTGGCAGCAGGGGAACGTCTTCTCA
 F  L  Y  S  K  L  T  V  D  K  S  R  W  Q  Q  G  N  V  F  S

TGCTCCGTGATGCATGAGGCTCTGCACAACCACTACACGCAGAAGAGCCTCTCCCTGTCT
 C  S  V  M  H  E  A  L  H  N  H  Y  T  Q  K  S  L  S  L  S

CCGGGTAAATGA
 P  G  K  *
```

FIG. 20

```
ATGGGTGTACTGCTCACACAGAGGACGCTGCTCAGTCTGGTCCTTGCACTCCTGTTTCCA
M--G--V--L--L--T--Q--R--T--L--L--S--L--V--L--A--L--L--F--P--

AGCATGGCGAGCATGGCAATGCACGTGGCCCAGCCTGCTGTGGTACTGGCCAGCAGCCGA
S--M--A--S--M--A--M--H--V--A--Q--P--A--V--V--L--A--S--S--R--

GGCATCGCTAGCTTTGTGTGTGAGTATGCATCTCCAGGCAAAACTACTGAGGTCCGGGTG
G--I--A--S--F--V--C--E--Y--A--S--P--G--K--T--T--E--V--R--V--

ACAGTGCTTCGGCAGGCTGACAGCCAGGTGACTGAAGTCTGTGCGGCAACCTACATGATG
T--V--L--R--Q--A--D--S--Q--V--T--E--V--C--A--A--T--Y--M--M--

GGGAATGAGTTGACCTTCCTAGATGATTCCATCTGCACGGGCACCTCCAGTGGAAATCAA
G--N--E--L--T--F--L--D--D--S--I--C--T--G--T--S--S--G--N--Q--

GTGAACCTCACTATCCAAGGACTGAGGGCCATGGACACGGGACTCTACATCTGCAAGGTG
V--N--L--T--I--Q--G--L--R--A--M--D--T--G--L--Y--I--C--K--V--

GAGCTCATGTACCCACCGCCATACTACGAGGGCATAGGCAACGGAACCCAGATTTATGTA
E--L--M--Y--P--P--P--Y--Y--E--G--I--G--N--G--T--Q--I--Y--V--

ATTGATCCAGAACCGTGCCCAGATTCTGATCAGGAGCCCAAATCTTCTGACAAAACTCAC
I--D--P--E--P--C--P--D--S--D--Q--E--P--K--S--S--D--K--T--H--

ACATCCCCACCGTCCCCAGCACCTGAACTCCTGGGGGGATCGTCAGTCTTCCTCTTCCCC
T--S--P--P--S--P--A--P--E--L--L--G--G--S--S--V--F--L--F--P--

CCAAAACCCAAGGACACCCTCATGATCTCCCGGACCCCTGAGGTCACATGCGTGGTGGTG
P--K--P--K--D--T--L--M--I--S--R--T--P--E--V--T--C--V--V--V--

GACGTGAGCCACGAAGACCCTGAGGTCAAGTTCAACTGGTACGTGGACGGCGTGGAGGTG
D--V--S--H--E--D--P--E--V--K--F--N--W--Y--V--D--G--V--E--V--

CATAATGCCAAGACAAAGCCGCGGGAGGAGCAGTACAACAGCACGTACCGTGTGGTCAGC
H--N--A--K--T--K--P--R--E--E--Q--Y--N--S--T--Y--R--V--V--S--

GTCCTCACCGTCCTGCACCAGGACTGGCTGAATGGCAAGGAGTACAAGTGCAAGGTCTCC
V--L--T--V--L--H--Q--D--W--L--N--G--K--E--Y--K--C--K--V--S--

AACAAAGCCCTCCCAGCCCCCATCGAGAAAACCATCTCCAAAGCCAAAGGGCAGCCCCGA
N--K--A--L--P--A--P--I--E--K--T--I--S--K--A--K--G--Q--P--R--

GAACCACAGGTGTACACCCTGCCCCCATCCCGGGATGAGCTGACCAAGAACCAGGTCAGC
E--P--Q--V--Y--T--L--P--P--S--R--D--E--L--T--K--N--Q--V--S--

CTGACCTGCCTGGTCAAAGGCTTCTATCCCAGCGACATCGCCGTGGAGTGGGAGAGCAAT
L--T--C--L--V--K--G--F--Y--P--S--D--I--A--V--E--W--E--S--N--

GGGCAGCCGGAGAACAACTACAAGACCACGCCTCCCGTGCTGGACTCCGACGGCTCCTTC
G--Q--P--E--N--N--Y--K--T--T--P--P--V--L--D--S--D--G--S--F--

TTCCTCTACAGCAAGCTCACCGTGGACAAGAGCAGGTGGCAGCAGGGGAACGTCTTCTCA
F--L--Y--S--K--L--T--V--D--K--S--R--W--Q--Q--G--N--V--F--S--

TGCTCCGTGATGCATGAGGCTCTGCACAACCACTACACGCAGAAGAGCCTCTCCCTGTCT
C--S--V--M--H--E--A--L--H--N--H--Y--T--Q--K--S--L--S--L--S--

CCGGGTAAATGA------------------------------------------------
P--G--K--*--------------------------------------------------
```

FIG. 21

```
ATGGGTGTACTGCTCACACAGAGGACGCTGCTCAGTCTGGTCCTTGCACTCCTGTTTCCA
 M   G   V   L   L   T   Q   R   T   L   L   S   L   V   L   A   L   L   F   P

AGCATGGCGAGCATGGCAATGCACGTGGCCCAGCCTGCTGTGGTACTGGCCAGCAGCCGA
 S   M   A   S   M   A   M   H   V   A   Q   P   A   V   V   L   A   S   S   R

GGCATCGCTAGCTTTGTGTGTGAGTATGCATCTCCAGGCAAATGGACTGAGGTCCGGGTG
 G   I   A   S   F   V   C   E   Y   A   S   P   G   K   W   T   E   V   R   V

ACAGTGCTTCGGCAGGCTGACAGCCAGGTGACTGAAGTCTGTGCGGCAACCTACATGATG
 T   V   L   R   Q   A   D   S   Q   V   T   E   V   C   A   A   T   Y   M   M

GGGAATGAGTTGACCTTCCTAGATGATTCCATCTGCACGGGCACCTCCAGTGGAAATCAA
 G   N   E   L   T   F   L   D   D   S   I   C   T   G   T   S   S   G   N   Q

GTGAACCTCACTATCCAAGGACTGAGGGCCATGGACACGGGACTCTACATCTGCAAGGTG
 V   N   L   T   I   Q   G   L   R   A   M   D   T   G   L   Y   I   C   K   V

GAGCTCATGTACCCACCGCCATACTACGAGGGCATAGGCAACGGAACCCAGATTTATGTA
 E   L   M   Y   P   P   P   Y   Y   E   G   I   G   N   G   T   Q   I   Y   V

ATTGATCCAGAACCGTGCCCAGATTCTGATCAGGAGCCCAAATCTTCTGACAAAACTCAC
 I   D   P   E   P   C   P   D   S   D   Q   E   P   K   S   S   D   K   T   H

ACATCCCCACCGTCCCCAGCACCTGAACTCCTGGGGGGATCGTCAGTCTTCCTCTTCCCC
 T   S   P   P   S   P   A   P   E   L   L   G   G   S   S   V   F   L   F   P

CCAAAACCCAAGGACACCCTCATGATCTCCCGGACCCCTGAGGTCACATGCGTGGTGGTG
 P   K   P   K   D   T   L   M   I   S   R   T   P   E   V   T   C   V   V   V

GACGTGAGCCACGAAGACCCTGAGGTCAAGTTCAACTGGTACGTGGACGGCGTGGAGGTG
 D   V   S   H   E   D   P   E   V   K   F   N   W   Y   V   D   G   V   E   V

CATAATGCCAAGACAAAGCCGCGGGAGGAGCAGTACAACAGCACGTACCGTGTGGTCAGC
 H   N   A   K   T   K   P   R   E   E   Q   Y   N   S   T   Y   R   V   V   S

GTCCTCACCGTCCTGCACCAGGACTGGCTGAATGGCAAGGAGTACAAGTGCAAGGTCTCC
 V   L   T   V   L   H   Q   D   W   L   N   G   K   E   Y   K   C   K   V   S

AACAAAGCCCTCCCAGCCCCCATCGAGAAAACCATCTCCAAAGCCAAAGGGCAGCCCCGA
 N   K   A   L   P   A   P   I   E   K   T   I   S   K   A   K   G   Q   P   R

GAACCACAGGTGTACACCCTGCCCCCATCCCGGGATGAGCTGACCAAGAACCAGGTCAGC
 E   P   Q   V   Y   T   L   P   P   S   R   D   E   L   T   K   N   Q   V   S

CTGACCTGCCTGGTCAAAGGCTTCTATCCCAGCGACATCGCCGTGGAGTGGGAGAGCAAT
 L   T   C   L   V   K   G   F   Y   P   S   D   I   A   V   E   W   E   S   N

GGGCAGCCGGAGAACAACTACAAGACCACGCCTCCCGTGCTGGACTCCGACGGCTCCTTC
 G   Q   P   E   N   N   Y   K   T   T   P   P   V   L   D   S   D   G   S   F

TTCCTCTACAGCAAGCTCACCGTGGACAAGAGCAGGTGGCAGCAGGGGAACGTCTTCTCA
 F   L   Y   S   K   L   T   V   D   K   S   R   W   Q   Q   G   N   V   F   S

TGCTCCGTGATGCATGAGGCTCTGCACAACCACTACACGCAGAAGAGCCTCTCCCTGTCT
 C   S   V   M   H   E   A   L   H   N   H   Y   T   Q   K   S   L   S   L   S

CCGGGTAAATGA
 P   G   K   *
```

FIG. 22

```
ATGGGTGTAC TGCTCACACA GAGGACGCTG CTCAGTCTGG TCCTTGCACT CCTGTTTCCA
AGCATGGCGA GCATGGCAAT GCACGTGGCC CAGCCTGCTG TGGTACTGGC AGCAGCCGA
GGCATCGCCA GCTTTGTGTG TGAGTATGCA TCTCCAGGCA AAGCCACTGA GGTCCGGGTG
ACAGTGCTTC GGCAGGCTGA CAGCCAGGTG ACTGAAGTCT GTGCGGCAAC CTACATGATG
GGGAATGAGT TGACCTTCCT AGATGATTCC ATCTGCACGG GCACCTCCAG TGGAAATCAA
GTGAACCTCA CTATCCAAGG ACTGAGGGCC ATGGACACGG GACTCTACAT CTGCAAGGTG
GAGCTCATGT ACCCACCGCC ATACTACCTG GCATAGGCA ACGGAACCCA GATTTATGTA
ATTGATCCAG AACCGTGCCC AGATTCTGAT CAGGAGCCCA AATCTTCTGA CAAAACTCAC
ACATCCCCAC CGTCCCAGC ACCTGAACTC CTGGGGGGAT CGTCAGTCTT CCTCTTCCCC
CCAAAACCCA AGGACACCCT CATGATCTCC CGGACCCCTG AGGTCACATG CGTGGTGGTG
GACGTGAGCC ACGAAGACCC TGAGGTCAAG TTCAACTGGT ACGTGGACGG CGTGGAGGTG
CATAATGCCA AGACAAAGCC GCGGGAGGAG CAGTACAACA GCACGTACCG TGTGGTCAGC
GTCCTCACCG TCCTGCACCA GGACTGGCTG AATGGCAAGG AGTACAAGTG CAAGGTCTCC
AACAAAGCCC TCCCAGCCCC CATCGAGAAA ACCATCTCCA AAGCCAAAGG CAGCCCCGA
GAACCACAGG TGTACACCCT GCCCCCATCC CGGGATGAGC TGACCAAGAA CCAGGTCAGC
CTGACCTGCC TGGTCAAAGG CTTCTATCCC AGCGACATCG CCGTGGAGTG GGAGAGCAAT
GGGCAGCCGG AGAACAACTA CAAGACCACG CCTCCCGTGC TGGACTCCGA CGGCTCCTTC
TTCCTCTACA GCAAGCTCAC CGTGGACAAG AGCAGGTGGC AGCAGGGGAA CGTCTTCTCA
TGCTCCGTGA TGCATGAGGC TCTGCACAAC CACTACACGC AGAAGAGCCT CTCCCTGTCT
CCGGGTAAAT GA
```

FIG. 23

MGVLLTQRTL LSLVLALLFP SMASMAMHVA QPAVVLASSR GIASFVCEYA     50

SPGKATEVRV TVLRQADSQV TEVCAATYMM GNELTFLDDS ICTGTSSGNQ    100

VNLTIQGLRA MDTGLYICKV ELMYPPPYYL GIGNGTQIYV IDPEPCPDSD    150

QEPKSSDKTH TSPPSPAPEL LGGSSVFLFP PKPKDTLMIS RTPEVTCVVV    200

DVSHEDPEVK FNWYVDGVEV HNAKTKPREE QYNSTYRVVS VLTVLHQDWL    250

NGKEYKCKVS NKALPAPIEK TISKAKGQPR EPQVYTLPPS RDELTKNQVS    300

LTCLVKGFYP SDIAVEWESN GQPENNYKTT PPVLDSDGSF FLYSKLTVDK    350

SRWQQGNVFS CSVMHEALHN HYTQKSLSLS PGK

FIG. 24

METHODS FOR PROTECTING ALLOGENEIC ISLET TRANSPLANT USING SOLUBLE CTLA4 MUTANT MOLECULES

This application claims priority to provisional application, U.S. Ser. No. 60/293,402, filed May 23, 2001, the contents of which are hereby incorporated by reference in their entirety into this application.

Throughout this application various publications are referenced. The disclosures of these publications are hereby incorporated by reference in their entirety into this application in order to more fully describe the state of the art to which the invention pertains.

FIELD OF THE INVENTION

The present invention relates generally to the field of inhibiting islet cell transplant rejection. In particular, the invention relates to methods for treating diabetes, including type-1 and type-2 diabetes, by administering to a subject an effective amount of soluble CTLA4 mutant molecules.

BACKGROUND OF THE INVENTION

Organ transplantation has emerged as a preferred method of treatment for many forms of life-threatening diseases that involve organ damage. Improved results in clinical transplantation have been achieved primarily through the development of increasingly potent non-specific immunosuppressive drugs to inhibit rejection responses (*Lancet*, 345:1321-1325 (1995)). While short-term results have improved, long-term outcomes remain inadequate. Currently, life-long immunosuppressive agents are required to combat chronic rejection of the transplanted organ, and the use of these agents dramatically increases the risks of cardiovascular disease, infections and malignancies.

The development of strategies to promote the acceptance of allogeneic tissues without the need for chronic immunosuppression may reduce the risk of these life-threatening complications, and greatly expand the application of organ, tissue and cellular transplantation for diseases such as the hemoglobinopathies, genetic immunodeficiencies, and autoimmune diseases.

Insulin-dependent diabetes mellitus (IDDM) is one of the most commonly occurring metabolic disorders in the world. In the United States, IDDM affects approximately one in 300 to 400 people, and epidemiological studies suggest that the incidence of IDDM is continuing to increase. IDDM is caused by an autoimmune response that results in the T lymphocyte-mediated destruction of the insulin-producing islet cells of the pancreas.

Once the clinical symptoms of IDDM become evident, the most commonly employed therapy for controlling the clinical symptoms of IDDM is exogenous insulin replacement. Although insulin replacement therapy allows most IDDM patients to lead somewhat normal lives, it does not completely restore metabolic homeostasis, and as a result, severe complications including dysfunctions of the eye, kidney, heart, and other organs are common in diabetic patients undergoing insulin replacement therapy.

A long-sought treatment for IDDM patients is islet transplantation. However, transplanted insulin-producing islet cells are often rapidly destroyed by the same autoimmune response that previously destroyed the patients own islet cells. Of the 260 allografts transplanted since 1990, only 12.4% have resulted in insulin independence for periods of more than one week, and only 8.25% have been insulin independent for periods of more than one year (Linsley et al. Diabetes (1997) 46: 1120-3). In the majority of these procedures, the base regimen of immunosuppression consisted of antibody induction with an anti-lymphocyte globulin combined with cyclosporin, azathiprine, and glucocorticoids.

For any type of transplantation procedure, a balance between efficacy and toxicity is a key factor for its clinical acceptance. With respect to islet transplantation, a further concern is that many of the current immunosuppressive agents with particular glucocortecoids or a calcineurin inhibitor, such as Tarcolimus, damage beta cells or induce peripheral insulin resistance (Zeng et al. Surgery (1993) 113: 98-102).

A steroid-free immunosuppressive protocol ("Edmonton protocol") that includes sirolimus, low dose Tarcolimus, and a monoclonal antibody (mAb) against IL-2 receptor has been used in a trial of islet transplantation alone for patients with type-1 diabetes (Shapiro, A. M. J. et al, (2000), N. Eng. J. Med., 343: 230-238).

The recent success using the "Edmonton protocol" has renewed enthusiasm for the use of islet transplantation to treat diabetes. However, concerns regarding toxicity of the Tarcolimus may limit the application of this therapy in humans. Biological agents that block key T cell costimulatory signals, in particular the CD28 pathway, are potential alternatives to protect allogeneic islets. Examples of agents that block the CD28 pathway include but are not limited to soluble CTLA4 including mutant CTLA4 molecules.

SUMMARY OF INVENTION

The present invention provides methods for treating immune system diseases, by administering to a subject soluble CTLA4 mutant molecules, which bind to CD80 and/or CD86 molecules on CD80 and/or CD86-positive cells, thereby inhibiting endogenous CD80 and/or CD86 molecules from binding CTLA4 and/or CD28 on T cells, and thus, blocking key T cell costimulatory signals, in particular the CD28 pathway.

Soluble CTLA4 mutant molecules include, but are not limited to, L104EA29Y, a molecule having mutations in the extracellular domain of CTLA4 at alanine at position +29 and/or at leucine at position +104, wherein alanine at position 29 is substituted with tyrosine, and leucine at position 104 is substituted with glutamic acid. The CTLA4 mutant molecules further comprise a moiety, such as an immunoglobulin molecule, that renders the mutant protein soluble.

In a preferred embodiment, the L104EA29Y is L104EA29YIg (FIG. 3).

The present invention further provides methods for inhibiting islet cell transplant rejection in a subject by administering L104EA29Y (e.g., L104EA29YIg) to the subject undergoing islet cell transplant.

The invention also provides methods for treating diabetes in a subject, by administering an immunosuppressive regimen comprising L104EA29Y (e.g., L104EA29YIg) to the subject diagnosed with diabetes and transplanting islet cells.

The present invention further provides pharmaceutical compositions for treating diabetes, the compositions comprising a pharmaceutically acceptable carrier and soluble CTLA4 mutant, e.g., L104EA29Y.

BRIEF DESCRIPTION OF THE FIGURES

FIG. 1 depicts the complete nucleotide (SEQ ID NO.: 1) and amino acid sequence (SEQ ID NO.: 2) for human CTLA4 receptor fused to the oncostatin M signal peptide. The oncostatin M signal peptide is indicated at position −25 to −1.

FIG. 2 depicts a nucleotide (SEQ ID NO.: 3) and amino acid sequence (SEQ ID NO.: 4) of a CTLA4Ig having a signal peptide; a wild type amino acid sequence of the extracellular domain of CTLA4 starting at methionine at position +1 to aspartic acid at position +124, or starting at alanine at position −1 to aspartic acid at position +124; and an Ig region.

FIG. 3 depicts a nucleotide (SEQ ID NO.: 5) and amino acid sequence (SEQ ID NO.: 6) of a CTLA4 mutant molecule (L104EA29YIg) comprising a signal peptide; a mutated extracellular domain of CTLA4 starting at methionine at position +1 and ending at aspartic acid at position +124, or starting at alanine at position −1 and ending at aspartic acid at position +124; and an Ig region as described in Example 1, infra.

FIG. 4 is a line graph illustrating fasting plasma glucose level in a normal subject, as described in Example 3, infra

FIG. 15B shows an expanded view of the S25-R33 region and the MYPPPY region indicating the location and side-chain orientation of the avidity enhancing mutations, L104 and A29.

FIG. 16 depicts fasting blood glucose for LEA29YIg treated (A) and control (B) recipients of allogeneic islets (representative animals) before and after transplantation. All animals underwent surgical pancreatectomy at least 2 weeks before transplantation (mean pretransplant insulin requirement of 8.76±0.18 units/day) (C) After intraportal infusion of allogeneic islets, recipients quickly became euglycemic requiring no exogenous insulin posttransplant. (D) Diabetes induction and posttransplant islet function was confirmed by intravenous glucose tolerance test before transplantation and at 1 month and 3 months posttransplant, as described in Example 3, infra.

FIG. 19 shows the nucleotide and amino acid sequences of L104EIg (SEQ ID NOs.: 7-8), as described in Example 2, infra.

FIG. 20 shows the nucleotide and amino acid sequence of L104EA29LIg (SEQ ID NOs.: 9-10).

FIG. 21 shows the nucleotide and amino acid sequences of L104EA29TIg (SEQ ID NOs.: 11-12).

FIG. 22 shows the nucleotide and amino acid sequences of L104EA29WIg (SEQ ID NOs.: 13-14).

FIG. 23 shows the nucleotide sequence of a CTLA4Ig (SEQ ID NO.: 15) having a signal peptide; a wild type amino acid sequence of the extracellular domain of CTLA4 starting at methionine at position +1 to aspartic acid at position +124, or starting at alanine at position −1 to aspartic acid at position +124; and an Ig region.

FIG. 24 shows the amino acid sequence of a CTLA4Ig (SEQ ID NO.: 16) having a signal peptide; a wild type amino acid sequence of the extracellular domain of CTLA4 starting at methionine at position +1 to aspartic acid at position +124, or starting at alanine at position −1 to aspartic acid at position +124; and an Ig region.

DETAILED DESCRIPTION OF THE INVENTION

Definitions

Figure 5:
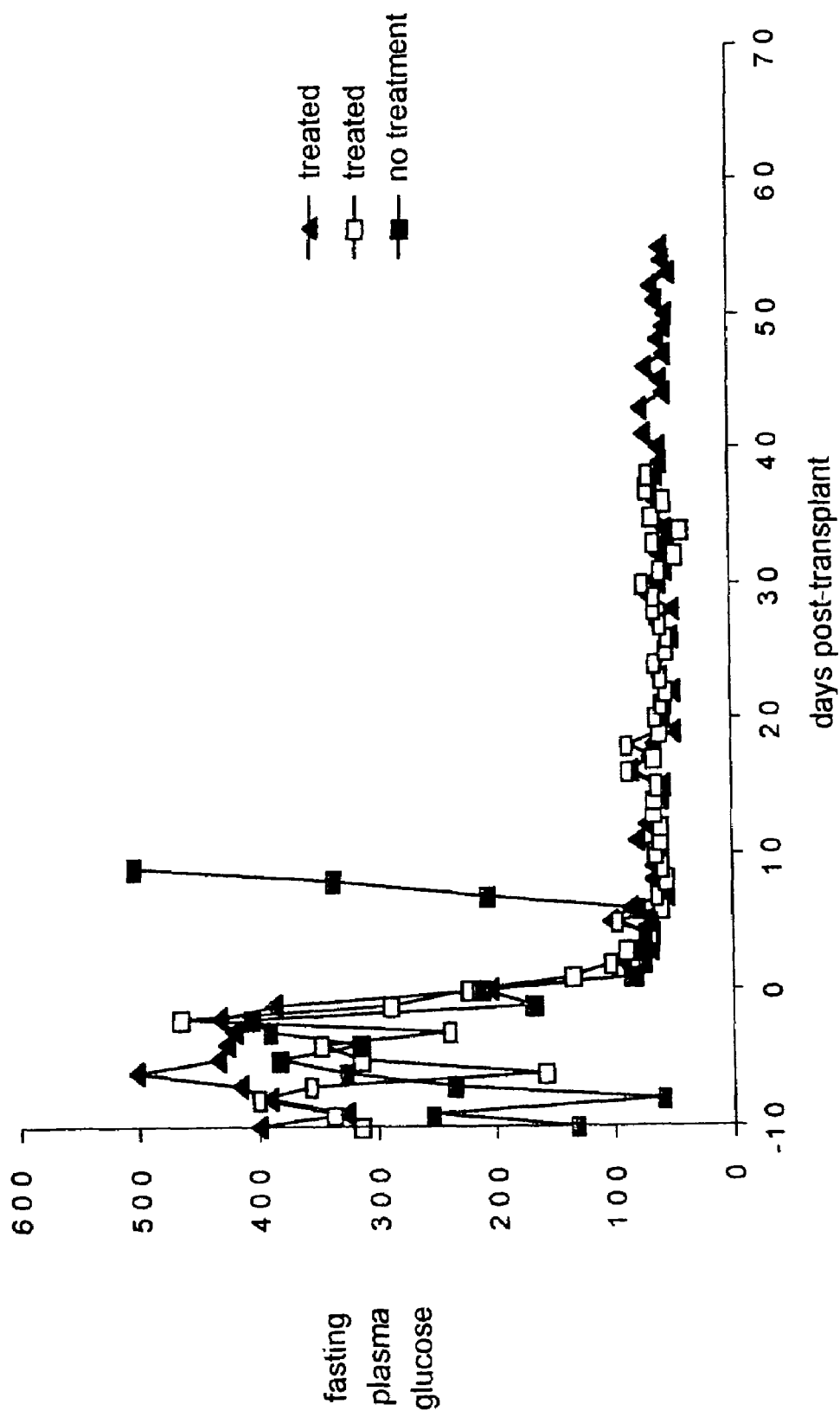
FIG. 5 is a line graph illustrating fasting plasma glucose level in pancreatectomized subjects with transplanted pancreatic islet cells as described in Example 3. The animals were transplanted with islet cells on day 0, and either treated with an immunosuppressive regimen containing L104EA29YIg, and a base immunosuppressive regimen (treated), or only a base immunosuppressive regimen (control). The base immunosuppressive regimen contained rapamycin and anti-human IL2R.

All scientific and technical terms used in this application have meanings commonly used in the art unless otherwise specified. As used in this application, the following words or phrases have the meanings specified.

As used herein "wild type CTLA4" has the amino acid sequence of naturally occurring, full length CTLA4 (U.S. Pat. Nos. 5,434,131, 5,844,095, 5,851,795), or any portion thereof which binds a B7 molecule (CD80 and/or CD86), or interferes with a B7 molecule (e.g., CD80 and/or CD86) so that it blocks their binding to their ligand, or blocks their binding to the extracellular domain of CTLA4 or portions thereof. In particular embodiments, wild type CTLA4 begins with methionine at position +1 and ends at aspartic acid at position +124, or wild type CTLA4 begins with alanine at position −1 and ends at aspartic acid at position +124. In other embodiments, wild type CTLA4 consists of the 187 amino acids of the CTLA4 receptor as disclosed in FIG. 3 of U.S. Pat. Nos. 5,434,131, 5,844,095, 5,851,795, and shown here as FIG. 1. Wild type CTLA4 is a cell surface protein, having an N-terminal extracellular domain, a transmembrane domain, and a C-terminal cytoplasmic domain. The extracellular domain binds to target antigens, such as CD80 and CD86. In a cell, the naturally occurring, wild type CTLA4 protein is translated as an immature polypeptide, which includes a signal peptide at the N-terminal end. The immature polypeptide undergoes post-translational processing, which includes cleavage and removal of the signal peptide to generate a CTLA4 cleavage product having a newly generated N-terminal end that differs from the N-terminal end in the immature form. One skilled in the art will appreciate that additional post-translational processing may occur, which removes one or more of the amino acids from the newly generated N-terminal end of the CTLA4 cleavage product. The mature form of the CTLA4 molecule includes the extracellular domain of CTLA4, or any portion thereof, which binds to CD80 and/or CD86.

As used herein "the extracellular domain of CTLA4" is the portion of the CTLA4 receptor that extends outside the cell membrane, and includes any portion of CTLA4 that extends outside the cell membrane that recognizes and binds CTLA4 ligands, such as a B7 molecule (e.g., CD80 and/or CD86 molecules). For example, an extracellular domain of CTLA4 comprises methionine at position +1 to aspartic acid at position +124 (FIG. 2). Alternatively, an extracellular domain of CTLA4 comprises alanine at position +1 to aspartic acid at position +125 (FIG. 1). The extracellular domain includes fragments or derivatives of CTLA4 that bind a B7 molecule (e.g., CD80 and/or CD86).

As used herein a "non-CTLA4 protein sequence" or "non-CTLA4 molecule" is defined as any molecule that does not bind CD80 and/or CD86 and does not interfere with the binding of CTLA4 to its target. An example includes, but is not limited to, an immunoglobulin (Ig) constant region or portion thereof. Preferably, the Ig constant region is a human or monkey Ig constant region, e.g., human C(gamma)1, including the hinge, CH2 and CH3 regions. The Ig constant region can be mutated to reduce its effector functions (U.S. Pat. Nos: 5,637,481; and 6,090,914).

As used herein, "soluble" refers to any molecule, or fragments and derivatives thereof, not bound or attached to a cell, i.e., circulating. For example, CTLA4, L104EA29YIg, B7 or CD28 can be made soluble by attaching an immunoglobulin (Ig) moiety to the extracellular domain of CTLA4, B7 or CD28, respectively. Other molecules can be papillomavirus E7 gene product (E7), melanoma-associated antigen p97 (p97) or HIV env protein (env gp120). Alternatively, a molecule such as CTLA4 can be rendered soluble by removing its transmembrane domain. Typically, the soluble molecules used in the methods of the invention do not include a signal (or leader) sequence.

"CTLA4Ig" is a soluble fusion protein comprising an extracellular domain of CTLA4, or a portion thereof that binds CD80 and/or CD86, joined to an Ig tail. A particular embodiment comprises the extracellular domain of wild type CTLA4 starting at methionine at position +1 and ending at aspartic acid at position +124; or starting at alanine at position −1 to aspartic acid at position +124; a junction amino acid residue glutamine at position +125; and an immunoglobulin portion encompassing glutamic acid at position +126 through lysine at position +357 (FIG. 2). DNA encoding CTLA4Ig was deposited on May 31, 1991 with the American Type Culture Collection (ATCC), 10801 University Blvd., Manassas, Va. 20110-2209 under the provisions of the Budapest Treaty, and has been accorded ATCC accession number ATCC 68629; Linsley, P., et al., 1994 *Immunity* 1:793-80). CTLA4Ig-24, a Chinese Hamster Ovary (CHO) cell line expressing CTLA4Ig was deposited on May 31, 1991 with ATCC identification number CRL-10762). The soluble CTLA4Ig molecules used in the methods and/or kits of the invention may or may not include a signal (leader) peptide sequence. Typically, in the methods and/or kits of the invention, the molecules do not include a signal peptide sequence.

As used herein, "soluble CTLA4 molecules" means non-cell-surface-bound (i.e., circulating) CTLA4 molecules (wildtype or mutant) or any functional portion of a CTLA4 molecule that binds B7 including, but not limited to: CTLA4Ig fusion proteins (e.g., ATCC 68629), wherein the extracellular domain of CTLA4 is fused to an immunoglobulin (Ig) moiety rendering the fusion molecule soluble, or fragments and derivatives thereof; proteins with the extracellular domain of CTLA4 fused or joined with a portion of a biologically active or chemically active protein such as the papillomavirus E7 gene product (CTLA4-E7), melanoma-associated antigen p97 (CTLA4-p97) or HIV env protein (CTLA4-env gp120), or fragments and derivatives thereof; hybrid (chimeric) fusion proteins such as CD28/CTLA4Ig, or fragments and derivatives thereof; CTLA4 molecules with the transmembrane domain removed to render the protein soluble (Oaks, M. K., et al., 2000 *Cellular Immunology* 201:144-153), or fragments and derivatives thereof. "Soluble CTLA4 molecules" also include fragments, portions or derivatives thereof, and soluble CTLA4 mutant molecules having CTLA4 binding activity. The soluble CTLA4 molecules used in the methods of the invention may or may not include a signal (leader) peptide sequence. Typically, in the methods of the invention, the molecules do not include a signal peptide sequence.

As used herein, a "fusion protein" is defined as one or more amino acid sequences joined together using methods well known in the art and as described in U.S. Pat. Nos. 5,434,131 or 5,637,481. The joined amino acid sequences thereby form one fusion protein.

As used herein a "CTLA4 mutant molecule" is a molecule that can be full length CTLA4 or portions thereof (derivatives or fragments) that have a mutation or multiple mutations in CTLA4 (preferably in the extracellular domain of CTLA4) so that it is similar but not identical to the wild type CTLA4 molecule. CTLA4 mutant molecules bind a B7 molecule (e.g., either CD80 or CD86, or both). Mutant CTLA4 molecules may include a biologically or chemically active non-CTLA4 molecule therein or attached thereto. The mutant molecules may be soluble (i.e., circulating) or bound to a surface. CTLA4 mutant molecules can include the entire extracellular domain of CTLA4 or portions thereof, e.g., fragments or derivatives. CTLA4 mutant molecules can be made synthetically or recombinantly.

As used herein, the term "mutation" is a change in the nucleotide or amino acid sequence of a wild-type polypeptide. The present invention provides a mutation or a change in the wild type CTLA4 extracellular domain. The changes in the wild type CTLA4 sequence include conservative and non-conservative changes. The change can be an amino acid change which includes substitutions, deletions, additions, or truncations. A mutant molecule can have one or more mutations. Mutations in a nucleotide sequence may or may not result in a mutation in the amino acid sequence as is well understood in the art. In that regard, certain nucleotide codons encode the same amino acid. Examples include nucleotide codons CGT, CGG, CGC, and CGA encoding the amino acid, arginine (R); or codons GAT, and GAC encoding the amino acid, aspartic acid (D). Thus, a protein can be encoded by one or more nucleic acid molecules that differ in their specific nucleotide sequence, but still encode protein molecules having identical sequences. The amino acid coding sequence is as follows:

| Amino Acid | Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

"L104EA29YIg" is a fusion protein that is a soluble CTLA4 mutant molecule comprising an extracellular domain of wildtype CTLA4 having amino acid changes A29Y (a tyrosine amino acid residue substituting for an alanine at position 29) and L104E (a glutamic acid amino acid residue substituting for a leucine at position +104), or a portion thereof that binds a B7 molecule, joined to an Ig tail (included in FIG. 3; DNA encoding L104EA29YIg was deposited with the American Type Culture Collection on Jun. 20, 2000 and assigned ATCC number PTA-2104). The soluble L104EA29YIg molecules used in the methods and/or kits of the invention may or may not include a signal (leader) peptide sequence. Typically, in the methods and/or kits of the invention, the molecules do not include a signal peptide sequence.

The mutant molecule may have one or more mutations. As used herein, a "non-CTLA4 protein sequence" or "non-CTLA4 molecule" means any protein molecule that does not bind B7 and does not interfere with the binding of CTLA4 to its target. An example includes, but is not limited to, an immunoglobulin (Ig) constant region or portion thereof.

Preferably, the Ig constant region is a human or monkey Ig constant region, e.g., human C(gamma)1, including the hinge, CH2 and CH3 regions. The Ig constant region can be mutated to reduce its effector functions (U.S. Pat. Nos. 5,637,481, 5,844,095 and 5,434,131).

As used herein, a "fragment" or "portion" is any part or segment of a molecule e.g. CTLA4 or CD28, preferably the extracellular domain of CTLA4 or CD28 or a part or segment thereof, that recognizes and binds its target, e.g., a B7 molecule.

As used herein, "B7" refers to the B7 family of molecules including, but not limited to, B7-1 (CD80) (Freeman et al, 1989, J Immunol. 143:2714-2722, herein incorporated by reference in its entirety), B7-2 (CD86) (Freeman et al, 1993, Science 262:909-911 herein incorporated by reference in its entirety; Azuma et al, 1993, Nature 366:76-79 herein incorporated by reference in its entirety) that may recognize and bind CTLA4 and/or CD28.

As used herein, "CD28" refers to the molecule that recognizes and binds B7 as described in U.S. Ser. Nos. 5,580,756 and 5,521,288 (herein incorporated by reference in their entirety).

As used herein, "B7-positive cells" are any cells with one or more types of B7 molecules expressed on the cell surface.

As used herein, a "derivative" is a molecule that shares sequence similarity and activity of its parent molecule. For example, a derivative of CTLA4 includes a soluble CTLA4 molecule having an amino acid sequence at least 70% similar to the extracellular domain of wildtype CTLA4, and which recognizes and binds B7 e.g. CTLA4Ig or soluble CTLA4 mutant molecule L104EA29YIg.

As used herein, to "block" or "inhibit" a receptor, signal or molecule means to interfere with the activation of the receptor, signal or molecule, as detected by an art-recognized test. For example, blockage of a cell-mediated immune response can be detected by determining reduction of Rheumatic Disease associated symptoms. Blockage or inhibition may be partial or total.

As used herein, "blocking B7 interaction" means to interfere with the binding of B7 to its ligands, such as CD28 and/or CTLA4, thereby obstructing T-cell and B7-positive cell interactions. Examples of agents that block B7 interactions include, but are not limited to, molecules such as an antibody (or portion or derivative thereof) that recognizes and binds to the any of CTLA4, CD28 or B7 molecules (e.g. B7-1, B7-2); a soluble form (or portion or derivative thereof) of the molecules such as soluble CTLA4; a peptide fragment or other small molecule designed to interfere with the cell signal through the CTLA4/CD28/B7-mediated interaction. In a preferred embodiment, the blocking agent is a soluble CTLA4 molecule, such as CTLA4Ig (ATCC 68629) or L104EA29YIg (ATCC PTA-2104), a soluble CD28 molecule such as CD28Ig (ATCC 68628), a soluble B7 molecule such as B7Ig (ATCC 68627), an anti-B7 monoclonal antibody (e.g. ATCC HB-253, ATCC CRL-2223, ATCC CRL-2226, ATCC HB-301, ATCC HB-11341 and monoclonal antibodies as described in by Anderson et al in U.S. Pat. No. 6,113,898 or Yokochi et al., 1982. J. Immun., 128(2):823-827), an anti-CTLA4 monoclonal antibody (e.g. ATCC HB-304, and monoclonal antibodies as described in references 82-83) and/or an anti-CD28 monoclonal antibody (e.g. ATCC HB 11944 and mAb 9.3 as described by Hansen (Hansen et al., 1980. Immunogenetics 10: 247-260) or Martin (Martin et al., 1984. J. Clin. Immun., 4(1):18-22)).

As used herein, "immune system disease" means any disease mediated by T-cell interactions with B7-positive cells including, but not limited to, autoimmune diseases, graft related disorders and immunoproliferative diseases.

Examples of immune system diseases include graft versus host disease (GVHD) (e.g., such as may result from bone marrow transplantation, or in the induction of tolerance), immune disorders associated with graft transplantation rejection, chronic rejection, and tissue or cell allo- or xenografts, including solid organs, skin, islets, muscles, hepatocytes, neurons. Examples of immunoproliferative diseases include, but are not limited to, psoriasis, T-cell lymphoma, T-cell acute lymphoblastic leukemia, testicular angiocentric T-cell lymphoma, benign lymphocytic angiitis, lupus (e.g. lupus erythematosus, lupus nephritis), Hashimoto's thyroiditis, primary myxedema, Graves' disease, pernicious anemia, autoimmune atrophic gastritis, Addison's disease, diabetes (e.g. insulin dependent diabetes mellitus, type I diabetes mellitus, type II diabetes mellitus), good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatic diseases (e.g. rheumatoid arthritis), polymyositis, scleroderma, and mixed connective tissue disease.

As used herein, "subject" includes but is not limited to human, non-human primates (e.g., monkey, ape), sheep, rabbit, pig, dog, cat, mouse, or rat.

As used herein, "tissue transplant" is defined as a tissue of all, or part of, an organ that is transplanted to a recipient subject. In certain embodiments, the tissue is from one or more solid organs. Examples of tissues or organs include, but are not limited to, skin, heart, lung, pancreas, kidney, liver, bone marrow, pancreatic islet cells, pluripotent stem cells, cell suspensions, and genetically modified cells. The tissue can be removed from a donor subject, or can be grown in vitro. The transplant can be an autograft, isograft, allograft, or xenograft, or a combination thereof.

As used herein, "transplant rejection" is defined as the nearly complete, or complete, loss of viable graft tissue from the recipient subject.

As used herein, "encapsulation" is defined as a process that immunoisolates cells and/or cell clusters, which produce and secrete therapeutic substances, e.g. insulin, and to the medical use of these formulations. The encapsulation process involves the placement of the cells and/or cell clusters within a semipermeable membrane barrier prior to transplantation in order to avoid rejection by the immune system. The molecular weight cut-off of the encapsulating membrane can be controlled by the encapsulation procedure so as to exclude inward diffusion of immunoglobulin and lytic factors of the complement system, but allow the passage of smaller molecules such as glucose and insulin. Encapsulation permits the islet cells to respond physiologically to changes in blood glucose but prevents contact with components of the immune system. Methods of encapsulation of pancreatic islet cells are described in U.S. Pat. No. 6,080,412.

As used herein, "ligand" refers to a molecule that specifically recognizes and binds another molecule, for example, a ligand for CTLA4 is a CD80 and/or CD86 molecule.

As used herein, "a soluble ligand which recognizes and binds CD80 and/or CD86 antigen" includes ligands such as CTLA4Ig, CD28Ig or other soluble forms of CTLA4 and CD28; recombinant CTLA4 and CD28; mutant CTLA4 molecules such as L104EA29YIg; and any antibody molecule, fragment thereof or recombinant binding protein that recognizes and binds a CD80 and/or CD86 antigen. These agents are also considered "immunosuppressive agents".

As used herein, "costimulatory pathway" is defined as a biochemical pathway resulting from interaction of costimulatory signals on T cells and antigen presenting cells (APCs). Costimulatory signals help determine the magnitude of an immunological response to an antigen. One costimulatory signal is provided by the interaction with T cell receptors CD28 and CTLA4 with CD80 and/or CD86 molecules on APCs.

As used herein, "CD80 and/or CD86" includes B7-1 (also called CD80). B7-2 (also called CD86), B7-3 (also called CD74), and the B7 family, e.g., a combination of B7-1, B7-2, and/or B7-3.

As used herein, "costimulatory blockade" is defined as a protocol of administering to a subject, one or more agents that interfere or block a costimulatory pathway, as described above. Examples of agents that interfere with the costimulatory blockade include, but are not limited to, soluble CTLA4, mutant CTLA4, soluble CD28, anti-B7 monoclonal antibodies (mAbs), soluble CD40, and anti-gp39 mAbs. In one embodiment, L104EA29YIg is a preferred agent that interferes with the costimulatory blockade.

As used herein, "T cell depleted bone marrow" is defined as bone marrow removed from bone that has been exposed to an anti-T cell protocol. An anti-T cell protocol is defined as a procedure for removing T cells from bone marrow. Methods of selectively removing T cells are well known in the art. An example of an anti-T cell protocol is exposing bone marrow to T cell specific antibodies, such as anti-CD3, anti-CD4, anti-CD5, anti-CD8, and anti-CD90 monoclonal antibodies, wherein the antibodies are cytotoxic to the T cells. Alternatively, the antibodies can be coupled to magnetic particles to permit removal of T cells from bone marrow using magnetic fields. Another example of an anti-T cell protocol is exposing bone marrow T cells to anti-lymphocyte serum or anti-thymocyte globulin.

As used herein, "tolerizing dose of T cell depleted bone marrow" is defined as an initial dose of T cell depleted bone marrow that is administered to a subject for the purpose of inactivating potential donor reactive T cells.

As used herein, "engrafting dose of T cell depleted bone marrow" is defined as a subsequent dose of T cell depleted bone marrow that is administered to a subject for the purpose of establishing mixed hematopoietic chimerism. The engrafting dose of T cell depleted bone marrow will accordingly be administered after the tolerizing dose of T cell depleted bone marrow.

As used herein, "mixed hematopoietic chimerism" is defined as the presence of donor and recipient blood progenitor and mature cells (e.g., blood deriving cells) in the absence (or undetectable presence) of an immune response.

As used herein "Donor-recipient pairings" are defined based on molecular typing using a panel of previously defined major histocompatibilty alleles (8 class I and 12 class II) (Lobashevsky A, et al., *Tissue Antigens* 54:254-263, (1999); Knapp L A, et al., *Tissue Antigens* 50:657-661, (1997); Watkins D. I., *Crit Rev Immunol* 15:1-29, (1995)). Pairings maximized disparity at both class I and II loci.

As used herein, "administer" or "administering" to a subject includes but not limited to intravenous (i.v.) administration, intraperitoneal (i.p.) administration, intramuscular (i.m.) administration, subcutaneous administration, oral administration, administration by injection, as a suppository, or the implantation of a slow-release device such as a miniosmotic pump, to the subject.

As used herein, "pharmaceutically acceptable carrier" includes any material which, when combined with the reactive agent, retains the reactive agent's biological activity, e.g., binding specificity and is non-reactive with the subject's immune system. Examples include, but are not limited to, any of the standard pharmaceutical carriers such as a phosphate buffered saline solution, water, emulsions such as oil/water emulsion, and various types of wetting agents. Other carriers may also include sterile solutions, tablets, including coated tablets and capsules. Typically, such carriers contain excipients, such as starch, milk, sugar, certain types of clay, gelatin, stearic acid or salts, thereof, magnesium or calcium stearate, talc, vegetable fats or oils, gums, glycols, or other known excipients. Such carriers may also include flavor and color additives or other ingredients. Compositions comprising such carriers are formulated by well-known conventional methods.

As used herein, "immunosuppressive agents" are defined as a composition having one or more types of molecules that prevent the occurrence of an immune response, or weaken a subject's immune system. Preferably, the agents reduce or prevent T cell proliferation. Some agents may inhibit T cell proliferation by inhibiting interaction of T cells with other antigen presenting cells (APCs). One example of APCs is B cells. Examples of agents that interfere with T cell interactions with APCs, and thereby inhibit T cell proliferation, include, but are not limited to, ligands for CD80 and/or CD86 antigens, ligands for CTLA4 antigen, and ligands for CD28 antigen. Examples of ligands for CD80 and/or CD86 antigens include, but are not limited to, soluble CTLA4, soluble CTLA4 mutant, soluble CD28, or monoclonal antibodies that recognize and bind CD80 and/or CD86 antigens, or fragments thereof. One preferred agent is L104EA29YIg. Ligands for CTLA4 or CD28 antigens include monoclonal antibodies that recognize and bind CTLA4 and/or CD28, or fragments thereof. Other ligands for CTLA4 or CD28 include soluble CD80 and/or CD86 molecules, such as CD80 and/or CD86Ig. Persons skilled in the art will readily understand that other agents or ligands can be used to inhibit the interaction of CD28 with CD80 and/or CD86.

Immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE$^R$), etanercept, TNFα blockers, a biological agent that targets an inflammatory cytokine, and Non-Steroidal Anti-Inflammatory Drug (NSAIDs). NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Compositions of the Invention

The present invention provides compositions for treating immune diseases, such as diabetes, comprising soluble CTLA4 molecules. The invention further provides compositions for inhibiting transplant rejections, e.g. islet cell transplant rejection for treating diabetes. Further, the present invention provides compositions comprising a biological agent that inhibits T-cell function but not T-cell depletion in a human by contacting B7-positive cells in the human with a soluble CTLA4. Examples of soluble CTLA4 include CTLA4Ig and soluble CTLA4 mutant molecules such as L104EA29YIg, L104EA29LIg, L104EA29TIg, and L104EA29WIg CTLA4 molecules, with mutant or wildtype sequences, may be rendered soluble by deleting the CTLA4 transmembrane segment (Oaks, M. K., et al., 2000 Cellular Immunology 201:144-153).

Alternatively, soluble CTLA4 molecules, with mutant or wildtype sequences, may be fusion proteins, wherein the CTLA4 molecules are fused to non-CTLA4 moieties such as immunoglobulin (Ig) molecules that render the CTLA4 molecules soluble. For example, a CTLA4 fusion protein may include the extracellular domain of CTLA4 fused to an immunoglobulin constant domain, resulting in the CTLA4Ig molecule (FIG. 2) (Linsley, P. S., et al., 1994 Immunity 1:793-80).

For clinical protocols, it is preferred that the immunoglobulin moiety does not elicit a detrimental immune response in a subject. The preferred moiety is the immunoglobulin constant region, including the human or monkey immunoglobulin constant regions. One example of a suitable immunoglobulin region is human Cγ1, including the hinge, CH2 and CH3 regions which can mediate effector functions such as binding to Fc receptors, mediating complement-dependent cytotoxicity (CDC), or mediate antibody-dependent cell-mediated cytotoxicity (ADCC). The immunoglobulin moiety may have one or more mutations therein, (e.g., in the CH2 domain, to reduce effector functions such as CDC or ADCC) where the mutation modulates the binding capability of the immunoglobulin to its ligand, by increasing or decreasing the binding capability of the immunoglobulin to Fc receptors. For example, mutations in the immunoglobulin moiety may include changes in any or all its cysteine residues within the hinge domain, for example, the cysteines at positions +130, +136, and +139 are substituted with serine (FIG. 24). The immunoglobulin moiety may also include the proline at position +148 substituted with a serine, as shown in FIG. 24. Further, the mutations in the immunoglobulin moiety may include having the leucine at position +144 substituted with phenylalanine, leucine at position +145 substituted with glutamic acid, or glycine at position +147 substituted with alanine.

Additional non-CTLA4 moieties for use in the soluble CTLA4 molecules or soluble CTLA4 mutant molecules include, but are not limited to, p97 molecule, env gp120 molecule, E7 molecule, and ova molecule (Dash, B. et al. 1994 J. Gen. Virol. 75 (Pt 6):1389-97; Ikeda, T., et al. 1994 Gene 138(1-2):193-6; Falk, K., et al. 1993 Cell. Immunol. 150(2):447-52; Fujisaka, K. et al. 1994 Virology 204(2):789-93). Other molecules are also possible (Gerard, C. et al. 1994 Neuroscience 62(3):721; Byrn, R. et al. 1989 63(10):4370; Smith, D. et al. 1987 Science 238:1704; Lasky, L. 1996 Science 233:209).

The present invention provides soluble CTLA4 molecules including a signal peptide sequence linked to the N-terminal end of the extracellular domain of the CTLA4 portion of the molecule. The signal peptide can be any sequence that will permit secretion of the mutant molecule, including the signal peptide from oncostatin M (Malik, et al., 1989 Molec. Cell. Biol. 9: 2847-2853), or CD5 (Jones, N. H. et al., 1986 Nature 323:346-349), or the signal peptide from any extracellular protein. The soluble CTLA4 molecule of the invention can include the oncostatin M signal peptide linked at the N-terminal end of the extracellular domain of CTLA4, and the human immunoglobulin molecule (e.g., hinge, CH2 and CH3) linked to the C-terminal end of the extracellular domain (wildtype or mutated) of CTLA4. This molecule includes the oncostatin M signal peptide encompassing an amino acid sequence having methionine at position −26 through alanine at position −1, the CTLA4 portion encompassing an amino acid sequence having methionine at position +1 through aspartic acid at position +124, a junction amino acid residue glutamine at position +125, and the immunoglobulin portion encompassing an amino acid sequence having glutamic acid at position +126 through lysine at position +357.

In one embodiment, the soluble CTLA4 mutant molecules of the invention, comprising the mutated CTLA4 sequences described infra, are fusion molecules comprising human IgC(gamma)1 (i.e. IgCγ1) moieties fused to the mutated CTLA4 fragments. The soluble CTLA4 mutant molecules can comprise one or more mutations (e.g., amino acid substitutions, deletions, or insertions) in the extracellular domain of CTLA4.

For example, the soluble CTLA4 mutant molecules can include a mutation or mutations within or in close proximity to the region encompassed by serine at position +25 through arginine at position +33 (e.g., S25-R33, using standard single-letter amino acid symbols). The mutant CTLA4 molecules can include an amino acid substitution at any one or more of the following positions: S25, P26, G27, K28, A29, T30, E31, or R33.

In another embodiment, the soluble CTLA4 mutant molecules can include a mutation or mutations within or in close proximity to the region encompassed by glutamic acid at position +95 to glycine at position +107 (e.g., E95-G107) The mutant CTLA4 molecules can include an amino acid substitution at any one or more of the following positions: K93, L96, M97, Y98, P99, P100, P101, Y102, Y103, L104, G105, I106, and G107.

Additionally, the invention provides soluble CTLA4 mutant molecules having a mutation or mutations within or in close proximity to the region encompassed by asparagine +108 to isoleucine at position +115 (e.g., N108-I115). The mutant CTLA4 molecule can include an amino acid substitution at any one or more of the following positions: L104, G105, I106, G107, Q111, Y113, or I115.

In one embodiment, the soluble CTLA4 mutant molecules comprise IgCγ1 fused to a CTLA4 fragment comprising a single-site mutation in the extracellular domain. The extracellular domain of CTLA4 comprises methionine at position +1 through aspartic acid at position +124 (e.g., FIG. 1). The extracellular portion of the CTLA4 can comprise alanine at position −1 through aspartic acid at position +124 (e.g., FIG. 1).

Examples of single-site mutations include the following wherein the leucine at position +104 is changed to any other amino acid:

| Single-site mutant: | Codon change: |
|---|---|
| L104EIg | Glutamic acid GAG |
| L104SIg | Serine AGT |
| L104TIg | Threonine ACG |
| L104AIg | Alanine GCG |
| L104WIg | Tryptophan TGG |
| L104QIg | Glutamine CAG |
| L104KIg | Lysine AAG |
| L104RIg | Arginine CGG |
| L104GIg | Glycine GGG |

Further, the invention provides mutant molecules having the extracellular domain of CTLA4 with two mutations, fused to an Ig Cγ1 moiety. Examples include the following wherein the leucine at position +104 is changed to another amino acid (e.g. glutamic acid) and the glycine at position +105, the serine at position +25, the threonine at position +30 or the alanine at position +29 is changed to any other amino acid:

| Double-site mutants: | Codon change: |
|---|---|
| L104EG105FIg | Phenylalanine TTC |
| L104EG105WIg | Tryptophan TGG |
| L104EG105LIg | Leucine CTT |
| L104ES25RIg | Arginine CGG |
| L104ET30GIg | Glycine GGG |
| L104ET30NIg | Asparagine AAT |
| L104EA29YIg | Tyrosine TAT |
| L104EA29LIg | Leucine TTG |
| L104EA29TIg | Threonine ACT |
| L104EA29WIg | Tryptophan TGG |

Further still, the invention provides mutant molecules having the extracellular domain of CTLA4 comprising three mutations, fused to an Ig Cγ1 moiety. Examples include the following wherein the leucine at position +104 is changed to another amino acid (e.g. glutamic acid), the alanine at position +29 is changed to another amino acid (e.g. tyrosine) and the serine at position +25 is changed to another amino acid:

| Triple-site Mutants: | Codon changes: |
|---|---|
| L104EA29YS25KIg | Lysine AAA |
| L104EA29YS25KIg | Lysine AAG |
| L104EA29YS25NIg | Asparagine AAC |
| L104EA29YS25RIg | Arginine CGG |

Soluble CTLA4 mutant molecules may have a junction amino acid residue which is located between the CTLA4 portion and the Ig portion of the molecule. The junction amino acid can be any amino acid, including glutamine. The junction amino acid can be introduced by molecular or chemical synthesis methods known in the art.

The invention provides soluble CTLA4 mutant molecules comprising a single-site mutation in the extracellular domain of CTLA4 such as L104EIg (as included in FIG. 19) or L104SIg, wherein L104EIg and L104SIg are mutated in their CTLA4 sequences so that leucine at position +104 is substituted with glutamic acid or serine, respectively. The single-site mutant molecules further include CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated so that the cysteines at positions +130, +136, and +139 are substituted with serine, and the proline at position +148 is substituted with serine. Alternatively, the single-site soluble CTLA4 mutant molecule may have a CTLA4 portion encompassing alanine at position −1 through aspartic acid at position +124.

The invention provides soluble CTLA4 mutant molecules comprising a double-site mutation in the extracellular domain of CTLA4, such as L104EA29YIg, L104EA29LIg, L104EA29TIg or L104EA29WIg, wherein leucine at position +104 is substituted with a glutamic acid and alanine at position +29 is changed to tyrosine, leucine, threonine and tryptophan, respectively. The sequences for L104EA29YIg, L104EA29LIg, L104EA29TIg and L104EA29WIg, starting at methionine at position +1 and ending with lysine at position +357, plus a signal (leader) peptide sequence are included in the sequences as shown in FIGS. 3 and 20-22 respectively. The double-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

The invention provides soluble CTLA4 mutant molecules comprising a double-site mutation in the extracellular domain of CTLA4, such as L104EG105FIg, L104EG105WIg and L104EG105LIg, wherein leucine at position +104 is substituted with a glutamic acid and glycine at position +105 is substituted with phenylalanine, tryptophan and leucine, respectively. The double-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

The invention provides L104ES25RIg which is a double-site mutant molecule including a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that serine at position +25 is substituted with arginine, and leucine at position +104 is substituted with glutamic acid. Alternatively, L104ES25RIg can have a CTLA4 portion encompassing alanine at position −1 through aspartic acid at position +124.

The invention provides soluble CTLA4 mutant molecules comprising a double-site mutation in the extracellular domain of CTLA4, such as L104ET30GIg and L104ET30NIg, wherein leucine at position +104 is substituted with a glutamic acid and threonine at position +30 is substituted with glycine and asparagine, respectively. The double-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

The invention provides soluble CTLA4 mutant molecules comprising a triple-site mutation in the extracellular domain of CTLA4, such as L104EA29YS25KIg, L104EA29YS25NIg, L104EA29YS25RIg, wherein leucine at position +104 is substituted with a glutamic acid, alanine at position +29 is changed to tyrosine and serine at position +25 is changed to lysine, asparagine and arginine, respectively. The triple-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

Additional embodiments of soluble CTLA4 mutant molecules include chimeric CTLA4/CD28 homologue mutant molecules that bind a B7 (Peach, R. J., et al., 1994 *J Exp Med* 180:2049-2058). Examples of these chimeric CTLA4/CD28 mutant molecules include HS1, HS2, HS3, HS4, HS5, HS6, HS4A, HS4B, HS7, HS8, HS9, HS10, HS11, HS12, HS13 and HS14 (U.S. Pat. No. 5,773,253).

Preferred embodiments of the invention are soluble CTLA4 molecules such as CTLA4Ig (as shown in FIG. 2, starting at methionine at position +1 and ending at lysine at position +357) and soluble CTLA4 mutant L104EA29YIg (as shown in FIG. 3, starting at methionine at position +1 and ending at lysine at position +357).

The invention further provides nucleic acid molecules comprising nucleotide sequences encoding the amino acid sequences corresponding to the soluble CTLA4 molecules of the invention. In one embodiment, the nucleic acid molecule is a DNA (e.g., cDNA) or a hybrid thereof. DNA encoding CTLA4Ig (FIG. 2) was deposited on May 31, 1991 with the American Type Culture Collection (ATCC), 10801 University Blvd., Manassas, Va. 20110-2209 and has been accorded ATCC accession number ATCC 68629. DNA encoding L104EA29YIg (sequence included in FIG. 3) was deposited on Jun. 19, 2000 with ATCC and has been accorded ATCC accession number PTA-2104. Alternatively, the nucleic acid molecules are RNA or a hybrid thereof.

CTLA4 Hybrids

The present invention provides soluble CTLA4 mutant molecules comprising at least the extracellular domain of CTLA4 or portions thereof that bind CD80 and/or CD86. The extracellular portion of CTLA4 comprises methionine at position +1 through aspartic acid at position +124 (e.g., FIG. 1). The extracellular portion of the CTLA4 can comprise alanine at position −1 through aspartic acid at position +124 (e.g., FIG. 1). The extracellular portion of the CTLA4 can comprise glutamic acid at position +95 through cysteine at position +120. The extracellular portion of the CTLA4 can comprise methionine at position +1 through cysteine at position +21 and glutamic acid at position +95 through aspartic acid at position +122. The extracellular portion of the CTLA4 can comprise methionine at position +1 through tyrosine at position +23 and valine at position +32 through aspartic acid at position +122. The extracellular portion of the CTLA4 can comprise alanine at position +24 through glutamic acid at position +31 and glutamic acid at position +95 through aspartic acid at position +122. The extracellular portion of the CTLA4 can comprise alanine at position +24 through glutamic acid at position +31 and glutamic acid at position +95 through isoleucine at position +112. The extracellular portion of the CTLA4 can comprise alanine at position +24 through glutamic acid at position +31 and tyrosine at position +113 through aspartic acid at position +122. The extracellular portion of the CTLA4 can comprise alanine at position +50 through glutamic acid at position +57 and glutamic acid at position +95 through aspartic acid at position +122. The extracellular portion of the CTLA4 can comprise alanine at position +24 through glutamic acid at position +31; alanine at position +50 through glutamic acid at position +57; and glutamic acid at position +95 through aspartic acid at position +122. The extracellular portion of the CTLA4 can comprise alanine at position +50 through glutamic acid at position +57 and glutamic acid at position +95 through isoleucine at position +112. The extracellular portion of the CTLA4 can comprise alanine at position +24 through glutamic acid at position +31; alanine at position +50 through glutamic acid at position +57; and glutamic acid at position +95 through aspartic acid at position +122. The extracellular portion of CTLA4 can comprise alanine at position +24 through valine at position +94. The extracellular portion of CTLA4 can comprise alanine at position −1 through cysteine at position +21. The extracellular portion of CTLA4 can comprise methionine at position +1 through cysteine at position +21. The extracellular portion of CTLA4 can comprise glutamic acid at position +95 through aspartic acid at position +122. The extracellular portion of CTLA4 can comprise alanine at position −1 through valine at position +94. The extracellular portion of CTLA4 can comprise methionine at position +1 through valine at position +94. The extracellular portion of CTLA4 can comprise alanine at position +24 through glutamic acid at position +31. The extracellular portion of CTLA4 can comprise alanine at position −1 through tyrosine at position +23. The extracellular portion of CTLA4 can comprise methionine at position +1 through tyrosine at position +23. The extracellular portion of CTLA4 can comprise valine at position +32 through aspartic acid at position +122. The extracellular portion of CTLA4 can comprise tyrosine at position +113 through aspartic acid at position +122. The extracellular portion of CTLA4 can comprise glutamic acid at position +95 through isoleucine at position +112. The extracellular portion of CTLA4 can comprise alanine at position +50 through glutamic acid at position +57.

Methods for Producing the Molecules of the Invention

Expression of CTLA4 mutant molecules can be in prokaryotic cells. Prokaryotes most frequently are represented by various strains of bacteria. The bacteria may be a gram positive or a gram negative. Other microbial strains may also be used.

Nucleotide sequences encoding CTLA4 mutant molecules can be inserted into a vector designed for expressing foreign sequences in prokaryotic cells such as *E. coli*. These vectors can include commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived $P_L$ promoter and N-gene ribosome binding site (Shimatake, et al., (1981) *Nature* 292:128).

Such expression vectors will also include origins of replication and selectable markers, such as a beta-lactamase or neomycin phosphotransferase gene conferring resistance to antibiotics, so that the vectors can replicate in bacteria and cells carrying the plasmids can be selected for when grown in the presence of antibiotics, such as ampicillin or kanamycin.

The expression plasmid can be introduced into prokaryotic cells via a variety of standard methods, including but not limited to $CaCl_2$-shock (Cohen, (1972) *Proc. Natl. Acad. Sci. USA* 69:2110, and Sambrook et al. (eds.), "*Molecular Cloning: A Laboratory Manual*", 2nd Edition, Cold Spring Harbor Press, (1989)) and electroporation.

In accordance with the practice of the invention, eukaryotic cells are also suitable host cells. Examples of eukaryotic cells include any animal cell, whether primary or immortalized, yeast (e.g., *Saccharomyces cerevisiae, Schizosaccharomyces pombe*, and *Pichia pastoris*), and plant cells. Myeloma, COS and CHO cells are examples of animal cells that may be used as hosts. Particular CHO cells include, but are not limited to, DG44 (Chasin, et al., 1986 *Som. Cell. Molec. Genet.* 12:555-556; Kolkekar 1997 *Biochemistry* 36:10901-10909), CHO-K1 (ATCC No. CCL-61), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), and RR-CHOK1 designated ECACC 92052129 (CAMR, Salisbury, Wiltshire, UK). Exemplary plant cells include tobacco (whole plants, cell culture, or callus), corn, soybean, and rice cells. Corn, soybean, and rice seeds are also acceptable.

Nucleotide sequences encoding the CTLA4 mutant molecules can also be inserted into a vector designed for expressing foreign sequences in a eukaryotic host. The regulatory elements of the vector can vary according to the particular eukaryotic host. The nucleic acid molecule that encodes L104EA29YIg is contained in pD16 L104EA29YIg and was deposited on Jun. 19, 2000 with the American Type Culture Collection (ATCC), 10801 University Blvd., Manassas, Va. 20110-2209 (ATCC No. PTA-2104). The pD16 L104EA29YIg vector is a derivative of the pcDNA3 vector (INVITROGEN).

Commonly used eukaryotic control sequences for use in expression vectors include promoters and control sequences compatible with mammalian cells such as, for example, CMV promoter (CDM8 vector) and avian sarcoma virus (ASV) (πLN vector). Other commonly used promoters include the early and late promoters from Simian Virus 40 (SV40) (Fiers, et al., (1973) *Nature* 273:113), or other viral promoters such as those derived from polyoma, Adenovirus 2, and bovine papilloma virus. An inducible promoter, such as hMTII (Karin, et al., (1982) *Nature* 299:797-802) may also be used.

Vectors for expressing CTLA4 mutant molecules in eukaryotes may also carry sequences called enhancer regions. These are important in optimizing gene expression and are found either upstream or downstream of the promoter region.

Examples of expression vectors for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene)), retroviral vectors (e.g., pFB vectors (Stratagene)), pCDNA-3 (Invitrogen) or modified forms thereof, adenoviral vectors; Adeno-associated virus vectors, baculovirus vectors, yeast vectors (e.g., pESC vectors (Stratagene)).

Nucleotide sequences encoding CTLA4 mutant molecules can integrate into the genome of the eukaryotic host cell and replicate as the host genome replicates. Alternatively, the vector carrying CTLA4 mutant molecules can contain origins of replication allowing for extrachromosomal replication.

For expressing the nucleotide sequences in *Saccharomyces cerevisiae*, the origin of replication from the endogenous yeast plasmid, the 2μ circle can be used. (Broach, (1983) *Meth. Enz.* 101:307). Alternatively, sequences from the yeast genome capable of promoting autonomous replication can be used (see, for example, Stinchcomb et al., (1979) *Nature* 282:39); Tschemper et al., (1980) *Gene* 10:157; and Clarke et al., (1983) *Meth. Enz.* 101:300).

Transcriptional control sequences for yeast vectors include promoters for the synthesis of glycolytic enzymes (Hess et al., (1968) *J. Adv. Enzyme Reg.* 7:149; Holland et al., (1978) *Biochemistry* 17:4900). Additional promoters known in the art include the CMV promoter provided in the CDM8 vector (Toyama and Okayama, (1990) FEBS 268: 217-221); the promoter for 3-phosphoglycerate kinase (Hitzeman et al., (1980) *J. Biol. Chem.* 255:2073), and those for other glycolytic enzymes.

Other promoters are inducible because they can be regulated by environmental stimuli or the growth medium of the cells. These inducible promoters include those from the genes for heat shock proteins, alcohol dehydrogenase 2, isocytochrome C, acid phosphatase, enzymes associated with nitrogen catabolism, and enzymes responsible for maltose and galactose utilization.

Regulatory sequences may also be placed at the 3' end of the coding sequences. These sequences may act to stabilize messenger RNA. Such terminators are found in the 3' untranslated region following the coding sequences in several yeast-derived and mammalian genes.

Exemplary vectors for plants and plant cells include, but are not limited to, Agrobacterium $T_i$ plasmids, cauliflower mosaic virus (CaMV), and tomato golden mosaic virus (TGMV).

General aspects of mammalian cell host system transformations have been described by Axel (U.S. Pat. No. 4,399,216 issued Aug. 16, 1983). Mammalian cells can be transformed by methods including but not limited to, transfection in the presence of calcium phosphate, microinjection, electroporation, or via transduction with viral vectors. Methods for introducing foreign DNA sequences into plant and yeast genomes include (1) mechanical methods, such as microinjection of DNA into single cells or protoplasts, vortexing cells with glass beads in the presence of DNA, or shooting DNA-coated tungsten or gold spheres into cells or protoplasts; (2) introducing DNA by making cell membranes permeable to macromolecules through polyethylene glycol treatment or subjection to high voltage electrical pulses (electroporation); or (3) the use of liposomes (containing cDNA) which fuse to cell membranes.

Expression of CTLA4 mutant molecules can be detected by methods known in the art. For example, the mutant molecules can be detected by Coomassie staining SDS-PAGE gels and immunoblotting using antibodies that bind CTLA4. Protein recovery can be performed using standard protein purification means, e.g., affinity chromatography or ion-exchange chromatography, to yield substantially pure product (R. Scopes in: "*Protein Purification, Principles and Practice*", Third Edition, Springer-Verlag (1994)).

The invention further provides soluble CTLA4 mutant protein molecules produced by the methods herein.

CTLA4IG Codon-Based Mutagenesis

In one embodiment, site-directed mutagenesis and a novel screening procedure were used to identify several mutations in the extracellular domain of CTLA4 that improve binding avidity for CD86. In this embodiment, mutations were carried out in residues in the regions of the extracellular domain of CTLA4 from serine 25 to arginine 33, the C' strand (alanine 49 and threonine 51), the F strand (lysine 93, glutamic acid 95 and leucine 96), and in the region from methionine 97 through tyrosine 102, tyrosine 103 through glycine 107 and in the G strand at positions glutamine 111, tyrosine 113 and isoleucine 115. These sites were chosen based on studies of chimeric CD28/CTLA4 fusion proteins (Peach et al., *J. Exp. Med.,* 1994, 180:2049-2058), and on a model predicting which amino acid residue side chains would be solvent exposed, and a lack of amino acid residue identity or homology at certain positions between CD28 and CTLA4. Also, any residue which is spatially in close proximity (5 to 20 Angstrom Units) to the identified residues is considered part of the present invention.

To synthesize and screen soluble CTLA4 mutant molecules with altered affinities for CD80 and/or CD86, a two-step strategy was adopted. The experiments entailed first generating a library of mutations at a specific codon of an extracellular portion of CTLA4 and then screening these by BIAcore analysis to identify mutants with altered reactivity to CD80 or CD86. The Biacore assay system (Pharmacia, Piscataway, N.J.) uses a surface plasmon resonance detector system that essentially involves covalent binding of either CD80Ig or CD86Ig to a dextran-coated sensor chip which is located in a detector. The test molecule can then be injected into the chamber containing the sensor chip and the amount of complementary protein that binds can be assessed based on the change in molecular mass which is physically associated with the dextran-coated side of the sensor chip; the change in molecular mass can be measured by the detector system.

Pharmaceutical Compositions of the Invention

The invention includes pharmaceutical compositions for use in the treatment of immune system diseases comprising pharmaceutically effective amounts of soluble CTLA4 mutant molecules. In certain embodiments, the immune system diseases are mediated by CD28- and/or CTLA4-positive cell interactions with CD80 and/or CD86 positive cells. The soluble CTLA4 molecules are preferably soluble CTLA4 molecules with wildtype sequence and/or soluble CTLA4 molecules having one or more mutations in the extracellular domain of CTLA4. The pharmaceutical composition can include soluble CTLA4 or CTLA4 mutant protein molecules and/or nucleic acid molecules, and/or vectors encoding the molecules. In a preferred embodiment, the soluble CTLA4 mutant molecule has the amino acid sequence of the extracellular domain of CTLA4 as shown in either FIGS. 3 (L104EA29Y). Even more preferably, the soluble CTLA4 mutant molecule is L104EA29YIg as disclosed herein shown in FIG. 3. The compositions may additionally include other therapeutic agents, including, but not limited to, immunosuppressive agents, NSAIDs, corticosteroids, glucocococticoids, drugs, toxins, enzymes, antibodies, or conjugates.

An embodiment of the pharmaceutical composition comprises an effective amount of a soluble CTLA4 molecule alone or in combination with an effective amount of at least one other therapeutic agent, including an immunosuppressive agent, or NSAID.

Effective amounts of soluble CTLA4 in the pharmaceutical composition can range about 0.1 to 100 mg/kg weight of the subject. In another embodiment, the effective amount can be an amount about 0.5 to 5 mg/kg weight of a subject, about 5 to 10 mg/kg weight of a subject, about 10 to 15 mg/kg weight of a subject, about 15 to 20 mg/kg weight of a subject, about 20 to 25 mg/kg weight of a subject, about 25 to 30 mg/kg weight of a subject, about 30 to 35 mg/kg weight of a subject, about 35 to 40 mg/kg weight of a subject, about 40 to 45 mg/kg of a subject, about 45 to 50 mg/kg weight of a subject, about 50 to 55 mg/kg weight of a subject, about 55 to 60 mg/kg weight of a subject, about 60 to 65 mg/kg weight of a subject, about 65 to 70 mg/kg weight of a subject, about 70 to 75 mg/kg weight of a subject, about 75 to 80 mg/kg weight of a subject, about 80 to 85 mg/kg weight of a subject, about 85 to 90 mg/kg weight of a subject, about 90 to 95 mg/kg weight of a subject, or about 95 to 100 mg/kg weight of a subject. In an embodiment, the effective amount is 2 mg/kg weight of a subject. In another embodiment, the effective amount is 10 mg/kg weight of a subject. In an embodiment, the effective amount of a soluble CTLA4 molecule is 2 mg/kg weight of a subject. In an embodiment, the effective amount of a soluble CTLA4 molecule is 10 mg/kg weight of a subject.

The amount of an immunosuppressive agent administered to a subject varies depending on several factors including the efficacy of the drug on a specific subject and the toxicity (i.e. the tolerability) of a drug to a specific subject.

Methotrexate is commonly administered in an amount about 0.1 to 40 mg per week with a common dosage ranging about 5 to 30 mg per week. Methotrexate may be administered to a subject in various increments: about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, or about 35 to 40 mg/week. In one embodiment, an effective amount of an immunosuppressive agent, including methotrexate, is an amount about 10 to 30 mg/week.

Effective amounts of methotrexate range about 0.1 to 40 mg/week. In one embodiment, the effective amount is ranges about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, or about 35 to 40 mg/week. In one embodiment, methotrexate is administered in an amount ranging about 10 to 30 mg/week.

Cyclophosphamide, an alkylating agent, may be administered in dosages ranging about 1 to 10 mg/kg body weight per day.

Cyclosporine (e.g. NEORAL$^R$) also known as Cyclosporin A, is commonly administered in dosages ranging from about 1 to 10 mg/kg body weight per day. Dosages ranging about 2.5 to 4 mg per body weight per day are commonly used.

Chloroquine or hydroxychloroquine (e.g. PLAQUENIL$^R$), is commonly administered in dosages ranging about 100 to 1000 mg daily. Preferred dosages range about 200-600 mg administered daily.

Sulfasalazine (e.g., AZULFIDINE EN-tabs$^R$) is commonly administered in amounts ranging about 50 to 5000 mg per day, with a common dosage of about 2000 to 3000 mg per day for adults. Dosages for children are commonly about 5 to 100 mg/kg of body weight, up to 2 grams per day.

Gold salts are formulated for two types of administration: injection or oral. Injectable gold salts are commonly prescribed in dosages about 5 to 100 mg doses every two to four weeks. Orally administered gold salts are commonly prescribed in doses ranging about 1 to 10 mg per day.

D-penicillamine or penicillamine (CUPRIMINE$^R$) is commonly administered in dosages about 50 to 2000 mg per day, with preferred dosages about 125 mg per day up to 1500 mg per day.

Azathioprine is commonly administered in dosages of about 10 to 250 mg per day. Preferred dosages range about 25 to 200 mg per day.

Anakinra (e.g. KINERET$^R$) is an interleukin-1 receptor antagonist. A common dosage range for anakinra is about 10 to 250 mg per day, with a recommended dosage of about 100 mg per day.

Infliximab (REMICADE$^R$) is a chimeric monoclonal antibody that binds to tumor necrosis factor alpha (TNFα). Infliximab is commonly administered in dosages about 1 to 20 mg/kg body weight every four to eight weeks. Dosages of about 3 to 10 mg/kg body weight may be administered every four to eight weeks depending on the subject.

Etanercept (e.g. ENBREL$^R$) is a dimeric fusion protein that binds the tumor necrosis factor (TNF) and blocks its interactions with TNF receptors. Commonly administered dosages of etanercept are about 10 to 100 mg per week for adults with a preferred dosage of about 50 mg per week. Dosages for juvenile subjects range about 0.1 to 50 mg/kg body weight per week with a maximum of about 50 mg per week.

Leflunomide (ARAVA$^R$) is commonly administered at dosages about 1 and 100 mg per day. A common daily dosage is about 10 to 20 mg per day.

The pharmaceutical compositions also preferably include suitable carriers and adjuvants which include any material which when combined with the molecule of the invention (e.g., a soluble CTLA4 mutant molecule, e.g., L104EA29YIg) retains the molecule's activity and is non-reactive with the subject's immune system. Examples of suitable carriers and adjuvants include, but are not limited to, human serum albumin; ion exchangers; alumina; lecithin; buffer substances, such as phosphates; glycine; sorbic acid; potassium sorbate; and salts or electrolytes, such as protamine sulfate. Other examples include any of the standard pharmaceutical carriers such as a phosphate buffered saline solution; water; emulsions, such as oil/water emulsion; and various types of wetting agents. Other carriers may also include sterile solutions; tablets, including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Such compositions may also be formulated within various lipid compositions, such as, for example, liposomes as well as in various polymeric compositions, such as polymer microspheres.

The pharmaceutical compositions of the invention can be administered using conventional modes of administration including, but not limited to, intravenous (i.v.) administration, intraperitoneal (i.p.) administration, intramuscular (i.m.) administration, subcutaneous administration, oral administration, administration as a suppository, or as a topical contact, or the implantation of a slow-release device such as a miniosmotic pump, to the subject.

The pharmaceutical compositions of the invention may be in a variety of dosage forms, which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the compositions of this invention depends upon the severity and course of the disease, the patient's health and response to treatment and the judgment of the treating physician. Accordingly, the dosages of the compositions should be titrated to the individual patient.

The soluble CTLA4 mutant molecules may be administered to a subject in an amount and for a time (e.g. length of time and/or multiple times) sufficient to block endogenous B7 (e.g., CD80 and/or CD86) molecules from binding their respective ligands, in the subject. Blockage of endogenous B7/ligand binding thereby inhibits interactions between B7-positive cells (e.g., CD80- and/or CD86-positive cells) with CD28- and/or CTLA4-positive cells. Dosage of a therapeutic agent is dependent upon many factors including, but not limited to, the type of tissue affected, the type of autoimmune disease being treated, the severity of the disease, a subject's health, and a subject's response to the treatment with the agents. Accordingly, dosages of the agents can vary depending on the subject and the mode of administration. The soluble CTLA4 mutant molecules may be administered in an amount between 0.1 to 20.0 mg/kg weight of the patient/day, preferably between 0.5 to 10.0 mg/kg/day. Administration of the pharmaceutical compositions of the invention can be performed over various times. In one embodiment, the pharmaceutical composition of the invention can be administered for one or more hours. In addition, the administration can be repeated depending on the severity of the disease as well as other factors as understood in the art.

Methods of the Invention

The present invention provides methods for treating immune system diseases and auto-immune diseases in a subject comprising administering to the subject an effective amount of a soluble CTLA4 or a CTLA4 mutant molecule which binds CD80 and/or CD86 molecules on CD80 and/or CD86-positive cells so as to inhibit binding of CD80 and/or CD86 to CTLA4 and/or CD28. The methods comprise administering a therapeutic composition, comprising soluble CTLA4 or CTLA4 mutant molecules of the invention, to a subject in an amount effective to relieve at least one of the symptoms associated with immune system diseases. Additionally, the invention may provide long-term therapy for immune system diseases by blocking the T-cell/B7-positive cell interactions, thereby blocking T-cell activation/stimulation by co-stimulatory signals such as B7 binding to CD28, leading to induction of T-cell anergy or tolerance.

The soluble CTLA4 or CTLA4 mutant molecules of the invention exhibit inhibitory properties in vivo. Under conditions where T-cell/B7-positive cell interactions, for example T cell/B cell interactions, are occurring as a result of contact between T cells and B7-positive cells, binding of introduced CTLA4 molecules to react to B7-positive cells, for example B cells, may interfere, i.e., inhibit, the T cell/B7-positive cell interactions resulting in regulation of immune responses. Inhibition of T cell responses by administering a soluble CTLA4 molecule may also be useful for treating autoimmune disorders. Many autoimmune disorders result from inappropriate activation of T cells that are reactive against autoantigens, and which promote the production of cytokines and autoantibodies that are involved in the pathology of the disease. Administration of L104EA29YIg molecule in a subject suffering from or susceptible to an autoimmune disorder may prevent the activation of autoreactive T cells and may reduce or eliminate disease symptoms. This method may also comprise administering to the subject L104EA29YIg molecule of the invention, alone or together, with additional ligands, such as those reactive with IL-2, IL-4, or γ-interferon.

The invention provides methods for regulating immune responses. Immune responses may be down-regulated (reduced) by the soluble CTLA4 or CTLA4 mutant molecules of the invention may be by way of inhibiting or blocking an immune response already in progress or may involve preventing the induction of an immune response. The soluble CTLA4 or CTLA4 mutant molecules of the invention may inhibit the functions of activated T cells, such as T lymphocyte proliferation and cytokine secretion, by suppressing T cell responses or by inducing specific tolerance in T cells, or both. Further, the soluble CTLA4 or CTLA4 mtant molecules of this invention, interfering with the CTLA4/CD28/B7 pathway may inhibit T-cell proliferation and/or cytokine secretion, and thus result in reduced tissue destruction and induction of T-cell unresponsiveness or anergy.

The invention further provides methods for inhibiting rejection of organ or tissue transplants in subjects comprising administering an effective amount of at least one soluble CTLA4 or CTLA4 molecule, e.g., L104EA29YIg, to the subject before, during and/or after transplantation. In another embodiment, the method of the invention include administering to a subject at least one soluble CTLA4 or a CTLA4 mutant molecule in combination with at least one other therapeutic agent, including, but not limited to a drug, a toxin, an enzyme, an antibody, or a conjugate.

The organ or tissue transplant can be from any type of organ or tissue amenable to transplantation. In one embodiment, the transplanted tissue can be a pancreatic tissue. In a preferred embodiment, the transplant tissue is pancreatic islet cells. The invention also provides methods for treating type 1 and/or type 2 diabetes in subjects by inhibiting islet cell transplant rejection.

The present invention further provides a method for inhibiting pancreatic islet transplant rejection in a subject, the subject being a recipient of transplant tissue. Typically, in tissue transplants, rejection of the graft is initiated through its recognition as foreign by T cells, followed by an immune response that destroys the graft. Administration of a soluble CTLA4 molecule in the method of this invention inhibits T lymphocyte proliferation and/or cytokine secretion, resulting in reduced tissue destruction and induction of antigen-specific T cell unresponsiveness that may result in long-term graft acceptance, without the need for generalized immunosuppression.

A preferred embodiment of the invention comprises use of the soluble CTLA4 mutant molecule L104EA29YIg to regulate functional CTLA4- and CD28-positive cell interactions with B7-positive cells, to treat immune system diseases such as diabetes and/or to downregulate immune responses. The L104EA29YIg of the invention is a soluble CTLA4 mutant molecule comprising at least the two amino acid changes, the leucine (L) to glutamic acid (E) at position +104 and the alanine (A) to tyrosine (Y) change at position +29. The L104EA29YIg molecule may encompass further mutations beyond the two specified herein.

The method can further comprise administering with the soluble CTLA4 mutant molecules, a base immunosuppressive regimen to the subject. The base immunosuppressive regimen can include (but is not limited to): cyclosporin, azathioprine, methotrexate, cyclophosphamide, lymphocyte immune globulin, anti-CD3 antibodies, Rho (D) immune globulin, adrenocorticosteroids, sulfasalzine, FK-506. methoxsalen, mycophenolate mofetil (CELLCEPT), horse anti-human thymocyte globulin (ATGAM), humanized anti-TAC (HAT), basiliximab (SIMULECT), rabbit anti-human thymocyte globulin (THYMOGLOBULIN), sirolimus, thalidomide, methotrexate, chloroquine, hydroxychloroquine, sulfasalazine, sulphasalazopyrine, leflunomide, gold salts, D-penicillamine, azathioprine, anakinra, infliximab, etanercept, TNFα blockers or a biological agent that targets an inflammatory cytokine. In a preferred embodiment, base immunosuppressive regimen is steroid free. More preferably, the base immunosuppressive regimen comprises rapamycin and anti-human IL-2 R mAb.

An embodiment of the invention comprises use of a molecule to block the interaction between B7 and CTLA4 in conjunction with an immunosuppressive agent to regulate an immune response in order to treat an immune system disease such as diabetes. The molecule used to block the B7/CTLA4 interaction may be a soluble CTLA4 such as CTLA4Ig, CTLA4Ig/CD28Ig or L104EA29YIg, a soluble CD28 such as CD28Ig, a soluble B7 (B7-1 or B7-2) such as B7Ig, anti-CTLA4 monoclonal antibodies, anti-CD28 monoclonal antibodies or anti-B7 monoclonal antibodies.

The subjects treated by the present invention include mammalian subjects, including, human, monkey, ape, dog, cat, cow, horse, goat, pig, rabbit, mouse and rat.

The present invention provides various methods, local or systemic, for administering the therapeutic compositions of the invention such as soluble CTLA4 molecule alone or in conjunction with an immunosuppressive agent and/or other therapeutic drug. The methods include intravenous, intramuscular, intraperitoneal, oral, inhalation and subcutaneous methods, as well as implantable pump, continuous infusion, gene therapy, liposomes, suppositories, topical contact, vesicles, capsules and injection methods. The therapeutic agent, compounded with a carrier, is commonly lyophilized for storage and is reconstituted with water or a buffered solution with a neutral pH (about pH 7-8, e.g., pH 7.5) prior to administration.

As is standard practice in the art, the compositions of the invention may be administered to the subject in any pharmaceutically acceptable form.

In accordance with the practice of the invention, the methods comprise administering to a subject the soluble CTLA4 molecules of the invention to regulate CD28- and/or CTLA4-position cell interactions with B7-positive cells. The B7-positive cells are contacted with an effective amount of the soluble CTLA4 molecules of the invention, or fragments or derivatives thereof, so as to form soluble CTLA4/B7 complexes. The complexes interfere with interaction between endogenous CTLA4 and CD28 molecules with B7 family molecules.

The soluble CTLA4 molecules may be administered to a subject in an amount and for a time (e.g., length of time and/or multiple times) sufficient to block endogenous B7 molecules from binding their respective ligands, in the subject. Blockage of endogenous B7/ligand binding thereby inhibiting interactions between B7-positive cells with CD28- and/or CTLA4-positive cells.

Dosage of a therapeutic agent is dependant upon many factors including, but not limited to, the type of tissue affected, the type of autoimmune disease being treated, the severity of the disease, a subject's health and response to the treatment with the agents. Accordingly, dosages of the agents can vary depending on each subject and the mode of administration. The soluble CTLA4 molecules may be administered in an amount from about 0.1 to 100 mg/kg weight of the patient/day.

The invention also encompasses the use of the compositions of the invention together with other pharmaceutical agents to treat immune system diseases. For example, diabetes may be treated with molecules of the invention in conjunction with, but not limited to, immunosuppressive agents such as corticosteroids, cyclosporin (Mathiesen 1989 Cancer Lett. 44(2):151-156), prednisone, azathioprine, (R. Handschumacher, in: "Drugs Used for Immunosuppression" pages 1264-1276), TNFα blockers or antagonists (New England Journal of Medicine, vol. 340: 253-259, 1999; The Lancet vol. 354: 1932-39, 1999, Annals of Internal Medicine, vol. 130: 478-486), or any other biological agent targeting any inflammatory cytokine, nonsteroidal antiinflammatory drugs/Cox-2 inhibitors, hydroxychloroquine, sulphasalazopryine, gold salts, etanercept, infliximab, rapamycin, mycophenolate mofetil, azathioprine, tacrolismus, basiliximab, cytoxan, interferon beta-1a, interferon beta-1b, glatiramer acetate, mitoxantrone hydrochloride, anakinra and/or other biologics.

The soluble CTLA4 molecules preferably, L104EA29YIg) can also be used in combination with one or more of the following agents to regulate an immune response: soluble gp39 (also known as CD40 ligand (CD40L), CD154, T-BAM, TRAP), soluble CD29, soluble CD40, soluble CD80 (e.g. ATCC 68627), soluble CD86, soluble CD28 (e.g. 68628), soluble CD56, soluble Thy-1, soluble CD3, soluble TCR, soluble VLA-4, soluble VCAM-1, soluble LECAM-1, soluble ELAM-1, soluble CD44, antibodies reactive with gp39 (e.g. ATCC HB-10916, ATCC HB-12055 and ATCC HB-12056), antibodies reactive with CD40 (e.g. ATCC HB-9110), antibodies reactive with B7 (e.g. ATCC HB-253, ATCC CRL-2223, ATCC CRL-2226, ATCC HB-301, ATCC HB-11341, etc), antibodies reactive with CD28 (e.g. ATCC HB-11944 or mAb 9.3 as described by Martin et al (J. Clin. Immun. 4(1):18-22, 1980), antibodies reactive with LFA-1 (e.g. ATCC HB-9579 and ATCC TIB-213), antibodies reactive with LFA-2, antibodies reactive with IL-2, antibodies reactive with IL-12, antibodies reactive with IFN-gamma, antibodies reactive with CD2, antibodies reactive with CD48, antibodies reactive with any ICAM (e.g., ICAM-1 (ATCC CRL-2252), ICAM-2 and ICAM-3), antibodies reactive with CTLA4 (e.g. ATCC HB-304), antibodies reactive with Thy-1, antibodies reactive with CD56, antibodies reactive with CD3, antibodies reactive with CD29, antibodies reactive with TCR, antibodies reactive with VLA-4, antibodies reactive with VCAM-1, antibodies reactive with LECAM-1, antibodies reactive with ELAM-1, antibodies reactive with CD44. In certain embodiments, monoclonal antibodies are preferred. In other embodiments, antibody fragments are preferred. As persons skilled in the art will readily understand, the combination can include the soluble CTLA4 molecules of the invention and one other immunosuppressive agent, the soluble CTLA4 molecules with two other immunosuppressive agents, the soluble CTLA4 molecules with three other immunosuppressive agents, etc. The determination of the optimal combination and dosages can be determined and optimized using methods well known in the art.

Some specific combinations include the following: L104EA29YIg and CD80 monoclonal antibodies (mAbs); L104EA29YIg and CD86 mAbs; L104EA29YIg, CD80 mAbs, and CD86 mAbs; L104EA29YIg and gp39 mAbs; L104EA29YIg and CD40 mAbs; L104EA29YIg and CD28 mAbs; L104EA29YIg, CD80 and CD86 mAbs, and gp39 mAbs; L104EA29YIg, CD80 and CD86 mAbs and CD40 mAbs; and L104EA29YIg, anti-LFA1 mAb, and anti-gp39 mAb. A specific example of a gp39 mAb is MR1. Other combinations will be readily appreciated and understood by persons skilled in the art.

The soluble CTLA4 molecules of the invention, for example L104EA29YIg, may be administered as the sole active ingredient or together with other drugs in immunomodulating regimens or other anti-inflammatory agents e.g., for the treatment or prevention of allo- or xenograft acute or chronic rejection or inflammatory or autoimmune disorders, or to induce tolerance. For example, it may be used in combination with a calcineurin inhibitor, e.g. cyclosporin A or FK506; an immunosuppressive macrolide, e.g. rapamycine or a derivative thereof (e.g. 40-O-(2-hydroxy)ethyl-rapamycin); a lymphocyte homing agent, e.g. FTY720 or an analog thereof; corticosteroids; cyclophosphamide; azathioprene; methotrexate; leflunomide or an analog thereof; mizoribine; mycophenolic acid; mycophenolate mofetil; 15-deoxyspergualine or an analog thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands; or other immunomodulatory compounds, e.g. CTLA4/CD28-Ig, or other adhesion molecule inhibitors, e.g. mAbs or low molecular weight inhibitors including LFA-1 antagonists, Selectin antagonists and VLA-4 antagonists. The compound is particularly useful in combination with a compound that interferes with CD40 and its ligand, e.g. antibodies to CD40 and antibodies to CD40-L.

Where the soluble CTLA4 mutant molecules of the invention are administered in conjunction with other immunosuppressive/immunomodulatory or anti-inflammatory therapy, e.g. as hereinabove specified, dosages of the co-administered immunosuppressive, immunomodulatory or anti-inflammatory compound will of course vary depending on the type of co-drug employed, e.g. whether it is a steroid or a cyclosporin, on the specific drug employed, on the condition being treated and so forth.

In accordance with the foregoing the present invention provides in a yet further aspect methods as defined above comprising co-administration, e.g. concomitantly or in sequence, of a therapeutically effective amount of soluble CTLA4 molecules of the invention, e.g. CTLA4Ig and/or L104EA29YIg, in free form or in pharmaceutically acceptable salt form, and a second drug substance, said second drug substance being an immunosuppressive, immunomodulatory or anti-inflammatory drug, e.g. as indicated above.

Further provided are therapeutic combinations, e.g. a kit, comprising a soluble CTLA4 molecule, in free form or in pharmaceutically acceptable salt form, to be used concomitantly or in sequence with at least one pharmaceutical composition comprising an immunosuppressive, immunomodulatory or anti-inflammatory drug e.g., NSAID, glucocorticoid or corticosteroid. The kit may comprise instructions for its administration. The kits of the invention can be used in any method of the present invention.

In another embodiment of the invention, rejection of tissue or organ transplant is inhibited by administering to a subject soluble CTLA4 and T cell depleted bone marrow cells to the subject. Administration of T cell depleted bone marrow can occur at approximately the same time that the subject receives the tissue or organ transplant or at a different time. Administration of bone marrow at approximately the same time indicates that the bone marrow is administered to the subject as part of the preparation for the procedures for administering the tissue or organ transplant. It is not required that the bone marrow be transplanted at exactly the same time (i.e., within minutes of) as the organ transplant.

In preferred embodiments, the T cell depleted bone marrow is administered before the organ transplant. Particular embodiments include administering the T cell depleted bone marrow within a day, within twelve hours, or within six hours of the solid organ transplant. However, the T cell depleted bone marrow can be administered earlier, so long as the resulting effects of the T cell depleted bone marrow are still achieved in connection with the organ or tissue transplant. In alternative embodiments, it may be desired to administer T cell depleted bone marrow after the organ transplant.

In one embodiment, the method comprises administering a dose of T cell depleted bone marrow cells (tolerizing dose) to a subject, and subsequently administering an additional dose of T cell depleted bone marrow cells (engrafting dose) to the subject. In certain embodiments, the immunosuppressive agent comprises at least one or more types of ligands that interfere with the binding of CD28 antigen to CD80 and/or CD86 antigen. As described supra, the ligand is preferably a mutant CTLA4 molecule, such as L104EA29YIg.

Furthermore, the amount of T cell depleted bone marrow may be determined by routine experimentation and optimized empirically. For example, the amount of T cell depleted bone marrow can be titrated during routine experimentation to determine the amount sufficient to achieve the desired effects.

The methods of the invention may also be practiced by administering, in addition to the soluble CTLA4 mutant molecule, two or more doses of T cell depleted bone marrow to the subject, alone, or in combination with, one or more immunosuppressive agents.

As discussed herein, in the methods of the invention, administration of a soluble CTLA4 or mutant CTLA4 molecule can be accomplished in many different ways including local or systemic administration routes. For example, soluble CTLA4 mutant molecules can be administered intravenously, intramuscularly, or intraperitoneally. Alternatively, mutant CTLA4 may be administered orally or subcutaneously. Other methods of administration will be recognized by those skilled in the art. Similarly, T cell depleted bone marrow can administered in many different ways as known by persons skilled in the art. One example is by way of intravenous infusion.

The immunosuppressive agent(s) can be administered before or after administration of soluble CTLA4 mutant and/or before or after the organ/tissue transplant. Preferably, the bone marrow and immunosuppressive agent are administered before administration of soluble CTLA4 mutant molecule. In one embodiment, a first dose of T cell depleted bone marrow (tolerizing dose) and the immunosuppressive agent is administered at approximately the same time as the organ transplant.

The following examples are presented to illustrate the present invention. The methodology and results may vary depending on the intended goal of treatment and the procedures employed. The examples are not intended in any way to otherwise limit the scope of the invention.

EXAMPLES

Example 1

This example provides a description of the methods used to generate the nucleotide sequences encoding the soluble CTLA4 mutant molecules of the invention. A single-site mutant L104EIg was generated and tested for binding kinetics to CD80 and/or CD86. The L104EIg nucleotide sequence was used as a template to generate the double-site mutant CTLA4 sequence, L104EA29YIg, which was tested for binding kinetics to CD80 and/or CD86.

CTLA4Ig Codon Based Mutagenesis:

A mutagenesis and screening strategy was developed to identify mutant CTLA4Ig molecules that had slower rates of dissociation ("off" rates) from binding CD86 molecules. Single-site mutant nucleotide sequences were generated using CTLA4Ig (U.S. Pat. Nos: 5,844,095; 5,851,795; and 5,885,796; ATCC Accession No. 68629) as a template. Mutagenic oligonucleotide PCR primers were designed for random mutagenesis of a specific cDNA codon by allowing any base at positions 1 and 2 of the codon, but only guanine or thymine at position 3 (XXG/T; also known as NNG/T). In this manner, a specific codon encoding an amino acid could be randomly mutated to code for each of the 20 amino acids. In that regard, XXG/T mutagenesis yields 32 potential codons encoding each of the 20 amino acids. PCR products encoding mutations in close proximity to -M97-G107 of CTLA4Ig (see FIG. 1 or 2), were digested with SacI/XbaI and subcloned into similarly cut CTLA4Ig πLN expression vector. This method was used to generate the single-site CTLA4 mutant molecule L104EIg.

For mutagenesis in proximity to S25-R33 of CTLA4Ig, a silent NheI restriction site was first introduced 5' to this loop, by PCR primer-directed mutagenesis. PCR products were digested with NheI/XbaI and subcloned into similarly cut CTLA4Ig or L104EIg expression vectors. This method was used to generate the double-site CTLA4 mutant molecule L104EA29YIg (FIG. 3). In particular, the nucleic acid molecule encoding the single-site CTLA4 mutant molecule, L104EIg, was used as a template to generate the double-site CTLA4 mutant molecule, L104EA29YIg.

Example 2

The following provides a description of the screening methods used to identify the single-and double-site mutant CTLA4 polypeptides, expressed from the constructs described in Example 1, that exhibited a higher binding avidity for CD80 and CD86 antigens, compared to non-mutated CTLA4Ig molecules.

Current in vitro and in vivo studies indicate that CTLA4Ig by itself is unable to completely block the priming of antigen specific activated T cells. In vitro studies with CTLA4Ig and either monoclonal antibody specific for CD80 or CD86 measuring inhibition of T cell proliferation indicate that anti-CD80 monoclonal antibody did not augment CTLA4Ig inhibition. However, anti-CD86 monoclonal antibody did augment the inhibition, indicating that CTLA4Ig was not as effective at blocking CD86 interactions. These data support earlier findings by Linsley et al. (*Immunity*, (1994), 1:793-801) showing inhibition of CD80-mediated cellular responses required approximately 100 fold lower CTLA4Ig concentrations than for CD86-mediated responses. Based on these findings, it was surmised that soluble CTLA4 mutant molecules having a higher avidity for CD86 than wild type CTLA4 should be better able to block the priming of antigen specific activated cells than CTLA4Ig.

To this end, the soluble CTLA4 mutant molecules described in Example 1 above were screened using a novel screening procedure to identify several mutations in the extracellular domain of CTLA4 that improve binding avidity for CD80 and CD86. This screening strategy provided an effective method to directly identify mutants with apparently slower "off" rates without the need for protein purification or quantitation since "off" rate determination is concentration independent (O'Shannessy et al., (1993) *Anal. Biochem.*, 212:457-468).

COS cells were transfected with individual miniprep purified plasmid DNA and propagated for several days. Three day conditioned culture media was applied to BIAcore biosensor chips (Pharmacia Biotech AB, Uppsala, Sweden) coated with soluble CD80Ig or CD86Ig. The specific binding and dissociation of mutant proteins was measured by surface plasmon resonance (O'Shannessy, D. J., et al., (1993) *Anal. Biochem.* 212:457-468). All experiments were run on BIAcore™ or BIAcore™ 2000 biosensors at 25° C. Ligands were immobilized on research grade NCM5 sensor chips (Pharmacia) using standard N-ethyl-N'-(dimethylaminopropyl)carbodiimidN-hydroxysuccinimide coupling (Johnsson, B., et al. (1991) *Anal. Biochem.* 198: 268-277; Khilko, S. N., et al.(1993) *J. Biol. Chem* 268:5425-15434).

Screening Method

COS cells grown in 24 well tissue culture plates were transiently transfected with DNA encoding mutant CTLA4Ig. Culture media containing secreted soluble mutant CTLA4Ig was collected 3 days later.

Conditioned COS cell culture media was allowed to flow over BIAcore biosensor chips derivatized with CD86Ig or CD80Ig (as described in Greene et al., 1996 *J. Biol. Chem.* 271:26762-26771), and mutant molecules were identified with "off" rates slower than that observed for wild type CTLA4Ig. The cDNAs corresponding to selected media samples were sequenced and DNA was prepared to perform larger scale COS cell transient transfection, from which mutant CTLA4Ig protein was prepared following protein A purification of culture media.

BIAcore analysis conditions and equilibrium binding data analysis were performed as described in J. Greene et al. 1996 *J. Biol. Chem.* 271:26762-26771, and as described herein.

BIAcore Data Analysis

Senosorgram baselines were normalized to zero response units (RU) prior to analysis. Samples were run over mock-derivatized flow cells to determine background response unit (RU) values due to bulk refractive index differences between solutions. Equilibrium dissociation constants ($K_d$) were calculated from plots of $R_{eq}$ versus C, where $R_{eq}$ is the steady-state response minus the response on a mock-derivatized chip, and C is the molar concentration of analyte. Binding curves were analyzed using commercial nonlinear curve-fitting software (Prism, GraphPAD Software).

Experimental data were first fit to a model for a single ligand binding to a single receptor (1-site model, i.e., a simple langmuir system, A+B AB), and equilibrium association constants ($K_d=[A]\cdot[B]\backslash[AB]$) were calculated from the equation $R=R_{max}\cdot C/(K_d+C)$. Subsequently, data were fit to the simplest two-site model of ligand binding (i.e., to a receptor having two non-interacting independent binding sites as described by the equation $R=R_{max1}\cdot C\backslash(K_{d1}+C)+R_{max2}\cdot C\backslash(K_{d2}+C))$.

The goodness-of-fits of these two models were analyzed visually by comparison with experimental data and statistically by an F test of the sums-of-squares. The simpler one-site model was chosen as the best fit, unless the two-site model fit significantly better (p<0.1).

Association and disassociation analyses were performed using BIA evaluation 2.1 Software (Pharmacia). Association rate constants $k_{on}$ were calculated in two ways, assuming both homogenous single-site interactions and parallel two-site interactions. For single-site interactions, $k_{on}$ values were calculated according to the equation $R_t=R_{eq}(1-\exp^{-ks(t-t_0)})$, where $R_t$ is a response at a given time, t; $R_{eq}$ is the steady-state response; $t_0$ is the time at the start of the injection; and $k_s=dR/dt=k_{on} \cdot Ck_{off}$, and where C is a concentration of analyte, calculated in terms of monomeric binding sites. For two-site interactions $k_{on}$ values were calculated according to the equation $R_t=R_{eq1}(1-\exp^{-ks1(t-t_0)})+R_{eq2}(1-\exp^{ks2(t-t_0)})$. For each model, the values of $k_{on}$ were determined from the calculated slope (to about 70% maximal association) of plots of $k_s$ versus C.

Dissociation data were analyzed according to one site (AB=A+B) or two sites (AiBj=Ai+Bj) models, and rate constants ($k_{off}$) were calculated from best fit curves. The binding site model was used except when the residuals were greater than machine background (2-10 RU, according to machine), in which case the two-binding site model was employed. Half-times of receptor occupancy were calculated using the relationship $t_{1/2}=0.693/k_{off}$.

Flow Cytometry:

Murine mAb L307.4 (anti-CD80) was purchased from Becton Dickinson (San Jose, Calif.) and IT2.2 (anti-B7-0 [also known as CD86]), from Pharmingen (San Diego, Calif.). For immunostaining, CD80-positive and/or CD86-positive CHO cells were removed from their culture vessels by incubation in phosphate-buffered saline (PBS) containing 10 mM EDTA. CHO cells (1-10×10⁵) were first incubated with mAbs or immunoglobulin fusion proteins in DMEM containing 10% fetal bovine serum (FBS), then washed and incubated with fluorescein isothiocyanate-conjugated goat anti-mouse or anti-human immunoglobulin second step reagents (Tago, Burlingame, Calif.). Cells were given a final wash and analyzed on a FACScan (Becton Dickinson).

SDS-PAGE and Size Exclusion Chromatogragphy

SDS-PAGE was performed on Tris/glycine 4-20% acrylamide gels (Novex, San Diego, Calif.). Analytical gels were stained with Coomassie Blue, and images of wet gels were obtained by digital scanning. CTLA4Ig (25 µg) and L104EA29YIg (25 µg) were analyzed by size exclusion chromatography using a TSK-GEL G300 $SW_{XL}$ column (7.8×300 mm, Tosohaas, Montgomeryville, Pa.) equilibrated in phosphate buffered saline containing 0.02% $NAN_3$ at a flow rate of 1.0 ml/min.

$CTLA4X_{C102S}$ and $L104EA29YX_{C120S}$.

Single chain $CTLA4X_{C120S}$ was prepared as previously described (Linsley et al., (1995) J. Biol. Chem., 270:15417-15424). Briefly, an oncostatin M CTLA4 (OMCTLA4) expression plasmid was used as a template, the forward primer, GAGGTGATAAAGCTTCACCAATGGGTGTACTGCTCACACAG (SEQ ID NO.: 17) was chosen to match sequences in the vector; and the reverse primer, GTGGTGTATTGGTCTAGATCAATCAGAATCTGGGCACGGTTC (SEQ ID NO.: 18) corresponded to the last seven amino acids (i.e. amino acids 118-124) in the extracellular domain of CTLA4, and contained a restriction enzyme site, and a stop codon (TGA). The reverse primer specified a C120S (cysteine to serine at position 120) mutation. In particular, the nucleotide sequence GCA (nucleotides 34-36) of the reverse primer shown above is replaced with one of the following nucleotide sequences: AGA, GGA, TGA, CGA, ACT, or GCT. As persons skilled in the art will understand, the nucleotide sequence GCA is a reversed complementary sequence of the codon TGC for cysteine. Similarly, the nucleotide sequences AGA, GGA, TGA, CGA, ACT, or GCT are the reversed complementary sequences of the codons for serine. Polymerase chain reaction products were digested with HindIII/XbaI and directionally subcloned into the expression vector πLN (Bristol-Myers Squibb Company, Princeton, N.J.). $L104EA29YX_{C120S}$ was prepared in an identical manner. Each construct was verified by DNA sequencing.

Identification and Biochemical Characterization of High Avidity Mutants

Twenty four amino acids were chosen for mutagenesis and the resulting ~2300 mutant proteins assayed for CD86Ig binding by surface plasmon resonance (SPR; as described, supra). The predominant effects of mutagenesis at each site are summarized in Table II. Random mutagenesis of some amino acids in the S25-R33 apparently did not alter ligand binding. Mutagenesis of E31 and R33 and residues M97-Y102 apparently resulted in reduced ligand binding. Mutagenesis of residues, S25, A29, and T30, K93, L96, Y103, L104, and G105, resulted in proteins with slow "on" and/or slow "off" rates. These results confirm previous findings that residues in the S25-R33 region, and residues in or near M97-Y102 influence ligand binding (Peach et al., (1994) J. Exp. Med., 180:2049-2058.

Mutagenesis of sites S25, T30, K93, L96, Y103, and G105 resulted in the identification of some mutant proteins that had slower "off" rates from CD86Ig. However, in these instances, the slow "off" rate was compromised by a slow "on" rate which resulted in mutant proteins with an overall avidity for CD86Ig that was apparently similar to that seen with wild type CTLA4Ig. In addition, mutagenesis of K93 resulted in significant aggregation which may have been responsible for the kinetic changes observed.

Random mutagenesis of L104 followed by COS cell transfection and screening by SPR of culture media samples over immobilized CD86Ig yielded six media samples containing mutant proteins with approximately 2-fold slower "off" rates than wild type CTLA4Ig. When the corresponding cDNA of these mutants were sequenced, each was found to encode a leucine to glutamic acid mutation (L104E). Apparently, substitution of leucine 104 to aspartic acid (L104D) did not affect CD86Ig binding.

Figure 14A:
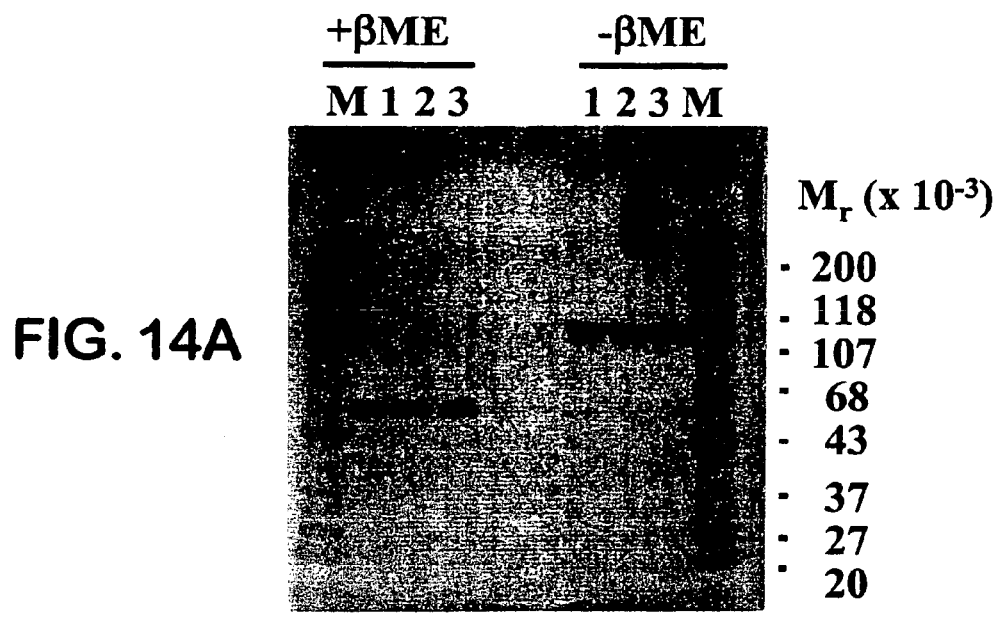
FIGS. 14A-C are an SDS gel (FIG. 14A) for CTLA4Ig (lane 1), L104EIg (lane 2), and L104EA29YIg (lane 3A); and size exclusion chromatographs of CTLA4Ig (FIG. 14B) and L104EA29YIg (FIG. 14C).
Figure 14B:
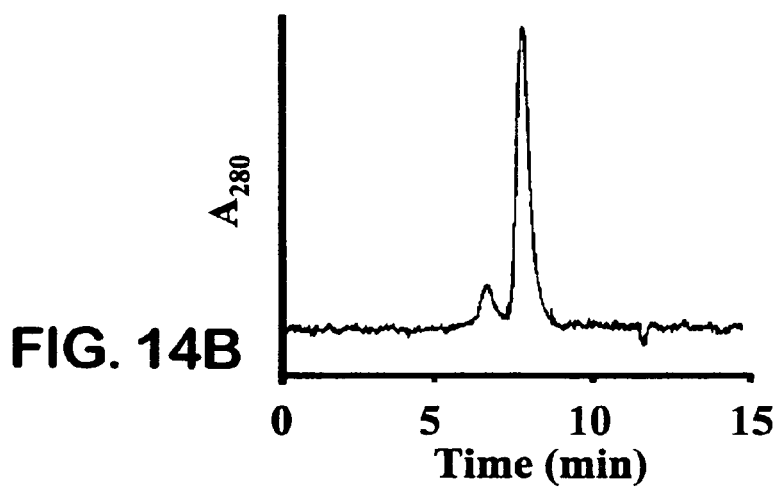
Figure 14C:
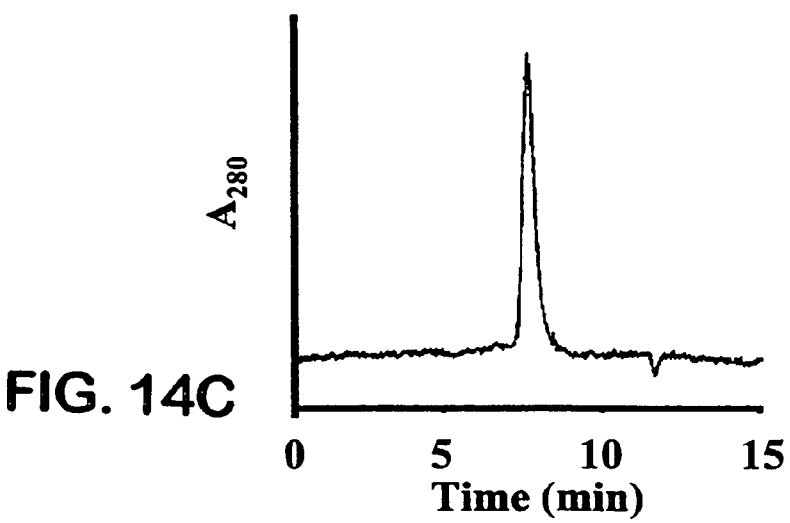

Mutagenesis was then repeated at each site listed in Table II, this time using L104E as the PCR template instead of wild type CTLA4Ig, as described above. SPR analysis, again using immobilized CD86Ig, identified six culture media samples from mutagenesis of alanine 29 with proteins having approximately 4-fold slower "off" rates than wild type CTLA4Ig. The two slowest were tyrosine substitutions (L104EA29Y), two were leucine (L104EA29L), one was tryptophan (L104EA29W), and one was threonine (L104EA29T). Apparently, no slow "off" rate mutants were identifed when alanine 29 was randomly mutated, alone, in wild type CTLA4Ig.

The relative molecular mass and state of aggregration of purified L104E and L104EA29YIg was assessed by SDS-PAGE and size exclusion chromatography. L104EA29YIg (~1 μg; lane 3) and L104EIg (~1 μg; lane 2) apparently had the same electrophoretic mobility as CTLA4Ig (~1 μg; lane 1) under reducing (~50 kDa; +βME; plus 2-mercaptoethanol) and non-reducing (~100 kDa; −ββME) conditions (FIG. 14A). Size exclusion chromatography demonstrated that L104EA29YIg (FIG. 14C) apparently had the same mobility as dimeric CTLA4Ig (FIG. 14B). The major peaks represent protein dimer while the faster eluting minor peak in FIG. 14B represents higher molecular weight aggregates. Approximately 5.0% of CTLA4Ig was present as higher molecular weight aggregates but there was no evidence of aggregation of L104EA29YIg or L104EIg. Therefore, the stronger binding to CD86Ig seen with L104EIg and L104EA29YIg could not be attributed to aggregation induced by mutagenesis.

Equilibrium and Kinetic Binding Analysis

Equilibrium and kinetic binding analysis was performed on protein A purified CTLA4Ig, L104EIg, and L104EA29YIg using surface plasmon resonance (SPR). The results are shown in Table I. Observed equilibrium dissociation constants ($K_d$; Table I) were calculated from binding curves generated over a range of concentrations (5.0-200 nM). L104EA29YIg binds more strongly to CD86Ig than does L104EIg or CTLA4Ig. The lower $K_d$ of L104EA29YIg (3.21 nM) than L104EIg (6.06 nM) or CTLA4Ig (13.9 nM) indicates higher binding avidity of L104EA29YIg to CD86Ig. The lower $K_d$ of L104EA29YIg (3.66 nM) than L104EIg (4.47 nM) or CTLA4Ig (6.51 nM) indicates higher binding avidity of L104EA29YIg to CD80Ig.

Kinetic binding analysis revealed that the comparative "on" rates for CTLA4Ig, L104EIg, and L104EA29YIg binding to CD80 were similar, as were the "on" rates for CD86Ig (Table I). However, "off" rates for these molecules were not equivalent (Table I). Compared to CTLA4Ig, L104EA29YIg had approximately 2-fold slower "off" rate from CD80Ig, and approximately 4-fold slower "off" rate from CD86Ig. L104E had "off" rates intermediate between L104EA29YIg and CTLA4Ig. Since the introduction of these mutations did not significantly affect "on" rates, the increase in avidity for CD80Ig and CD86Ig observed with L104EA29YIg was likely primarily due to a decrease in "off" rates.

To determine whether the increase in avidity of L104EA29YIg for CD86Ig and CD80Ig was due to the mutations affecting the way each monomer associated as a dimer, or whether there were avidity enhancing structural changes introduced into each monomer, single chain constructs of CTLA4 and L104EA29Y extracellular domains were prepared following mutagenesis of cysteine 120 to serine as described supra, and by Linsley et al., (1995) *J. Biol. Chem.*, 270:15417-15424. The purified proteins CTLA4X$_{C120S}$ and L104EA29YX$_{C120S}$ were shown to be monomeric by gel permeation chromatography (Linsley et al., (1995), supra), before their ligand binding properties were analyzed by SPR. Results showed that binding affinity of both monomeric proteins for CD86Ig was approximately 35-80-fold less than that seen for their respective dimers (Table I). This supports previously published data establishing that dimerization of CTLA4 was required for high avidity ligand binding (Greene et al., (1996) *J. Biol. Chem.*, 271:26762-26771).

L104EA29YX$_{C120S}$ bound with approximately 2-fold higher affinity than CTLA4X$_{120S}$ to both CD80Ig and CD86Ig. The increased affinity was due to approximately 3-fold slower rate of dissociation from both ligands. Therefore, stronger ligand binding by L104EA29Y was most likely due to avidity enhancing structural changes that had been introduced into each monomeric chain rather than alterations in which the molecule dimerized.

Location and Structural Analysis of Avidity Enhancing Mutations

Figure 15:
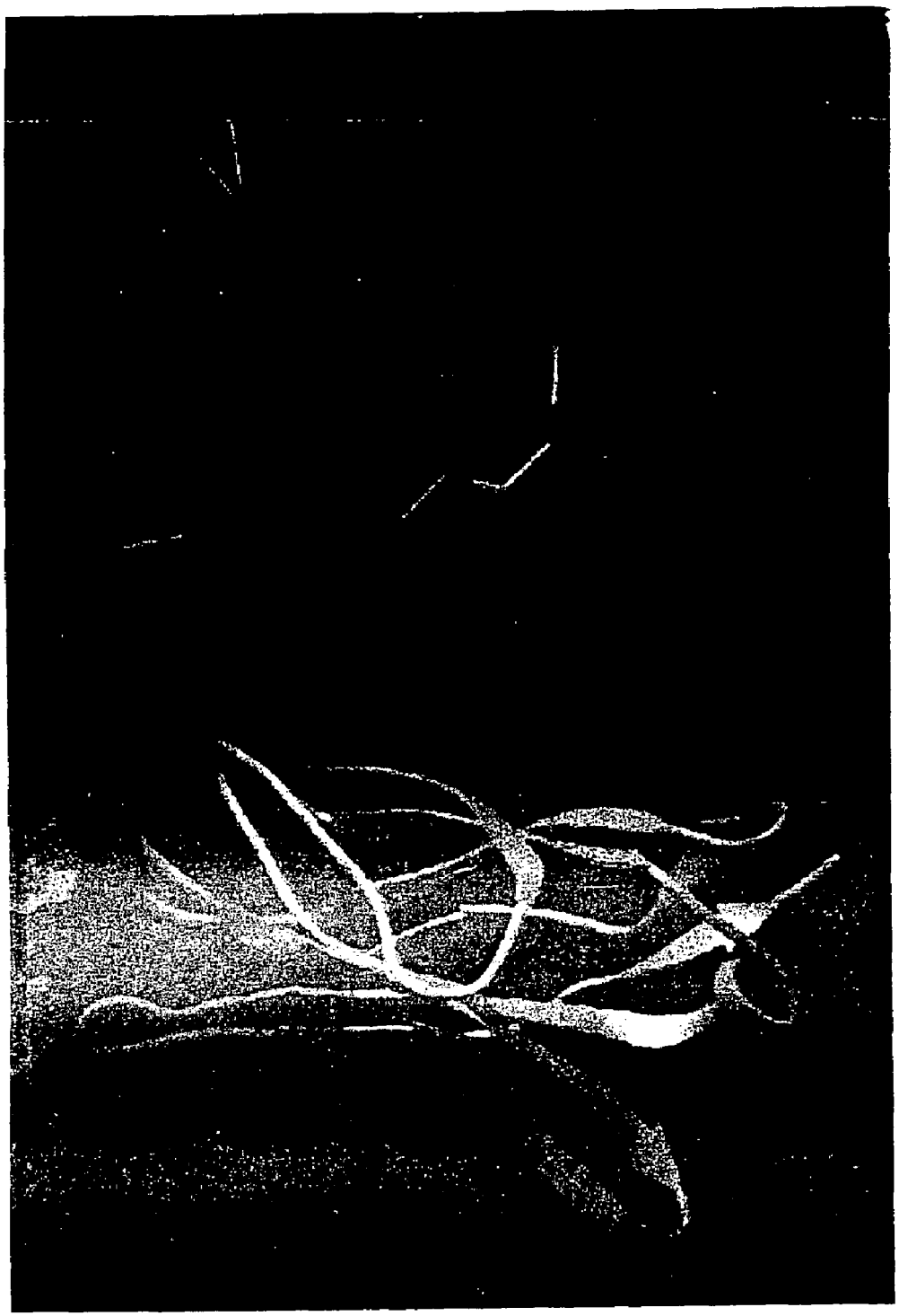
FIGS. 15A and 15B illustrate a ribbon diagram of the CTLA4 extracellular Ig V-like fold generated from the solution structure determined by NMR spectroscopy.

The solution structure of the extracellular IgV-like domain of CTLA4 has recently been determined by NMR spectroscopy (Metzler et al., (1997) *Nature Struct. Biol.*, 4:527-531. This allowed accurate location of leucine 104 and alanine 29 in the three dimensional fold (FIG. 15A-B). Leucine 104 is situated near the highly conserved MYPPPY amino acid sequence. Alanine 29 is situated near the C-terminal end of the S25-R33 region, which is spatially adjacent to the MYPPPY region. While there is significant interaction between residues at the base of these two regions, there is apparently no direct interaction between L104 and A29 although they both comprise part of a contiguous hydrophobic core in the protein. The structural consequences of the two avidity enhancing mutants were assessed by modeling. The A29Y mutation can be easily accommodated in the cleft between the S25-R33 region and the MYPPPY region, and may serve to stabilize the conformation of the MYPPPY region. In wild type CTLA4, L104 forms extensive hydrophobic interactions with L96 and V94 near the MYPPPY region. It is highly unlikely that the glutamic acid mutation adopts a conformation similar to that of L104 for two reasons. First, there is insufficient space to accommodate the longer glutamic acid side chain in the structure without significant perturbation to the S25-R33 region. Second, the energetic costs of burying the negative charge of the glutamic acid side chain in the hydrophobic region would be large. Instead, modeling studies predict that the glutamic acid side chain flips out on to the surface where its charge can be stabilized by solvation. Such a conformational change can easily be accommodated by G105, with minimal distortion to other residues in the regions.

Binding of High Avidity Mutants to CHO Cells Expressing CD80 or CD86

FACS analysis (FIG. 9) of CTLA4Ig and mutant molecules binding to stably transfected CD80+ and CD86+CHO cells was performed as described herein. CD80-positive and CD86-positive CHO cells were incubated with increasing concentrations of CTLA4Ig, L104EA29YIg, or L104EIg, and then washed. Bound immunoglobulin fusion protein was detected using fluorescein isothiocyanate-conjugated goat anti-human immunoglobulin.

As shown in FIG. 9, CD80-positive or CD86-positive CHO cells ($1.5 \times 10^5$) were incubated with the indicated concentrations of CTLA4Ig (closed squares), L104EA29YIg (circles), or L104EIg (triangles) for 2 hr. at 23° C., washed, and incubated with fluorescein isothiocyanate-conjugated goat anti-human immunoglobulin antibody. Binding on a total of 5,000 viable cells was analyzed (single determination) on a FACScan, and mean fluorescence intensity (MFI) was determined from data histograms using PC-LYSYS. Data were corrected for background fluorescence measured on cells incubated with second step reagent only (MFI=7). Control L6 mAb (80 μg/ml) gave MFI<30. These results are representative of four independent experiments.

Figure 9A:
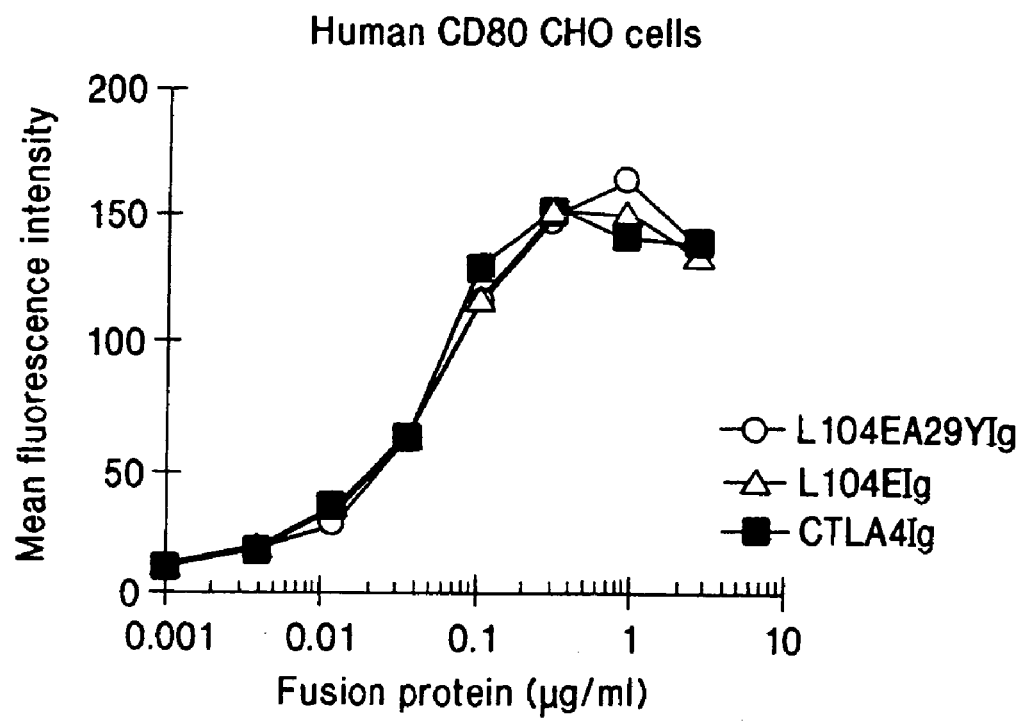
FIGS. 9A & 9B illustrate data from FACS assays showing binding of L104EA29YIg, L104EIg, and CTLA4Ig to human CD80- or CD86-transfected CHO cells as described in Example 2, infra.
Figure 9B:
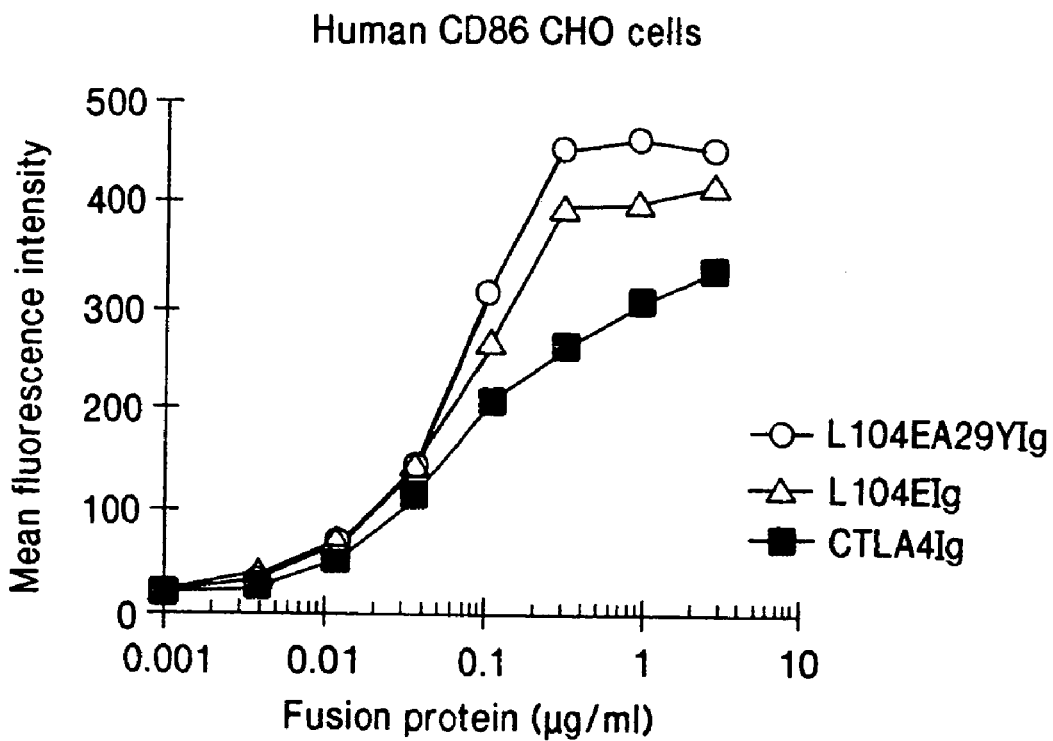

Binding of L104EA29YIg, L104EIg, and CTLA4Ig to human CD80-transfected CHO cells is approximately equivalent (FIG. 9A). L104EA29YIg and L104EIg bind more strongly to CHO cells stably transfected with human CD86 than does CTLA4Ig (FIG. 9B).

Figure 10A:
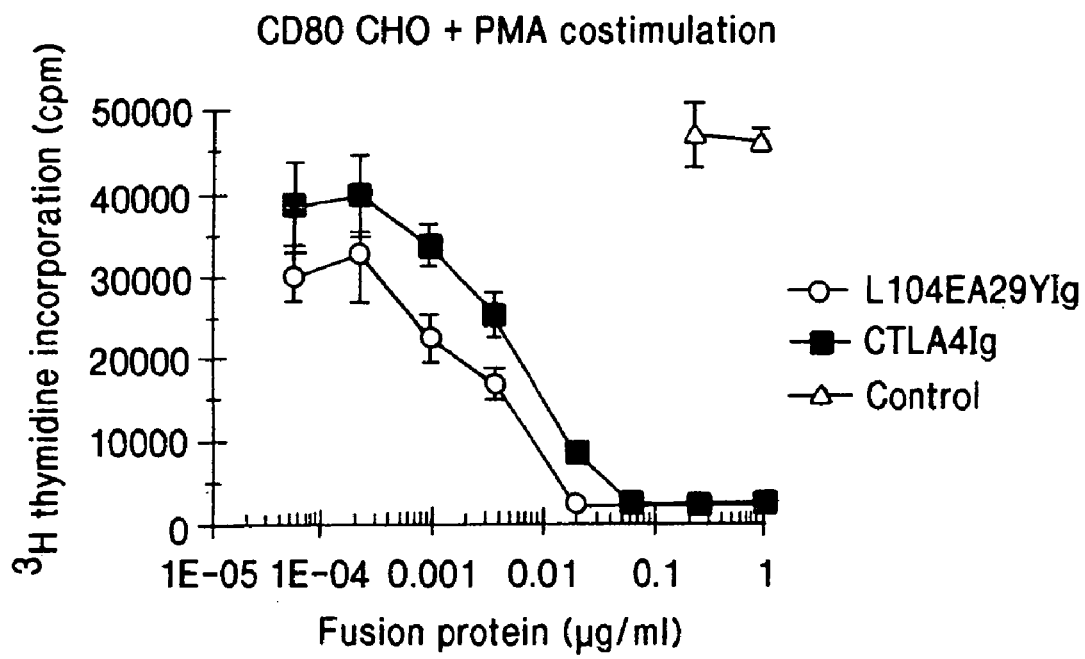
FIGS. 10A & 10B depicts inhibition of proliferation of CD80-positive and CD86-positive CHO cells as described in Example 2, infra.
Figure 10B:
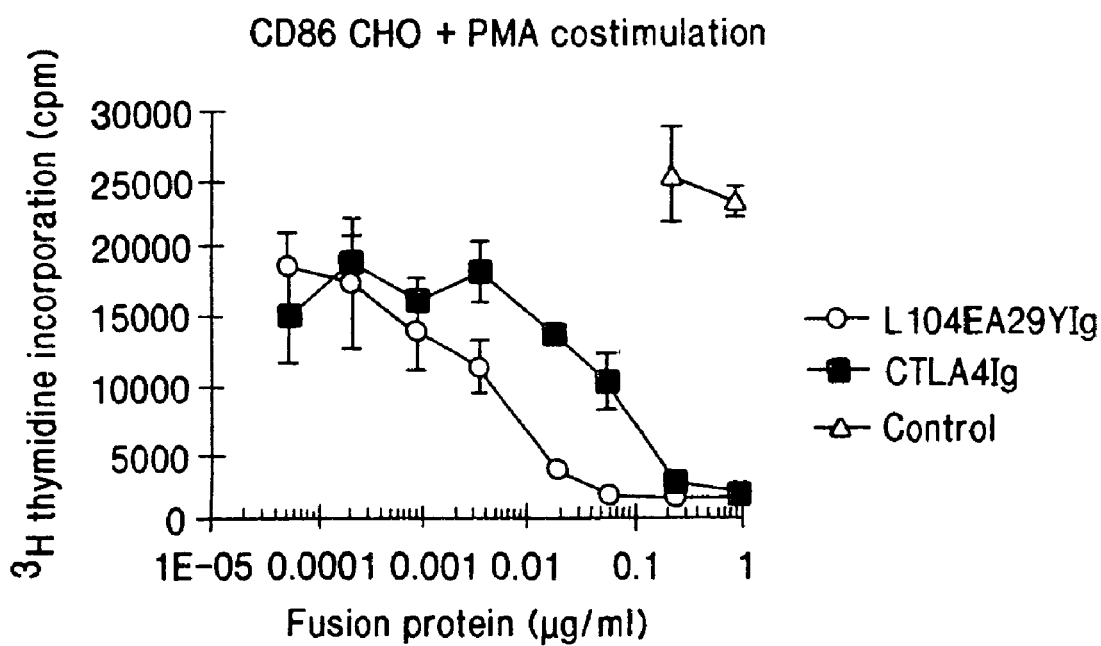

Functional Assays:

Human CD4-positive T cells were isolated by immunomagnetic negative selection (Linsley et al., (1992) *J. Exp. Med.* 176:1595-1604). Isolated CD4-positive T cells were stimulated with phorbal myristate acetate (PMA) plus CD80-positive or CD86-positive CHO cells in the presence of titrating concentrations of inhibitor. CD4-positive T cells (8-10×10$^4$/well) were cultured in the presence of 1 nM PMA with or without irradiated CHO cell stimulators. Proliferative responses were measured by the addition of 1 μCi/well of [3H]thymidine during the final 7 hours of a 72 hour culture. Inhibition of PMA plus CD80-positive CHO, or CD86-positive CHO, stimulated T cells by L104EA29YIg and CTLA4Ig was performed. The results are shown in FIG. 10. L104EA29YIg inhibits proliferation of CD80-positive PMA treated CHO cells more than CTLA4Ig (FIG. 10A). L104EA29YIg is also more effective than CTLA4Ig at inhibiting proliferation of CD86-positive PMA treated CHO cells (FIG. 10B). Therefore, L104EA29YIg is a more potent inhibitor of both CD80- and CD86-mediated costimulation of T cells.

FIG. 11 shows inhibition by L104EA29YIg and CTLA4Ig of allostimulated human T cells prepared above, and further allostimulated with a human B lymphoblastoid cell line (LCL) called PM that expressed CD80 and CD86 (T cells at 3.0×10$^4$/well and PM at 8.0×10$^3$/well). Primary allostimulation occurred for 6 days, then the cells were pulsed with $^3$H-thymidine for 7 hours, before incorporation of radiolabel was determined.

Figure 11A:
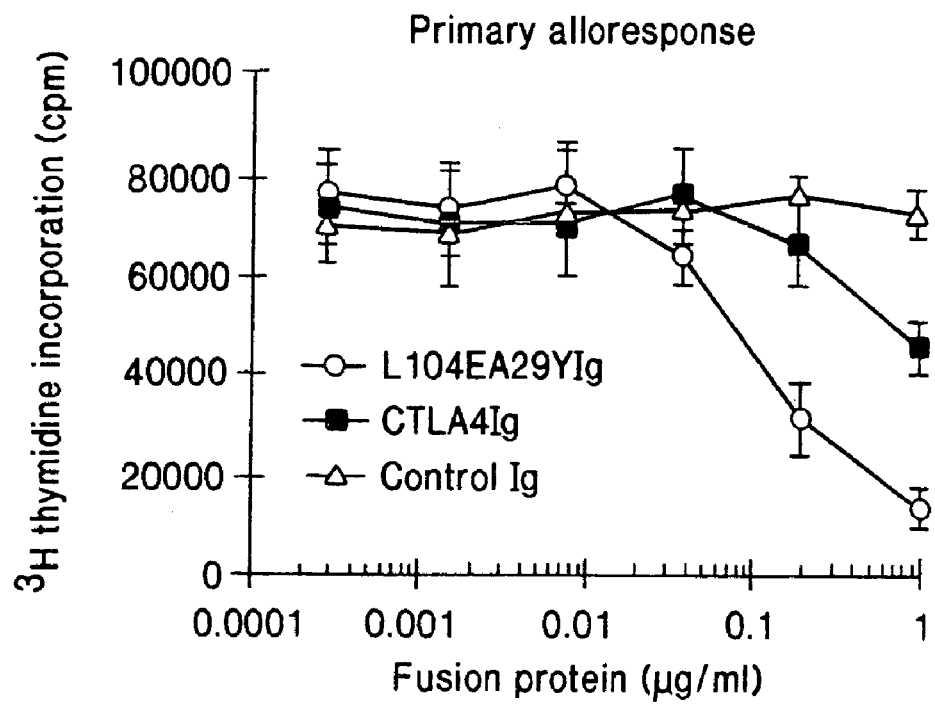
FIGS. 11A & 11B shows that L104EA29YIg is more effective than CTLA4Ig at inhibiting proliferation of primary and secondary allostimulated T cells as described in Example 2, infra.
Figure 11B:
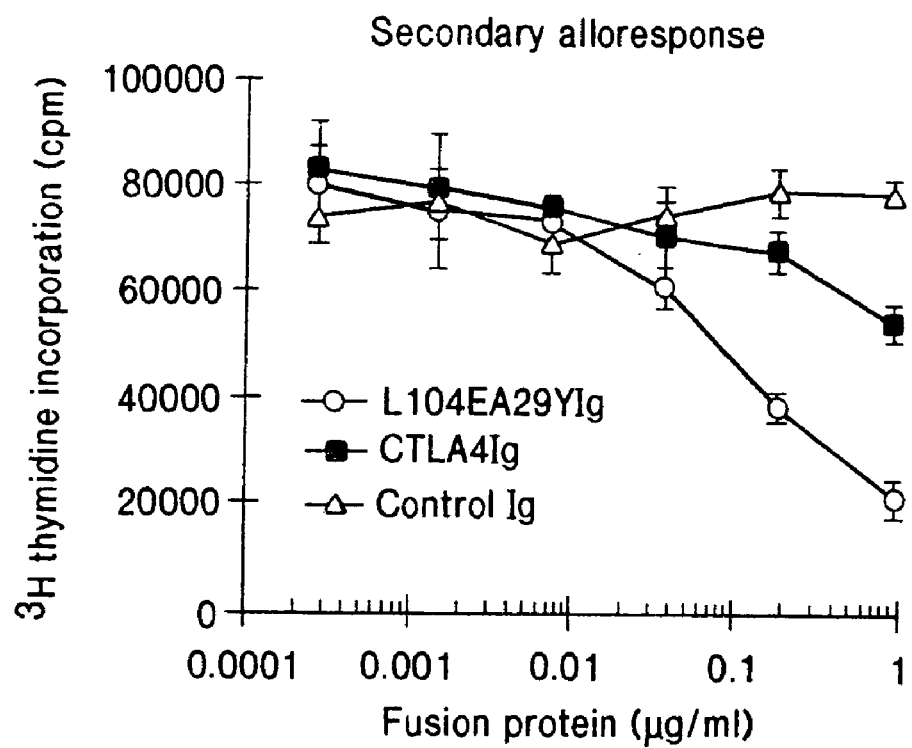

Secondary allostimulation was performed as follows. Seven day primary allostimulated T cells were harvested over lymphocyte separation medium (LSM) (ICN, Aurora, Ohio) and rested for 24 hours. T cells were then restimulated (secondary), in the presence of titrating amounts of CTLA4Ig or L104EA29YIg, by adding PM in the same ratio as above. Stimulation occurred for 3 days, then the cells were pulsed with radiolabel and harvested as above. The effect of L104EA29YIg on primary allostimulated T cells is shown in FIG. 11A. The effect of L104EA29YIg on secondary allostimulated T cells is shown in FIG. 11B. L104EA29YIg inhibits both primary and secondary T cell proliferative responses better than CTLA4Ig.

Figure 12A:
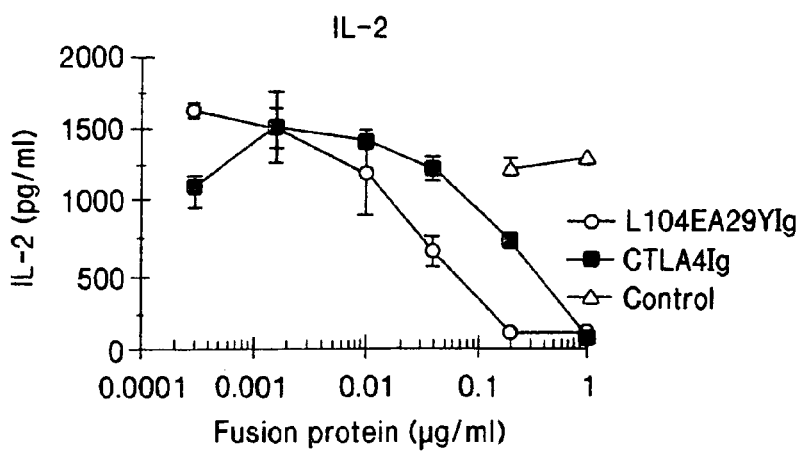
FIGS. 12A-C illustrate that L104EA29YIg is more effective than CTLA4Ig at inhibiting IL-2 (FIG. 12A), IL-4 (FIG. 12B), and γ-interferon (FIG. 12C) cytokine production of allostimulated human T cells as described in Example 2, infra.
Figure 12B:
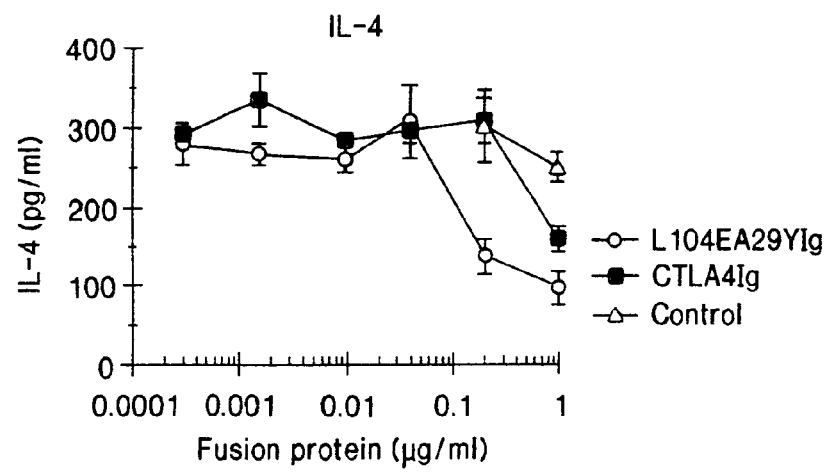
Figure 12C:
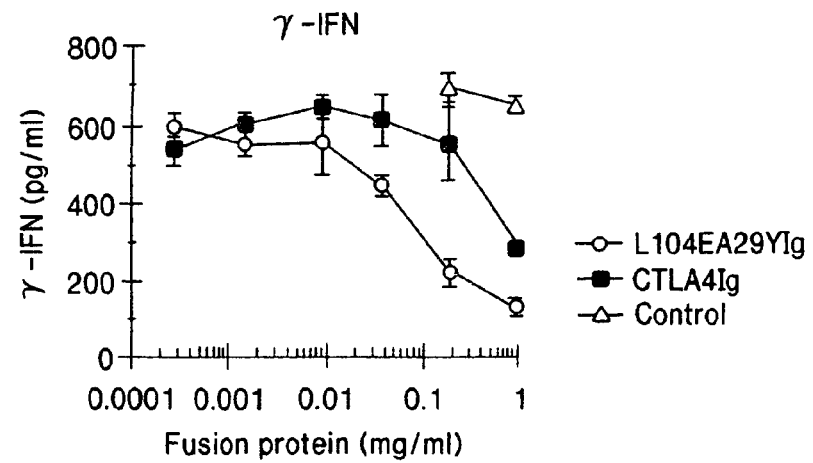

To measure cytokine production (FIG. 12), duplicate secondary allostimulation plates were set up. After 3 days, culture media was assayed using ELISA kits (Biosource, Camarillo, Calif.) using conditions recommended by the manufacturer. L104EA29YIg was found to be more potent than CTLA4Ig at blocking T cell IL-2, IL-4, and γ-IFN cytokine production following a secondary allogeneic stimulus (FIGS. 12A-C).

Figure 13:
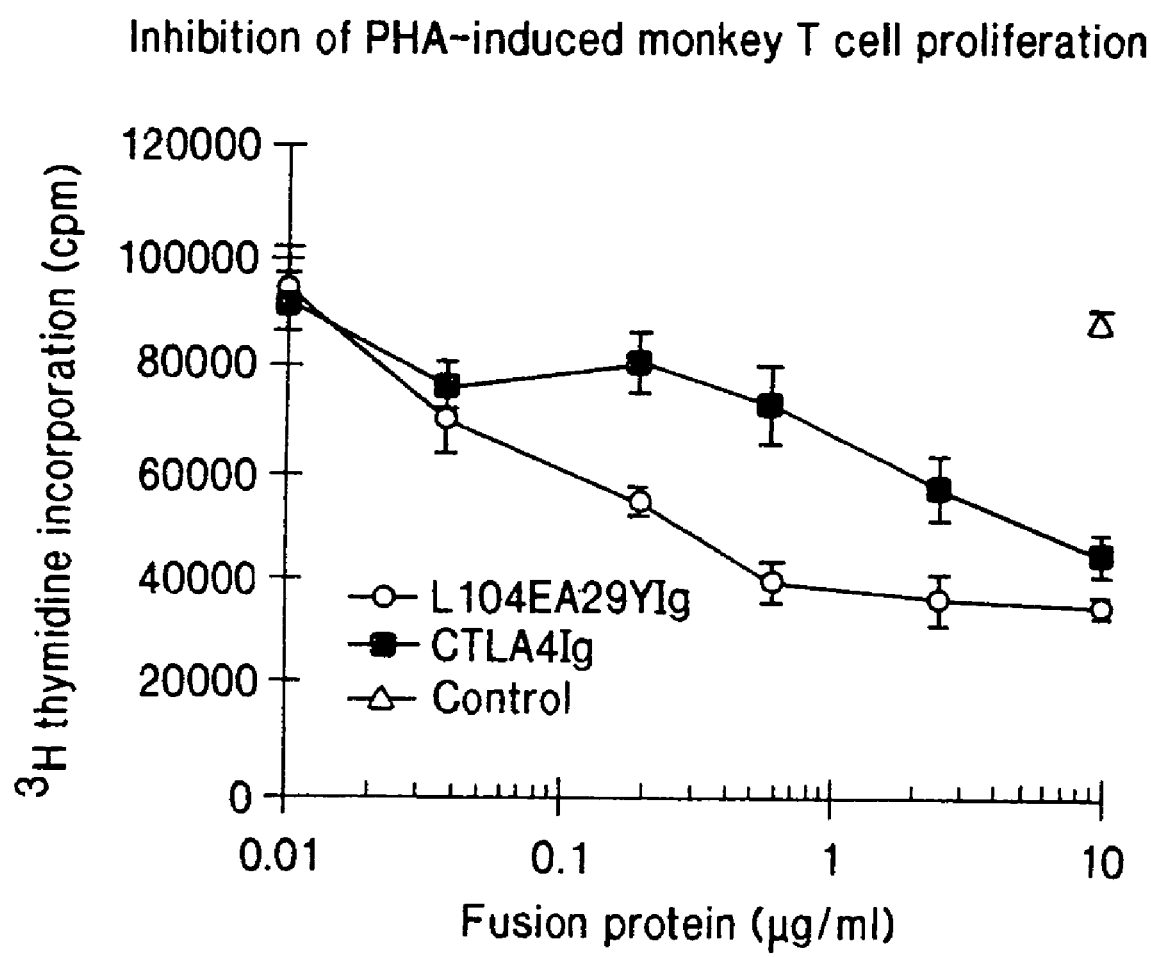
FIG. 13 demonstrates that L104EA29YIg is more effective than CTLA4Ig at inhibiting proliferation of phytohemaglutinin-(PHA) stimulated monkey T cells as described in Example 2, infra.

The effects of L104EA29YIg and CTLA4Ig on monkey mixed lymphocyte response (MLR) are shown in FIG. 13. Peripheral blood mononuclear cells (PBMC'S; 3.5×10$^4$ cells/well from each monkey) from 2 monkeys were purified over lymphocyte separation medium (LSM) and mixed with 2 μg/ml phytohemaglutinin (PHA). The cells were stimulated 3 days then pulsed with radiolabel 16 hours before harvesting. L104EA29YIg inhibited monkey T cell proliferation better than CTLA4Ig.

TABLE I

Equilibrium and apparent kinetic constants are given in the following table (values are means ± standard deviation from three different experiments):

| Immobilized Protein | Analyte | $k_{on}$ (× 10$^5$) $M^{-1} S^{-1}$ | $k_{off}$ (× 10$^{-3}$) $S^{-1}$ | $K_d$ nM |
|---|---|---|---|---|
| CD80Ig | CTLA4Ig | 3.44 ± 0.29 | 2.21 ± 0.18 | 6.51 ± 1.08 |
| CD80Ig | L104EIg | 3.02 ± 0.05 | 1.35 ± 0.08 | 4.47 ± 0.36 |
| CD80Ig | L104EA29YIg | 2.96 ± 0.20 | 1.08 ± 0.05 | 3.66 ± 0.41 |
| CD80Ig | CTLA4X$_{C120S}$ | 12.0 ± 1.0 | 230 ± 10 | 195 ± 25 |
| CD80Ig | L104EA29YX$_{C120S}$ | 8.3 ± 0.26 | 71 ± 5 | 85.0 ± 2.5 |
| CD86Ig | CTLA4Ig | 5.95 ± 0.57 | 8.16 ± 0.52 | 13.9 ± 2.27 |
| CD86Ig | L104EIg | 7.03 ± 0.22 | 4.26 ± 0.11 | 6.06 ± 0.05 |
| CD86Ig | L104EA29YIg | 6.42 ± 0.40 | 2.06 ± 0.03 | 3.21 ± 0.23 |
| CD86Ig | CTLA4X$_{C120S}$ | 16.5 ± 0.5 | 840 ± 55 | 511 ± 17 |
| CD86Ig | L104EA29YX$_{C120S}$ | 11.4 ± 1.6 | 300 ± 10 | 267 ± 29 |

TABLE II

The effect on CD86Ig binding by mutagenesis of CTLA4Ig at the sites listed was determined by SPR, described supra. The predominant effect is indicated with a "+" sign.

| | Effects of Mutagenesis | | |
|---|---|---|---|
| Mutagenesis Site | No Apparent Effect | Slow "on" rate/slow "off rate | Reduced ligand binding |
| S25 | | + | |
| P26 | + | | |
| G27 | | + | |
| K28 | + | | |
| A29 | | + | |
| T30 | | + | |
| E31 | | | + |
| R33 | | | + |
| K93 | | + | |
| L96 | | + | |
| M97 | | | + |
| Y98 | | | + |
| P99 | | | + |
| P100 | | | + |
| P101 | | | + |
| Y102 | | | + |
| Y103 | | + | |
| L104 | | + | |
| G105 | | + | |
| I106 | + | | |
| G107 | + | | |
| Q111 | + | | |
| Y113 | + | | |
| I115 | + | | |

Example 3

This example provides a description of donor pancreatectomy and islet isolation, and islet transplant procedures in an animal model.

Materials and Method:

Animals. Captive bred adolescent male rhesus monkeys (Macaca mulatta) (~4-20 kg) were used as recipients and donors. The absence of preformed donor-specific antibodies in the recipient was confirmed prior to transplant. All potential donors and recipients were tested for anti-CMV antibodies and only animals that were sero-positive for CMV were used as recipients.

Donor Pancreatectomy and Islet Isolation. The donor pancreatectomy was performed one day prior to transplantation. The procedure was performed under general anesthesia (a combination of parenteral ketamine and Isolflurane by inhalation) through a midline abdominal incision. The splenorenal and splenocolic ligaments were divided so that the spleen, together with the tail of the pancreas was mobilized. The head of the pancreas and second portion of the duodenum were mobilized following Kocher maneuver. After administration of heparin (200 U/kg), the aorta was cannulated just above its bifurcation and the animal was exsanguinated. Cold slush was immediately placed in the lesser sac and behind the body of the pancreas. The body and neck of the pancreas were carefully excised by sharp dissection taking care not to violate the pancreatic capsule. The common bile duct, the main and accessory pancreatic ducts were identified and ligated, and the head of the pancreas dissected from the second portion of the duodenum.

Rhesus monkey islet isolation was completed via minor modifications of the automated method for human islet isolation (Ricordi, (1988) Diabetes, 37: 413; Ranuncoli, (2000) Cell Transplant 9: 409) by using Liberase (Roche/Boehringer Mannheim, Indpls, Ind.) at a concentration of 0.47-0.71 mg/ml. A three layer, discontinuous Euroficoll gradient (densities 1.108, 1.097, 1.037; Meditech, Herndon, Va.) and a Cobe 2991 blood cell processor (Gambro, Lakewood, Colo.) were used for purification of islets from the pancreatic digest. Samples of the final islet preparation were stained with dithizone (Sigma, St. Louis, Mo.), and the preparation was assessed by counting the number of islets in each of the following size ranges: 50-100, 100-150, 150-200, 200-250, 250-300, 300-350, and 350-400 µm. The data were mathematically converted to determine the number of islets with an average diameter of 150 µm and were expressed as islet equivalents (IEQ) (Ricordi C. et al., *Acta Diabetol Lat* 27:185-195, 1990).

Recipient Pancreatectomy and Intrahepatic Islet Cell Transplantation. Total pancreatectomy, without duodenectomy or splenectomy, was performed at least one week prior to transplant. The tail and body of the pancreas were dissected along the splenic artery and vein, which were carefully preserved by ligating and dividing only pancreatic branches. The inferior mesenteric and middle colic veins were identified and preserved during dissection of the body of the pancreas. The portal and superior mesenteric veins were recognized and pancreatic veins were ligated and divided.

The duodenum was mobilized and branches of the pancreaticoduodenal vessels that entered the pancreas were ligated and divided, leaving the duodenal branches intact. The common bile duct was identified and preserved during blunt dissection between the head of the pancreas and the c-loop of the duodenum. The main and accessory pancreatic ducts were ligated, divided, and the pancreas was removed from the abdominal cavity. All animals underwent intravenous glucose tolerance test to evaluate the efficacy of the pancreatectomy procedure. All were documented to be c-peptide negative prior to islet transplantation.

Overnight cultured islets were washed in transplant media, consisting of RPMI medium 1640 (Mediatech) supplemented with 2.5% human serum albumin, and counted to determine the number of IEQ. Islets were then pelleted and resuspended in 20 ml of transplant media supplemented with 200 units of heparin. Intra-hepatic islet transplantation was performed via gravity drainage of islets into a sigmoid or branch of the left colic vein draining into the portal vein through a 22-gauge intravenous catheter.

Blood glucose monitoring, insulin adminstration, and definition of rejection. Fasting and post-prandial blood glucose levels were monitored twice daily (pre-breakfast and post-lunch) via ear-stick, followed by blood testing with a glucometer elite (Bayer, Elkhart, Ind.). Insulin (NPH, Ultralente; Eli Lilly, Indianpolis, Ind. was administered three times daily in attempt to maintain fasting blood glucose <300 mg/dl in pretransplant pancreatectomized animals or in those who had rejected their allografts.

Experimental groups and immunosuppressive protocols. Two treatment protocols were tested: (1) Edmonton protocol—using Tacrolimus, Sirolimus, and anti-IL-2R mAb (Shapiro, A. M. J. et al, (2000), N. Eng. J. Med., 343: 230-238) and (2) L104EA29Y-Edmonton protocol—using L104EA29YIg, Sirolimus, and anti-IL-2R mAb. The control group included recipients treated with 'base immunosuppressive regimen" having rapamycin and anti-IL-2R alone. Tacrolimus was given 0.05 mg/kg bid POD 0-14 (target levels 5-8) and 0.06 mg/kg daily (target levels 3-5) POD 15-120. L104EA29YIg was administered intravenously intra-operatively (10 mg/kg) and on post-operative days 4 (15 mg/kg), 14, 28, 42, 56, 70, 84, 98, 112, 126 (20 mg/kg) to maintain serum trough levels greater than 30 µg/ml. The chimeric anti-human IL-2R mAb (0.3 mg/kg iv), was administered intra-operatively and on POD 4. Sirolimus (Rapamune®) was administered orally 1.25 mg/kg bid (target levels 10-15) POD 0-50, 1 mg/kg bid (target levels 7-10) POD 50-100, and then tapered to terminate dosing by POD130. Sirolimus (Rapamune®) and Tacrolimus (Prograf®) were purchased from the Emory University Hospital Pharmacy. The chimeric anti-human IL-2R mAb (Simulect®) was provided by Novartis Pharma AG (Basel, Switzerland).

Necropsy. All recipients had a complete necropsy performed by the Yerkes Veterinary Staff at the time of their death.

Detection of Anti-donor antibodies. The presence of detectable donor specific alloantibody was determined using flow cytometry. Peripheral blood leukocytes served as the target cells for the pre-transplant analysis. Leukocytes isolated from mesenteric lymph nodes obtained at the time of transplant were the target cells for the post-transplant assays.

Statistics. Survival of the islet grafts among experimental groups was compared using the Mann-Whitney-Wilcoxon test (Armitage et al. (1987) *Statistical methods in Medical Research*, Blackwell Scientific Publication, Oxford).

Anti-donor enzyme-linked immunospot assay. Responses were measured by interferon-γ (IFN-γ) enzyme-linked immunospot (ELISpot) assay using peripheral blood leukocytes obtained from the recipient and donor animals. An equal number of irradiated stimulators (donor leukocytes) and responders (recipient leukocytes) were added to ester cellulose bottom plates (Millipore, Bedford, Mass.) coated with the capture antibody, mouse anti-human IFN-γ (clone GZ-4; Mabtech, Sweden). After 14-16 h incubation, biotinylated mouse anti-human IFN-γ (clone 7-B6-1; Mabtech, Sweden) was added, unbound antibody was removed, and horseradish peroxidase-Avidin D (Vector, Burlingame, Calif.) was added. Spots were developed with the substrate 3-amino-9-ethyl-carbazole (Sigma). Each spot represents an IFN-γ-secreting cell; the frequency of these cells can be determined by dividing the number of spots generated by the total number of responder cells plated.

Results

CD28 pathway blockade-based therapy prolongs the survival of the islet allografts in Rhesus macaques. Diabetes was induced by surgical pancreatectomy of recipient animals and confirmed by pretransplant intravenous glucose tolerance test. Donor-recipient pairings were defined based on molecular typing using a panel of previously defined major histocompatibilty alleles (8 class I and 12 class II) (Lobashevsky A, et al., *Tissue Antigens* 54:254-263, (1999);

Knapp L A, et al., *Tissue Antigens* 50:657-661, (1997); Watkins D. I., *Crit Rev Immunol* 15:1-29, (1995)). Pairings maximized disparity at both class I and II loci. Rejection was defined as two consecutive fasting blood glucose values >125 mg/dl on subsequent days. Intra-portal infusion of allogeneic islets (>10,000 IEQ/Kg) resulted in initial restoration of euglycemia and insulin independence in diabetic monkeys in both groups.

Figure 6:
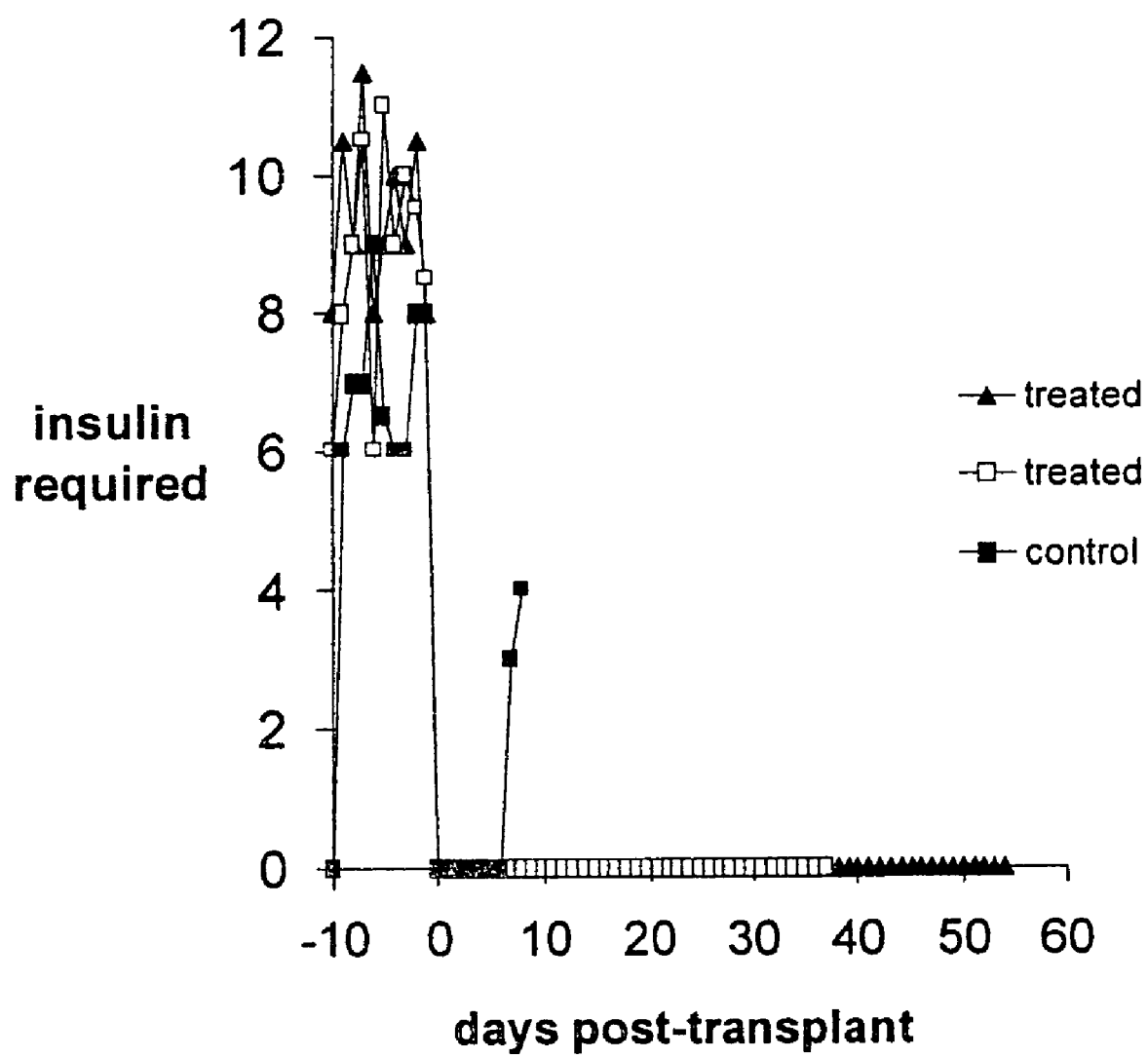
FIG. 6 is a line graph illustrating insulin requirement in subjects with transplanted islet cells as described in Example 3. The animals were transplanted with islet cells on day 0, and were treated with an immunosuppressive regimen containing L104EA29YIg and a base immunosuppressive regimen (treated), or only a base immunosuppressive regimen (control).

Treatment of pancreatectomized macaques with the L104EA29YIg/Rapamycin/anti-IL-2R mAb regimen significantly prolonged islet allograft survival (204, 190, 216, >220 and 56 days, respectively). The animals receiving L104EA29YIg/Rapamycin/anti-IL-2R regimen resulted in adequate glucose control as indicated by fasting plasma glucose levels (FIGS. 5 and 16B). In addition, these animals did not require insulin replacement therapy for a significantly prolonged period of time (FIG. 6). In contrast, those animals receiving the base regimen alone (Rapamycin/anti-IL-2R mAb) rejected the transplanted islets within one week (FIG. 16C). The control animals showed markedly elevated levels of fasting plasma glucose (FIGS. 5). Further, the control animals required insulin replacement therapy within one week of islet transplant (FIG. 6). Four of five animals receiving the L104EA29YIg regimen enjoyed rejection-free survival for the duration of the treatment period (Table III). Intravenous glucose tolerance test with measurement of insulin and glucose levels confirmed islet function posttransplant (representative animal, FIGS. 7 and 16D).

TABLE III

Islet allograft survival and treatment

| | IEQ/kg | Survival* | Treatment | MHC mismatches (n) Class I | Class II |
|---|---|---|---|---|---|
| RKf-7 | 22,250 | 204 | LEA29Y/Rapa/αIL-2R | 2 | ND |
| RUf-7 | 17,087 | 190 | LEA29Y/Rapa/αIL-2R | ND | 3 |
| RRe-7 | 20,266 | 216 | LEA29Y/Rapa/αIL-2R | 2 | 6 |
| RWt-6 | 16,033 | 56 | LEA29Y/Rapa/αIL-2R | 2 | 3 |
| RMv-6 | 8,201 | >220 | LEA29Y/Rapa/αIL-2R | 1 | 3 |
| RQz-6 | 12,980 | 7 | Rapa/αIL-2R | 2 | 5 |
| RIb-7 | 10,903 | 7 | Rapa/αIL-2R | 1 | 4 |

*Insulin independence.
ND, none detected in alleles that were typed.

At 100 days posttransplant, the dosing of rapamycin was decreased and tapered to zero by day 121. Animals continued to remain insulin-independent while receiving L104EA29YIg monotherapy. At ~150 days posttransplant, the remaining islet recipients received their final dose of L104EA29YIg, ceasing any additional immunosuppressive therapy.

Figure 7:
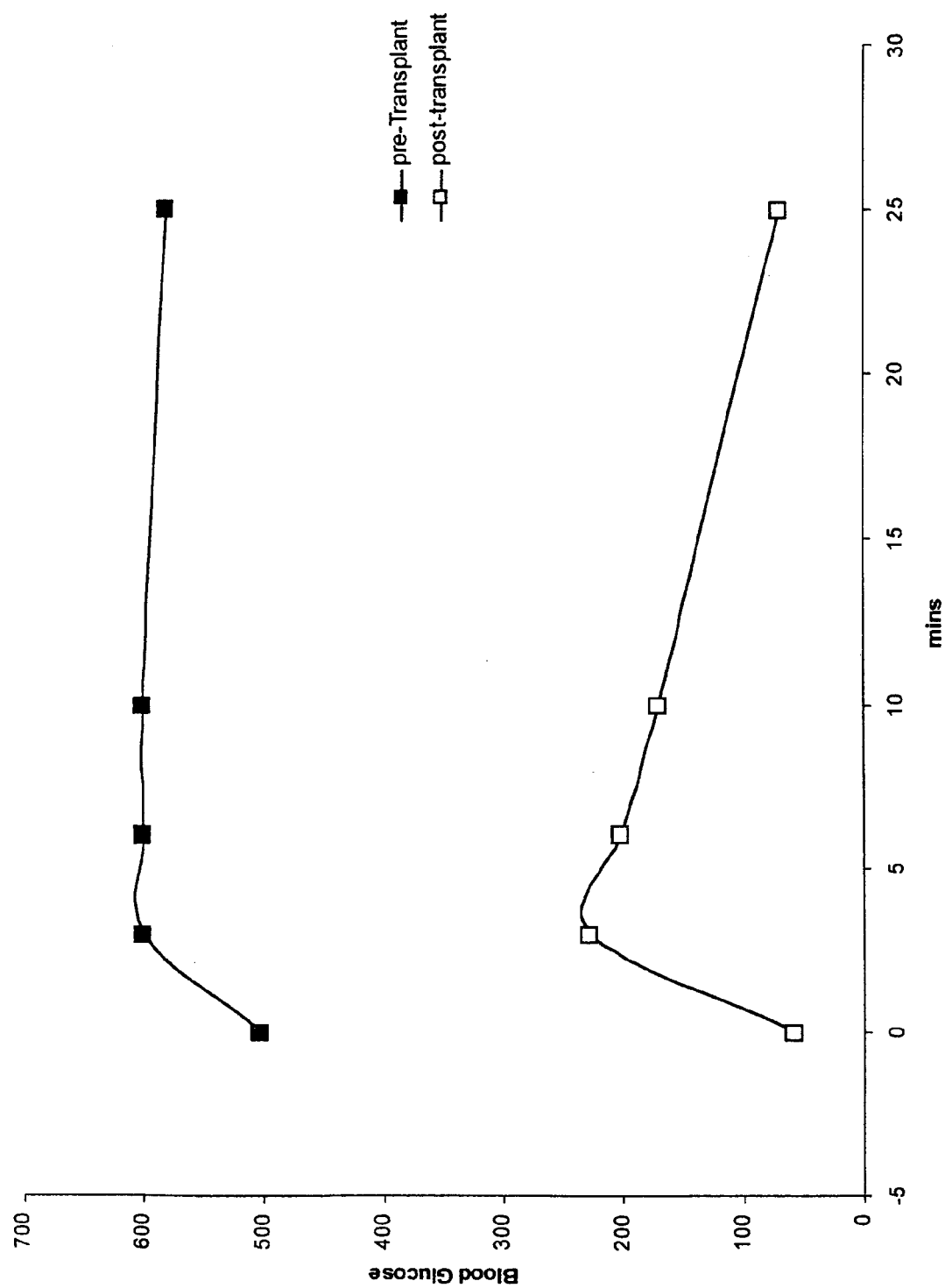
FIG. 7 is a line graph illustrating blood glucose level in an intravenous glucose tolerance test pre- and post-islet transplant, as described in Example 3.
Figure 8:
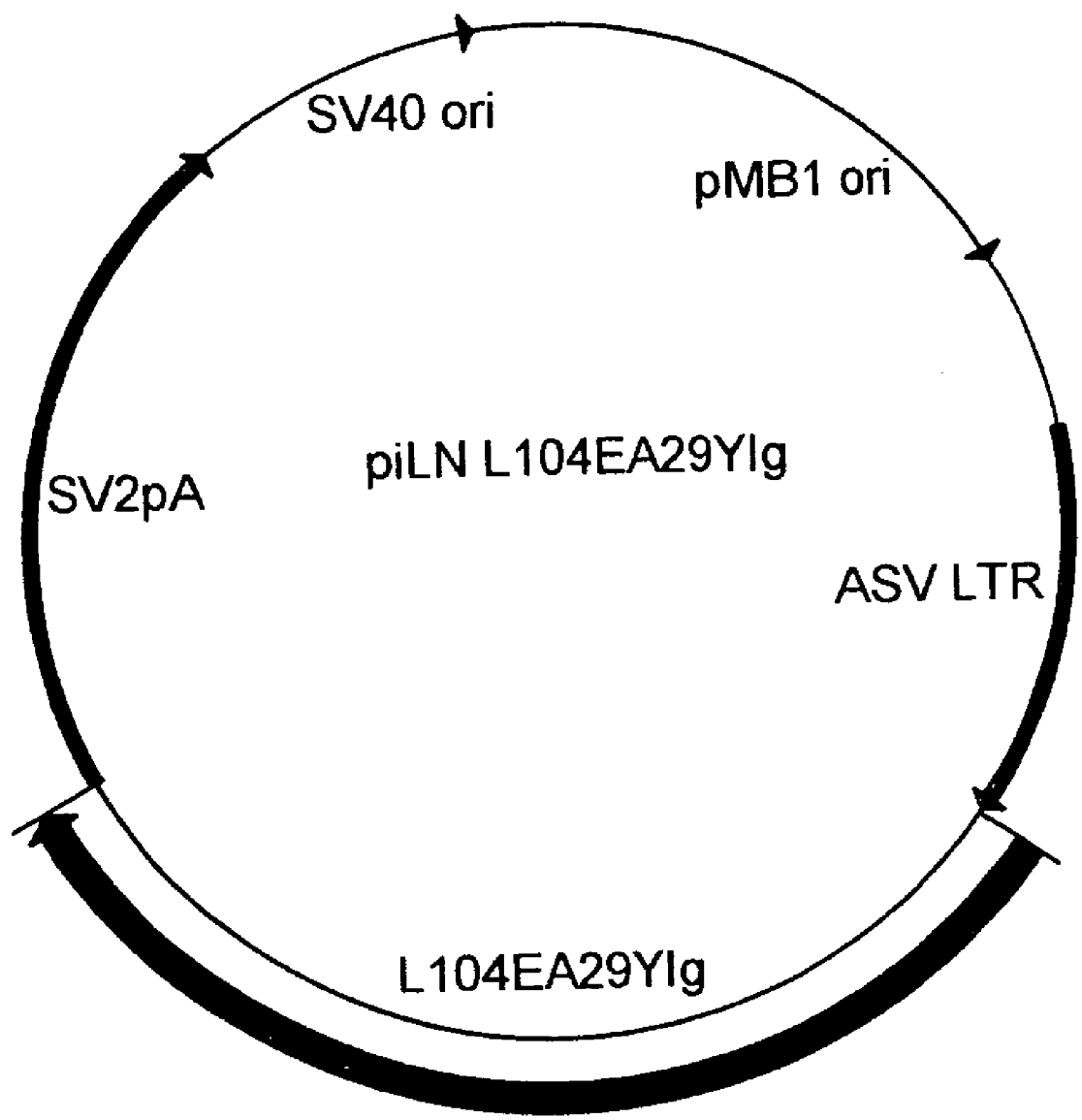
FIG. 8 depicts a schematic diagram of a vector, piLN-L104EA29Y, having the L104EA29YIg insert.
Figure 17A:
FIG. 17 depicts (A) immunohistology of functional transplanted islet confirmed by positive staining for insulin. (B) islet from an animal receiving control regimen surrounded by mononuclear infiltrate, indicating rejection, as described in Example 3, infra.
Figure 17B:
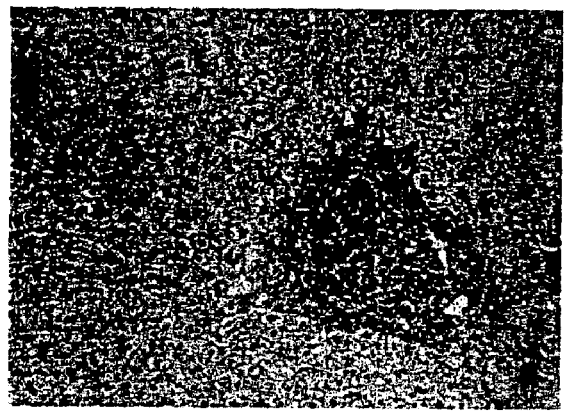

As expected, ~1-2 months after discontinuation of therapy, recipients became hyperglycemic and required exogenous insulin therapy. Histological analysis revealed a mononuclear infiltrate, strongly suggesting rejection as the etiology of the loss of glucose control (FIG. 17). In an intravenous glucose tolerance test, the test animals receiving L104EA29YIg/Rapamycin/anti-IL-2R mAb regimen demonstrated normal glucose levels post islet transplant (FIGS. 7 and 16D).

The frequency of anti-donor IFN-γ producing cells was detected by ELISpot assay and analyzed using an Immunspot imaging system. Animals receiving the base immunosuppressive regimen alone demonstrated significantly increased numbers of donor-reactive IFNγ producing T cells (84±4.6 cells), while animals receiving the L104EA29YIg regimen had no detectable response (2±0.56 cells).

Figure 18A:
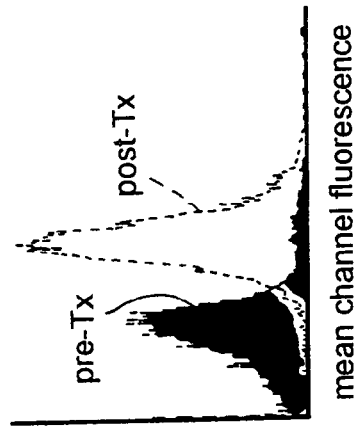
FIG. 18 depicts suppression of anti-donor T- and B-cell responses by L104EA29Y regimen. (A) Anti-donor IFN-γ-ELISpot response corresponds to timing of rejection in the controls (~1 week posttransplant). (B) L104EA29Y regimen effectively suppresses the generation of anti-donor T cell response. (C) animals receiving rapamycin anti-IL-2R mAb quickly produce detectable anti-donor antibody, as measured by flow cytometric methods at the time of rejection. (D)) islet recipients receiving the L104EA29Y-containing regimen fail to generate a detectable anti-donor antibody response while treated, as described in Example 3, infra.

L104EA29YIg therapy inhibits priming of anti-donor T- and B-cell responses. The frequency of primed alloreactive T-cells can effectively be detected by using the ELISpot assay, which can discriminate production of IFN-γ at the single-cell level. Peripheral blood samples from islet recipients were analyzed at various time points both pre- and posttransplant for their ability to generate IFN-γ in response to donor antigen. Animals treated with the base regimen alone quickly developed a measurable anti-donor response that coincided with rejection 1 week after transplant. In contrast, the frequency of anti-donor IFN-γ producing cells in animals receiving the L104EA29YIg-containing regimen was undetectable until therapy was withdrawn (representative animals, FIG. 18A and B). Thus, the L104EA29YIg regimen effectively blocked the generation of anti-donor T-cell responses as measured by the ability to produce IFN-γ.

Figure 18C:
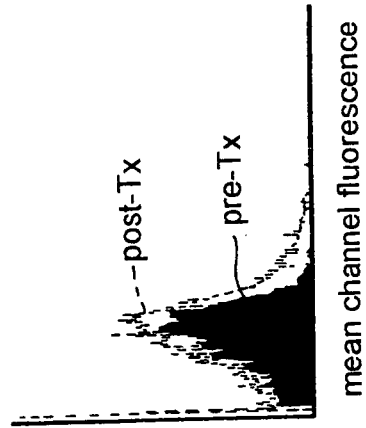
Figure 18B:
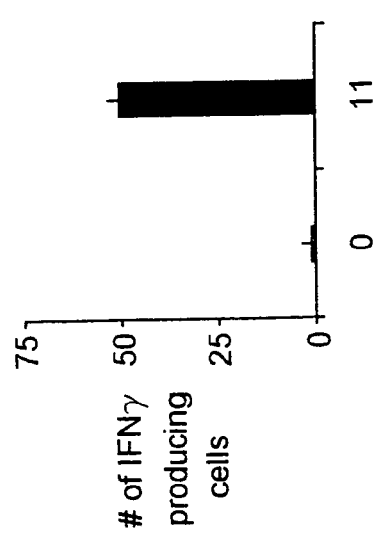
Figure 18D:
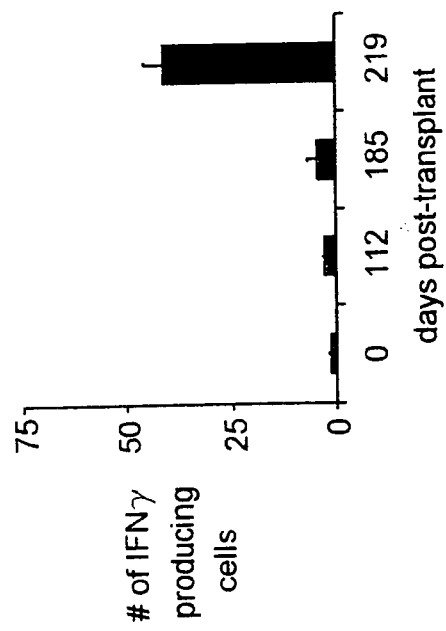

Flow cytometry was used to examine the development of anti-donor antibody responses. One animal within the control group generated a strong anti-donor Ab response, whereas the other failed to develop a detectable response, presumably because it was euthanized before the antibody response could be measured (FIG. 18C). In contrast, four of five animals failed to generate an antibody response while receiving L104EA29YIg therapy. This is consistent with previously reported results using CTLA4-Ig in an islet transplant model (Levisetti, M. G. et al., *J Immunol* 159: 5187-5191, 1997) as well as our experience in a renal allograft model where recipients failed to generate anti-donor anti-bodies (Pearson T, ET AL., (Abstract). In Programs and Abstracts of the 17th American Society of Transplant Physicians Annual Meeting, Chicago, 10-14 May 1997. Chicago, American Society of Transplant Physicians). One animal of five recipients underwent a rejection episode while receiving the L104EA29YIg therapy and subsequently developed an anti-donor antibody response. As expected, the remaining four animals receiving the L104EA29YIg regimen consistently developed anti-donor anti-body responses around the time of rejection (~200 days posttransplant, 50 days after the final dose of L104EA29YIg).

Islet transplantation is quickly becoming a viable treatment option for patients with brittle type 1 diabetes. Recent reports describing steroid-free immunosuppressive regimens, which result in successful insulin independence after islet transplantation, have ushered in renewed optimism for the practical application of islet transplantation. Whereas the elimination of glucocorticoids from immunosuppressive regimens represents a major step forward in the effort to treat type 1 diabetes, the reliance on calcineurin inhibitor therapy for primary immunosuppression may limit the application of this approach. Calcineurin inhibitors have numerous unwanted side effects, including nephrotoxicity, diabetes, hypertension, impaired lipid metabolism, and hirusitism (Kahan B. D. et al., *N Engl J Med* 321:1725-1738, 1989; Group TUSMFLS: A comparison of tacrolimus (FK 506) and cyclosporine for immunosuppression in liver transplantation: the U.S. Multicenter FK506 Liver Study Group. *N Engl J Med* 331:1110-1115, 1994; de Mattos AM et al., *Am J Kidney Disease* 35:333-346, 2000). Even when drug levels are kept low, significant side effects may develop. This is particularly true in the diabetic patient population where renal function may already be impaired. Indeed, in the most recent reports from Edmonton, two patients with mildly elevated pretransplant creatinine levels had significant decreases in renal function while on calcineurin inhibitor therapy and ultimately required withdrawal of this drug (Ryan E. A., et al., *Diabetes* 50:710-719, 2001). In the same report, two-thirds of recipients developed some degree of glucose intolerance, with one-quarter developing frank post-transplant diabetes thought to be related to the use of tacrolimus. This underscores the appealing and essential nature of a calcineurin inhibitor-free immunosuppressive regimen, particularly for islet transplantation.

Blockade of T-cell costimulatory pathways is a promising strategy for the development of nontoxic immunosuppressive and potentially tolerogenic regimens. This approach targets those T-cells that receive "signal 1" during the period of drug administration. For example, treatment during the peritransplant period is thought to render allo-specific T-cells impotent upon encounter with the new organ or tissue, whereas other T-cells are left unimpaired (Li Y, et al., *Nat Med* 5:1298-1302, 1999). Blockade of the CD28/B7 pathway has demonstrated remarkable promise in experimental models of autoimmunity and transplantation, making it a particularly appealing immunosuppressive target in islet transplantation, where presumably both auto- and allo-immune obstacles exist. The potential of CD28 blockade in a large animal transplant model was described by Levisetti M G, et al., (*J Immunol* 159:5187-5191, 1997). Treatment with CTLA4-Ig was found to significantly, although modestly, prolong islet allograft survival in nonhuman primates (Levisetti M G, et al., *J Immunol* 159:5187-5191, 1997). CTLA4-Ig monotherapy does little to prolong renal allograft survival (Pearson T. et al., (Abstract). In *Programs and Abstracts of the 17th American Society of Transplant Physicians Annual Meeting, Chicago,* 10-14 *May* 1997. Chicago, American Society of Transplant Physicians). Recently, there have been several reports of long-term survival of islet allografts in nonhuman primate models. Anti-CD40L mAb therapy has shown the most impressive results thus far; however, similar to experiments using a renal transplant model, tolerance was not achieved, as withdrawal of therapy eventually resulted in rejection (Kenyon, N. S. et al., *Proc. Natl. Acad. Sci. USA* 96:8132-8137 (1999); Kirk, A. D., et al., *Nat. Med.* 5, 686-693 (1999). In another encouraging report, Thomas et al. (*Diabetes* 50:1227-1236 (2001)) recently described the use of an anti-CD3 immunotoxin and the immune modulatory agent DSG (15 deoxyspergualin) to dramatically prolong islet survival in streptozotocin-induced diabetic primates. Although promising, these reports used therapeutics whose clinical potential at the present time is still uncertain.

The in vivo data using L104EA29YIg, a mutant form of CTLA4-Ig, in the Rhesus islet allograft model is consistent with in vitro evidence indicating that this second generation molecule is a more potent inhibitor of T-cell responses than the parent molecule. Given that CTLA4-Ig has already shown efficacy in a clinical trial of psoriasis patients (Abrams, J. R. et al., *J. Clin. Invest.* 103:1243-1252 (1999)), there is significant enthusiasm for the trials using L104EA29YIg as the primary immunosuppressant. It is clearly compatible, if not synergistic, with clinically approved immunosuppressive agents (anti-IL-2R mAb and rapamycin) facilitating the design of clinical trials. Initial human trials with L104EA29YIg are already underway in patients afflicted with rheumatoid arthritis and those undergoing renal transplant. Although a direct comparison of a tacrolimus-based protocol and the L104EA29YIg regimen was not attempted because of reported intolerable toxicities in nonhuman primates (Montgomery, S. P., et al., *Am J. Transplant* 1 (*Suppl.* 1):438, 2001), our results suggest that L104EA29YIg has the potential to be at least as effective as tacrolimus as a primary immunosuppressant.

CONCLUSIONS

A novel calcineurin inhibitor/steroid-free immunosuppressive regimen that provides significant protection from rejection and prolongs the survival of islet allografts in nonhuman primates is described. The biologic agent L104EA29YIg is a potent immunosuppressant. L104EA29YIg may replace Tacrolimus in the Edmonton protocol, thereby eliminating the unwanted side effects of the calcineurin inhibitor.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

What is claimed is:

1. A method for inhibiting islet cell transplant rejection in a subject, comprising administering to the subject an effective amount of a CTLA4 molecule comprising a mutated extracellular domain comprising an amino acid sequence beginning with alanine at position 26 and ending with aspartic acid at position 150 as shown in SEQ ID NO:6, or beginning with methionine at position 27 and ending with aspartic acid at position 150 as shown in SEQ ID NO:6.

2. A method for treating diabetes by inhibiting islet cell transplant rejection in a subject by the method of claim 1.

3. The method of claim 1, wherein the islet cells are encapsulated prior to administration to the subject.

4. The method of claim 1, further comprising administering to the subject an effective amount of at least one of an immunosuppressive agent, an immunomodulatory compound, and an anti-inflammatory agent, wherein the CTLA4 molecule and at least one of an immunosuppressive agent, an immunomodulatory compound and an anti-inflammatory agent are to be administered concomitantly or in sequence.

5. The method of claim 4, wherein the immunosuppressive agent is (i) rapamycin (sirolimus) or its derivative 40-O-(2-hydroxy)ethyl-rapamycin, (ii) anti-human IL-2R mAb, or (iii) a combination of (i) and (ii).

6. The method of claim 4, wherein the immunosuppressive agent is a cyclosporin, tacrolimus, prednisone, azathioprine, methotrexate, infliximab, hydroxychloroquine, sulphasalazopryine, etanercept, anakinra, basiliximab, chloroquine, cyclophosphamide, cytoxan, 15-deoxyspergualine, D-penicillamine, glatiramer acetate, FTY720, horse anti-human thymocyte globulin (ATGAM), humanized anti-TAC (HAT), interferon beta-1a, interferon beta-1b, leflunomide, lymphocyte immune globulin, methoxsalen, mitoxantrone hydrochloride, mycophenolic acid, mycophenolate mofetil, mizoribine, rabbit anti-human thymocyte globulin, Rho (D) immune globulin, sirolimus (rapamycin), sulfasalzine, thalidomide, soluble gp39, soluble CD29, soluble CD40, soluble CD80, soluble CD86, soluble CD28, soluble CD56, soluble Thy-1, soluble CD3, soluble TCR, soluble VLA-4, soluble VCAM-1, soluble LECAM-1, soluble ELAM-1, soluble CD44, antibodies to gp39, antibodies to CD40, antibodies to B7-1 or B7-2, antibodies to CD28, antibodies to LFA-1, antibodies to LFA-2, antibodies to IL-2, antibodies to IL 12, antibodies to IFN-gamma, antibodies to CD2, antibodies to CD48, antibodies to any ICAM, antibodies to CTLA4, antibodies to Thy-1, antibodies to CD56, antibodies to CD3, antibodies to CD29, antibodies to TCR, antibodies to VLA-4, antibodies to VCAM-1, antibodies to LECAM-1, antibodies to ELAM-1, antibodies to CD44, monoclonal antibodies to OX40, or 4-1BB CTLA4/CD28-1g, anti-human IL-2R mAbs, 40-0 (2hydroxy)ethyl-rapamycin, soluble CD80 deposited as ATCC 68627, an antibody to any of ICAM-1, ICAM-2 and ICAM-3, or a monoclonal antibody to any of MHC, CD2, CD3, CD4, CD11a/CD18, CD7, CD25, CD27, B7, CD40, CD45, CD58, CD137, ICOS, or CD150 (SLAM).

7. The method of claim 4, wherein administration is by intravenous injection, intramuscular injection, subcutaneous injection, implantable pump, continuous infusion, gene therapy, liposomes or oral administration.

8. The method of claim 1, wherein the subject is a human, non-human primate, rabbit, sheep, rat, dog, cat, pig, or mouse.

9. The method of claim 1 further comprising administering T cell depleted bone marrow cells to the subject.

10. The method of claim 1, wherein the subject is being transplanted with islet cells before, or after, administration of the CTLA4 molecule.

11. The method of claim 2, wherein diabetes is type 1 diabetes or type 2 diabetes.

12. The method of claim 1, wherein the mutated extracellular domain is fused to a non-CTLA4 moiety.

13. The method of claim 12, wherein the non-CTLA4 moiety comprises an immunoglobulin moiety.

14. The method of claim 13, wherein the immunoglobulin moiety is an immunoglobulin constant region or portion thereof.

15. The method of claim 14, wherein the immunoglobulin constant region or portion thereof comprises one or more mutations to reduce effector function.

16. The method of claims 14 or 15, wherein the immunoglobulin constant region comprises the hinge, CH2 and CH3 regions of an immunoglobulin molecule.

17. The method of claim 14, wherein the immunoglobulin constant region or portion thereof is a human or monkey immunoglobulin constant region.

18. A method for inhibiting islet cell transplant rejection in a subject, comprising administering to the subject an effective amount of a soluble CTLA4 mutant molecule, wherein the soluble CTLA4 mutant molecule comprises an amino acid sequence as shown in SEQ ID NO:6 beginning with alanine at position 26 and ending with lysine at position 383, or beginning with methionine at position 27 and ending with lysine at position 383.

19. The method of claims 1 or 18 further comprising administering to the subject an effective amount of an immunosuppressive agent.

20. The method of claim 19, wherein the immunosuppressive agent is glucocorticoid-free.

21. The method of claim 19, wherein the immunosuppressive agent is calcineurin inhibitor-free.

22. The method of claim 19, wherein the immunosuppressive agent comprises (i) rapamycin (sirolimus) or its derivative 40-O-(2-hydroxy)ethyl-rapamycin, (ii) anti-IL-2R monoclonal antibody, or (iii) a combination of (i) and (ii).

23. The method of claim 22, wherein the anti-IL-2R monoclonal antibody is basiliximab.

24. A method for inhibiting islet cell transplant rejection in a subject, comprising administering to the subject an effective amount of a soluble CTLA4 mutant molecule encoded by DNA deposited as ATCC number PTA-2104.

25. A method for inhibifmg islet cell transplant rejection in a subject, comprising administering to the subject an effective amount of a soluble CTLA4 mutant molecule expressed by DNA deposited as ATCC number PTA-2104.

26. The method of claims 24 or 25, further comprising administering to the subject an effective amount of an immunosuppressive agent.

27. The method of claim 26, wherein the immunosuppressive agent is glucocorticoid-free.

28. The method of claim 26, wherein the immunosuppressive agent is calcineurin inhibitor-free.

29. The method of claim 26, wherein the immunosuppressive agent comprises (i) rapamycin (sirolimus) or its derivative 40-O-(2-hydroxy)ethyl-rapamycin, (ii) an anti-IL-2R monoclonal antibody, or (iii) a combination of (i) and (ii).

30. The method of claim 29, wherein the anti-IL-2R monoclonal antibody is basiliximab.

31. The method of claims 1 or 4, wherein the CTLA4 molecule is encoded by DNA deposited as ATCC number PTA 2104.

32. The method of claims 1 or 4, wherein the CTLA4 molecule is expressed by DNA deposited as ATCC number PTA 2104.

* * * * *

UNITED STATES PATENT AND TRADEMARK OFFICE
CERTIFICATE OF CORRECTION

PATENT NO. : 7,304,033 B2
APPLICATION NO. : 10/155514
DATED : December 4, 2007
INVENTOR(S) : Christian P. Larsen et al.

It is certified that error appears in the above-identified patent and that said Letters Patent is hereby corrected as shown below:

Column 2
Line 6 "azathiprine" is misspelled should be --azathioprine--
Line 14 "Tarcolimus" is misspelled should be --Tacrolimus--
Line 27 "Tarcolimus" is misspelled should be --Tacrolimus--

Column 18
Line 38 "Manasas" is misspelled should be --Manassas--

Column 20
Line 61 "glucococoticoids" is misspelled should be --glucocorticoids--

Column 24
Line 19 "mtant" is misspelled should be --mutant--

Column 26
Line 19 "tacrolismus" is misspelled should be --tacrolimus--

Column 31
Line 44 "Chromatogragphy" is misspelled should be --Chromatography--

Column 32
Line 40 "aggregration" is misspelled should be --aggregation--
Line 61 "identifed" is misspelled should be --identifed--
Line 63 "aggregration" is misspelled should be --aggregation--

Column 37
Line 62 "adminstration" is misspelled should be --administration--

UNITED STATES PATENT AND TRADEMARK OFFICE
CERTIFICATE OF CORRECTION

| | |
|---|---|
| PATENT NO. | : 7,304,033 B2 |
| APPLICATION NO. | : 10/155514 |
| DATED | : December 4, 2007 |
| INVENTOR(S) | : Christian P. Larsen et al. |

It is certified that error appears in the above-identified patent and that said Letters Patent is hereby corrected as shown below:

In the Claims:

Claim 25:
Line 51 "inhibifmg" is misspelled should be --inhibiting--

Signed and Sealed this

Twenty-ninth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,304,033 B2
APPLICATION NO. : 10/155514
DATED : December 4, 2007
INVENTOR(S) : Christian P. Larsen et al.

It is certified that error appears in the above-identified patent and that said Letters Patent is hereby corrected as shown below:

Column 2
Line 6 "azathiprine" is misspelled should be --azathioprine--
Line 14 "Tarcolimus" is misspelled should be --Tacrolimus--
Line 27 "Tarcolimus" is misspelled should be --Tacrolimus--

Column 18
Line 38 "Manasas" is misspelled should be --Manassas--

Column 20
Line 61 "glucococoticoids" is misspelled should be --glucocorticoids--

Column 24
Line 19 "mtant" is misspelled should be --mutant--

Column 26
Line 19 "tacrolismus" is misspelled should be --tacrolimus--

Column 31
Line 44 "Chromatogragphy" is misspelled should be --Chromatography--

Column 32
Line 40 "aggregration" is misspelled should be --aggregation--
Line 61 "identifed" is misspelled should be --identifed--
Line 63 "aggregration" is misspelled should be --aggregation--

Column 37
Line 62 "adminstration" is misspelled should be --administration--

UNITED STATES PATENT AND TRADEMARK OFFICE
CERTIFICATE OF CORRECTION

| | | |
|---|---|---|
| PATENT NO. | : 7,304,033 B2 | |
| APPLICATION NO. | : 10/155514 | |
| DATED | : December 4, 2007 | |
| INVENTOR(S) | : Christian P. Larsen et al. | |

It is certified that error appears in the above-identified patent and that said Letters Patent is hereby corrected as shown below:

In the Claims:

Column 70
Line 51 "inhibifmg" is misspelled should be --inhibiting--

This certificate supersedes the Certificate of Correction issued April 29, 2008.

Signed and Sealed this

Twenty-seventh Day of May, 2008

JON W. DUDAS
*Director of the United States Patent and Trademark Office*

SEQUENCE LISTING

```
<160> NUMBER OF SEQ ID NOS: 18

<210> SEQ ID NO 1
<211> LENGTH: 636
<212> TYPE: DNA
<213> ORGANISM: Homo sapiens

<400> SEQUENCE: 1
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcca gctttgtgtg tgagtatgca tctccaggca aagccactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
```

-continued

```
gagctcatgt acccaccgcc atactacctg ggcataggca acggaaccca gatttatgta    420
attgatccag aaccgtgccc agattctgac ttcctcctct ggatccttgc agcagttagt    480
tcggggttgt ttttttatag cttttctcctc acagctgttt ctttgagcaa aatgctaaag   540
aaaagaagcc ctcttacaac agggtctat gtgaaaatgc ccccaacaga gccagaatgt     600
gaaaagcaat ttcagcctta ttttattccc atcaat                              636
```

```
<210> SEQ ID NO 2
<211> LENGTH: 212
<212> TYPE: PRT
<213> ORGANISM: Homo sapiens

<400> SEQUENCE: 2
```

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Phe Leu Leu Trp Ile Leu Ala Ala Val Ser
145                 150                 155                 160

Ser Gly Leu Phe Phe Tyr Ser Phe Leu Leu Thr Ala Val Ser Leu Ser
                165                 170                 175

Lys Met Leu Lys Lys Arg Ser Pro Leu Thr Thr Gly Val Tyr Val Lys
            180                 185                 190

Met Pro Pro Thr Glu Pro Glu Cys Glu Lys Gln Phe Gln Pro Tyr Phe
        195                 200                 205

Ile Pro Ile Asn
    210

```
<210> SEQ ID NO 3
<211> LENGTH: 1152
<212> TYPE: DNA
<213> ORGANISM: Artificial Sequence
<220> FEATURE:
<223> OTHER INFORMATION: Description of Artificial Sequence: CTLA4Ig
      sequence

<400> SEQUENCE: 3
atgggtgtac tgctcacaca gaggacgctg ctcagtctgg tccttgcact cctgtttcca    60
agcatggcga gcatggcaat gcacgtggcc cagcctgctg tggtactggc cagcagccga    120
ggcatcgcta gctttgtgtg tgagtatgca tctccaggca aagccactga ggtccgggtg    180
acagtgcttc ggcaggctga cagccaggtg actgaagtct gtgcggcaac ctacatgatg    240
```

-continued

```
gggaatgagt tgaccttcct agatgattcc atctgcacgg gcacctccag tggaaatcaa      300
gtgaacctca ctatccaagg actgagggcc atggacacgg actctacat ctgcaaggtg       360
gagctcatgt accccaccgcc atactacctg gcataggca acggaaccca gatttatgta      420
attgatccag aaccgtgccc agattctgat caggagccca atcttctga caaaactcac       480
acatccccac cgtccccagc acctgaactc ctgggtggat cgtcagtctt cctcttcccc      540
ccaaaaccca aggacaccct catgatctcc cggaccctg aggtcacatg cgtggtggtg       600
gacgtgagcc acgaagaccc tgaggtcaag ttcaactggt acgtgacgg cgtggaggtg       660
cataatgcca agacaaagcc gcgggaggag cagtacaaca gcacgtaccg ggtggtcagc      720
gtcctcaccg tcctgcacca ggactggctg aatggcaagg agtacaagtg caaggtctcc      780
aacaaagccc tcccagcccc catcgagaaa accatctcca agccaaagg gcagccccga       840
gaaccacagg tgtacaccct gcccccatcc cgggatgagc tgaccaagaa ccaggtcagc      900
ctgacctgcc tggtcaaagg cttctatccc agcgacatcg ccgtggagtg ggagagcaat      960
gggcagccgg agaacaacta caagaccacg cctcccgtgc tggactccga cggctccttc     1020
ttcctctaca gcaagctcac cgtggacaag agcaggtggc agcaggggaa cgtcttctca     1080
tgctccgtga tgcatgaggc tctgcacaac cactacacgc agaagagcct ctccctgtct     1140
ccgggtaaat ga                                                        1152
```

<210> SEQ ID NO 4
<211> LENGTH: 383
<212> TYPE: PRT
<213> ORGANISM: Artificial Sequence
<220> FEATURE:
<223> OTHER INFORMATION: Description of Artificial Sequence: CTLA4Ig
      sequence

<400> SEQUENCE: 4

```
Met Gly Val Leu Leu Thr Gln Arg Thr Leu Leu Ser Leu Val Leu Ala
1               5                  10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190
```

```
Pro Glu Val Thr Cys Val Val Asp Val Ser His Glu Asp Pro Glu
        195                 200                 205
Val Lys Phe Asn Trp Tyr Val Asp Gly Val Glu Val His Asn Ala Lys
        210                 215                 220
Thr Lys Pro Arg Glu Glu Gln Tyr Asn Ser Thr Tyr Arg Val Val Ser
225                 230                 235                 240
Val Leu Thr Val Leu His Gln Asp Trp Leu Asn Gly Lys Glu Tyr Lys
                245                 250                 255
Cys Lys Val Ser Asn Lys Ala Leu Pro Ala Pro Ile Glu Lys Thr Ile
                260                 265                 270
Ser Lys Ala Lys Gly Gln Pro Arg Glu Pro Gln Val Tyr Thr Leu Pro
                275                 280                 285
Pro Ser Arg Asp Glu Leu Thr Lys Asn Gln Val Ser Leu Thr Cys Leu
        290                 295                 300
Val Lys Gly Phe Tyr Pro Ser Asp Ile Ala Val Glu Trp Glu Ser Asn
305                 310                 315                 320
Gly Gln Pro Glu Asn Asn Tyr Lys Thr Thr Pro Pro Val Leu Asp Ser
                325                 330                 335
Asp Gly Ser Phe Phe Leu Tyr Ser Lys Leu Thr Val Asp Lys Ser Arg
                340                 345                 350
Trp Gln Gln Gly Asn Val Phe Ser Cys Ser Val Met His Glu Ala Leu
                355                 360                 365
His Asn His Tyr Thr Gln Lys Ser Leu Ser Leu Ser Pro Gly Lys
        370                 375                 380

<210> SEQ ID NO 5
<211> LENGTH: 1152
<212> TYPE: DNA
<213> ORGANISM: Artificial Sequence
<220> FEATURE:
<223> OTHER INFORMATION: Description of Artificial Sequence: L104EA29YIg
      sequence

<400> SEQUENCE: 5
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aatatactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
gagctcatgt acccaccgcc atactacgag ggcataggca cggaaccca gatttatgta     420 attgatccag aaccgtgccc agattctgat caggagccca atcttctga caaaactcac     480 acatccccac cgtccccagc acctgaactc ctggggggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg tgtggtcagc     720
gtcctcaccg tcctgcacca ggactggctg aatggcaagg agtacaagtg caaggtctcc     780
aacaaagccc tcccagcccc catcgagaaa accatctcca aagccaaagg cagccccga     840 gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
```

```
gggcagccgg agaacaacta caagaccacg cctcccgtgc tggactccga cggctccttc    1020
ttcctctaca gcaagctcac cgtggacaag agcaggtggc agcagggaa cgtcttctca     1080 tgctccgtga tgcatgaggc tctgcacaac cactacacgc agaagagcct ctccctgtct    1140
ccgggtaaat ga                                                        1152
```

<210> SEQ ID NO 6
<211> LENGTH: 383
<212> TYPE: PRT
<213> ORGANISM: Artificial Sequence
<220> FEATURE:
<223> OTHER INFORMATION: Description of Artificial Sequence: L104EA29YIg
       sequence

<400> SEQUENCE: 6

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Tyr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320
```

Gly Gln Pro Glu Asn Asn Tyr Lys Thr Thr Pro Pro Val Leu Asp Ser
            325                 330                 335

Asp Gly Ser Phe Phe Leu Tyr Ser Lys Leu Thr Val Asp Lys Ser Arg
        340                 345                 350

Trp Gln Gly Asn Val Phe Ser Cys Ser Val Met His Glu Ala Leu
    355                 360                 365

His Asn His Tyr Thr Gln Lys Ser Leu Ser Leu Ser Pro Gly Lys
    370                 375                 380

<210> SEQ ID NO 7
<211> LENGTH: 1152
<212> TYPE: DNA
<213> ORGANISM: Artificial Sequence
<220> FEATURE:
<223> OTHER INFORMATION: Description of Artificial Sequence: L104EIg
      sequence

<400> SEQUENCE: 7

| | | | | | |
|---|---|---|---|---|---|
| atgggtgtac | tgctcacaca | gaggacgctg | ctcagtctgg | tccttgcact | cctgtttcca | 60 |
| agcatggcga | gcatggcaat | gcacgtggcc | cagcctgctg | tggtactggc | cagcagccga | 120 |
| ggcatcgcta | gctttgtgtg | tgagtatgca | tctccaggca | aagccactga | ggtccgggtg | 180 |
| acagtgcttc | ggcaggctga | cagccaggtg | actgaagtct | gtgcggcaac | ctacatgatg | 240 |
| gggaatgagt | tgaccttcct | agatgattcc | atctgcacgg | gcacctccag | tggaaatcaa | 300 |
| gtgaacctca | ctatccaagg | actgagggcc | atggacacgg | gactctacat | ctgcaaggtg | 360 |
| gagctcatgt | acccaccgcc | atactacgag | ggcataggca | acggaaccca | gatttatgta | 420 |
| attgatccag | aaccgtgccc | agattctgat | caggagccca | aatcttctga | caaaactcac | 480 |
| acatccccac | cgtccccagc | acctgaactc | ctggggggat | cgtcagtctt | cctcttcccc | 540 |
| ccaaaaccca | aggacaccct | catgatctcc | cggacccctg | aggtcacatg | cgtggtggtg | 600 |
| gacgtgagcc | acgaagaccc | tgaggtcaag | ttcaactggt | acgtggacgg | cgtggaggtg | 660 |
| cataatgcca | agacaaagcc | gcgggaggag | cagtacaaca | gcacgtaccg | tgtggtcagc | 720 |
| gtcctcaccg | tcctgcacca | ggactggctg | aatggcaagg | agtacaagtg | caaggtctcc | 780 |
| aacaaagccc | tcccagcccc | catcgagaaa | accatctcca | aagccaaagg | gcagccccga | 840 |
| gaaccacagg | tgtacaccct | gcccccatcc | cgggatgagc | tgaccaagaa | ccaggtcagc | 900 |
| ctgacctgcc | tggtcaaagg | cttctatccc | agcgacatcg | ccgtggagtg | ggagagcaat | 960 |
| gggcagccgg | agaacaacta | caagaccacg | cctcccgtgc | tggactccga | cggctccttc | 1020 |
| ttcctctaca | gcaagctcac | cgtggacaag | agcaggtggc | agcagggaa | cgtcttctca | 1080 |
| tgctccgtga | tgcatgaggc | tctgcacaac | cactacacgc | agaagagcct | ctccctgtct | 1140 |
| ccgggtaaat | ga | | | | | 1152 |

<210> SEQ ID NO 8
<211> LENGTH: 383
<212> TYPE: PRT
<213> ORGANISM: Artificial Sequence
<220> FEATURE:
<223> OTHER INFORMATION: Description of Artificial Sequence: L104EIg
      sequence

<400> SEQUENCE: 8

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro

```
                    20                  25                  30
Ala Val Val Leu Ala Ser Ser Arg Gly Ile Ala Ser Phe Val Cys Glu
            35                  40                  45
Tyr Ala Ser Pro Gly Lys Ala Thr Glu Val Arg Val Thr Val Leu Arg
        50                  55                  60
Gln Ala Asp Ser Gln Val Thr Glu Val Cys Ala Ala Thr Tyr Met Met
65                  70                  75                  80
Gly Asn Glu Leu Thr Phe Leu Asp Asp Ser Ile Cys Thr Gly Thr Ser
                85                  90                  95
Ser Gly Asn Gln Val Asn Leu Thr Ile Gln Gly Leu Arg Ala Met Asp
                100                 105                 110
Thr Gly Leu Tyr Ile Cys Lys Val Glu Leu Met Tyr Pro Pro Pro Tyr
            115                 120                 125
Tyr Glu Gly Ile Gly Asn Gly Thr Gln Ile Tyr Val Ile Asp Pro Glu
        130                 135                 140
Pro Cys Pro Asp Ser Asp Gln Glu Pro Lys Ser Ser Asp Lys Thr His
145                 150                 155                 160
Thr Ser Pro Pro Ser Pro Ala Pro Glu Leu Leu Gly Gly Ser Ser Val
                165                 170                 175
Phe Leu Phe Pro Pro Lys Pro Lys Asp Thr Leu Met Ile Ser Arg Thr
                180                 185                 190
Pro Glu Val Thr Cys Val Val Val Asp Val Ser His Glu Asp Pro Glu
            195                 200                 205
Val Lys Phe Asn Trp Tyr Val Asp Gly Val Glu Val His Asn Ala Lys
        210                 215                 220
Thr Lys Pro Arg Glu Glu Gln Tyr Asn Ser Thr Tyr Arg Val Val Ser
225                 230                 235                 240
Val Leu Thr Val Leu His Gln Asp Trp Leu Asn Gly Lys Glu Tyr Lys
                245                 250                 255
Cys Lys Val Ser Asn Lys Ala Leu Pro Ala Pro Ile Glu Lys Thr Ile
                260                 265                 270
Ser Lys Ala Lys Gly Gln Pro Arg Glu Pro Gln Val Tyr Thr Leu Pro
            275                 280                 285
Pro Ser Arg Asp Glu Leu Thr Lys Asn Gln Val Ser Leu Thr Cys Leu
        290                 295                 300
Val Lys Gly Phe Tyr Pro Ser Asp Ile Ala Val Glu Trp Glu Ser Asn
305                 310                 315                 320
Gly Gln Pro Glu Asn Asn Tyr Lys Thr Thr Pro Pro Val Leu Asp Ser
                325                 330                 335
Asp Gly Ser Phe Phe Leu Tyr Ser Lys Leu Thr Val Asp Lys Ser Arg
                340                 345                 350
Trp Gln Gln Gly Asn Val Phe Ser Cys Ser Val Met His Glu Ala Leu
            355                 360                 365
His Asn His Tyr Thr Gln Lys Ser Leu Ser Leu Ser Pro Gly Lys
        370                 375                 380

<210> SEQ ID NO 9
<211> LENGTH: 1152
<212> TYPE: DNA
<213> ORGANISM: Artificial Sequence
<220> FEATURE:
<223> OTHER INFORMATION: Description of Artificial Sequence: L104EA29LIg
      sequence

<400> SEQUENCE: 9
```

```
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aattgactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
gagctcatgt acccaccgcc atactacgag ggcataggca acggaaccca gatttatgta     420
attgatccag aaccgtgccc agattctgat caggagccca atcttctga caaaactcac     480
acatccccac cgtccccagc acctgaactc ctgggggat cgtcagtctt cctcttcccc      540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg tgtggtcagc     720
gtcctcaccg tcctgcacca ggactggctg aatggcaagg agtacaagtg caaggtctcc     780
aacaaagccc tcccagcccc catcgagaaa accatctcca agccaaagg cagccccga      840
gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
ttcctctaca gcaagctcac cgtggacaag agcaggtggc agcaggggaa cgtcttctca    1080
tgctccgtga tgcatgaggc tctgcacaac cactacacgc agaagagcct ctccctgtct    1140
ccgggtaaat ga                                                        1152
```

<210> SEQ ID NO 10
<211> LENGTH: 383
<212> TYPE: PRT
<213> ORGANISM: Artificial Sequence
<220> FEATURE:
<223> OTHER INFORMATION: Description of Artificial Sequence: L104EA29LIg
      sequence

<400> SEQUENCE: 10

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Leu Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His

```
                145                 150                 155                 160
Thr Ser Pro Pro Ser Pro Ala Pro Glu Leu Leu Gly Gly Ser Ser Val
                    165                 170                 175
Phe Leu Phe Pro Pro Lys Pro Lys Asp Thr Leu Met Ile Ser Arg Thr
                180                 185                 190
Pro Glu Val Thr Cys Val Val Val Asp Val Ser His Glu Asp Pro Glu
            195                 200                 205
Val Lys Phe Asn Trp Tyr Val Asp Gly Val Glu Val His Asn Ala Lys
        210                 215                 220
Thr Lys Pro Arg Glu Glu Gln Tyr Asn Ser Thr Tyr Arg Val Val Ser
225                 230                 235                 240
Val Leu Thr Val Leu His Gln Asp Trp Leu Asn Gly Lys Glu Tyr Lys
                245                 250                 255
Cys Lys Val Ser Asn Lys Ala Leu Pro Ala Pro Ile Glu Lys Thr Ile
            260                 265                 270
Ser Lys Ala Lys Gly Gln Pro Arg Glu Pro Gln Val Tyr Thr Leu Pro
        275                 280                 285
Pro Ser Arg Asp Glu Leu Thr Lys Asn Gln Val Ser Leu Thr Cys Leu
290                 295                 300
Val Lys Gly Phe Tyr Pro Ser Asp Ile Ala Val Glu Trp Glu Ser Asn
305                 310                 315                 320
Gly Gln Pro Glu Asn Asn Tyr Lys Thr Thr Pro Pro Val Leu Asp Ser
                325                 330                 335
Asp Gly Ser Phe Phe Leu Tyr Ser Lys Leu Thr Val Asp Lys Ser Arg
            340                 345                 350
Trp Gln Gln Gly Asn Val Phe Ser Cys Ser Val Met His Glu Ala Leu
        355                 360                 365
His Asn His Tyr Thr Gln Lys Ser Leu Ser Leu Ser Pro Gly Lys
    370                 375                 380

<210> SEQ ID NO 11
<211> LENGTH: 1152
<212> TYPE: DNA
<213> ORGANISM: Artificial Sequence
<220> FEATURE:
<223> OTHER INFORMATION: Description of Artificial Sequence: L104EA29YIg
     sequence

<400> SEQUENCE: 11
atgggtgtac tgctcacaca gaggacgctg ctcagtctgg tccttgcact cctgtttcca     60
agcatggcga gcatggcaat gcacgtggcc cagcctgctg tggtactggc cagcagccga    120
ggcatcgcta gctttgtgtg tgagtatgca tctccaggca aaactactga ggtccgggtg    180
acagtgcttc ggcaggctga cagccaggtg actgaagtct gtgcggcaac ctacatgatg    240
gggaatgagt tgaccttcct agatgattcc atctgcacgg gcacctccag tggaaatcaa    300
gtgaacctca ctatccaagg actgagggcc atggacacgg gactctacat ctgcaaggtg    360
gagctcatgt acccaccgcc atactacgag ggcataggca acggaaccca gatttatgta    420
attgatccag aaccgtgccc agattctgat caggagccca atcttctga caaaactcac    480 acatccccac cgtccccagc acctgaactc ctggggggat cgtcagtctt cctcttcccc    540
ccaaaaccca aggacaccct catgatctcc cggacccctg aggtcacatg cgtggtggtg    600
gacgtgagcc acgaagaccc tgaggtcaag ttcaactggt acgtggacgg cgtggaggtg    660
cataatgcca agacaaagcc gcgggaggag cagtacaaca gcacgtaccg tgtggtcagc    720
```

```
gtcctcaccg tcctgcacca ggactggctg aatggcaagg agtacaagtg caaggtctcc    780
aacaaagccc tcccagcccc catcgagaaa accatctcca agccaaagg gcagccccga      840 gaaccacagg tgtacaccct gccccatcc cgggatgagc tgaccaagaa ccaggtcagc     900
ctgacctgcc tggtcaaagg cttctatccc agcgacatcg ccgtggagtg ggagagcaat    960
gggcagccgg agaacaacta caagaccacg cctcccgtgc tggactccga cggctccttc   1020
ttcctctaca gcaagctcac cgtggacaag agcaggtggc agcaggggaa cgtcttctca   1080
tgctccgtga tgcatgaggc tctgcacaac cactacacgc agaagagcct ctccctgtct   1140
ccgggtaaat ga                                                       1152
```

<210> SEQ ID NO 12
<211> LENGTH: 383
<212> TYPE: PRT
<213> ORGANISM: Artificial Sequence
<220> FEATURE:
<223> OTHER INFORMATION: Description of Artificial Sequence: L104EA29TIg
      sequence

<400> SEQUENCE: 12

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Thr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
```

-continued

```
                275                 280                 285
Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
                340                 345                 350

Trp Gln Gln Gly Asn Val Phe Ser Cys Ser Val Met His Glu Ala Leu
            355                 360                 365

His Asn His Tyr Thr Gln Lys Ser Leu Ser Leu Ser Pro Gly Lys
    370                 375                 380
```

<210> SEQ ID NO 13
<211> LENGTH: 1152
<212> TYPE: DNA
<213> ORGANISM: Artificial Sequence
<220> FEATURE:
<223> OTHER INFORMATION: Description of Artificial Sequence: L104EA29WIg
      sequence

<400> SEQUENCE: 13

```
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca atggactga ggtccgggtg      180 acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg actctacat ctgcaaggtg      360 gagctcatgt acccaccgcc atactacgag ggcataggca acggaaccca gatttatgta     420
attgatccag aaccgtgccc agattctgat caggagccca atcttctga caaaactcac      480 acatccccac cgtccccagc acctgaactc ctggggggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg tgtggtcagc     720
gtcctcaccg tcctgcacca ggactggctg aatggcaagg agtacaagtg caaggtctcc     780
aacaaagccc tcccagcccc catcgagaaa accatctcca aagccaaagg gcagccccga     840
gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
ttcctctaca gcaagctcac cgtggacaag agcaggtggc agcaggggaa cgtcttctca    1080
tgctccgtga tgcatgaggc tctgcacaac cactacacgc agaagagcct ctccctgtct    1140
ccgggtaaat ga                                                        1152
```

<210> SEQ ID NO 14
<211> LENGTH: 383
<212> TYPE: PRT
<213> ORGANISM: Artificial Sequence
<220> FEATURE:
<223> OTHER INFORMATION: Description of Artificial Sequence: L104EA29WIg
      sequence

<400> SEQUENCE: 14

```
Met Gly Val Leu Leu Thr Gln Arg Thr Leu Leu Ser Leu Val Leu Ala
 1               5                  10                  15

Leu Leu Phe Pro Ser Met Ala Ser Met Ala Met His Val Ala Gln Pro
             20                  25                  30

Ala Val Val Leu Ala Ser Ser Arg Gly Ile Ala Ser Phe Val Cys Glu
         35                  40                  45

Tyr Ala Ser Pro Gly Lys Trp Thr Glu Val Arg Val Thr Val Leu Arg
 50                  55                  60

Gln Ala Asp Ser Gln Val Thr Glu Val Cys Ala Ala Thr Tyr Met Met
 65                  70                  75                  80

Gly Asn Glu Leu Thr Phe Leu Asp Asp Ser Ile Cys Thr Gly Thr Ser
                 85                  90                  95

Ser Gly Asn Gln Val Asn Leu Thr Ile Gln Gly Leu Arg Ala Met Asp
             100                 105                 110

Thr Gly Leu Tyr Ile Cys Lys Val Glu Leu Met Tyr Pro Pro Pro Tyr
         115                 120                 125

Tyr Glu Gly Ile Gly Asn Gly Thr Gln Ile Tyr Val Ile Asp Pro Glu
130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                 165                 170                 175

Phe Leu Phe Pro Pro Lys Pro Lys Asp Thr Leu Met Ile Ser Arg Thr
             180                 185                 190

Pro Glu Val Thr Cys Val Val Asp Val Ser His Glu Asp Pro Glu
         195                 200                 205

Val Lys Phe Asn Trp Tyr Val Asp Gly Val Glu Val His Asn Ala Lys
210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                 245                 250                 255

Cys Lys Val Ser Asn Lys Ala Leu Pro Ala Pro Ile Glu Lys Thr Ile
             260                 265                 270

Ser Lys Ala Lys Gly Gln Pro Arg Glu Pro Gln Val Tyr Thr Leu Pro
         275                 280                 285

Pro Ser Arg Asp Glu Leu Thr Lys Asn Gln Val Ser Leu Thr Cys Leu
290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                 325                 330                 335

Asp Gly Ser Phe Phe Leu Tyr Ser Lys Leu Thr Val Asp Lys Ser Arg
             340                 345                 350

Trp Gln Gln Gly Asn Val Phe Ser Cys Ser Val Met His Glu Ala Leu
         355                 360                 365

His Asn His Tyr Thr Gln Lys Ser Leu Ser Leu Ser Pro Gly Lys
370                 375                 380

<210> SEQ ID NO 15
<211> LENGTH: 1152
<212> TYPE: DNA
```

<210> SEQ ID NO 15
<211> LENGTH: 1152
<212> TYPE: DNA
<213> ORGANISM: Artificial Sequence
<220> FEATURE:
<223> OTHER INFORMATION: Description of Artificial Sequence: CTLA4Ig
    sequence

<400> SEQUENCE: 15

| | |
|---|---|
| atgggtgtac tgctcacaca gaggacgctg ctcagtctgg tccttgcact cctgtttcca | 60 |
| agcatggcga gcatggcaat gcacgtggcc cagcctgctg tggtactggc agcagccga | 120 |
| ggcatcgcca gctttgtgtg tgagtatgca tctccaggca aagccactga ggtccgggtg | 180 |
| acagtgcttc ggcaggctga cagccaggtg actgaagtct gtgcggcaac ctacatgatg | 240 |
| gggaatgagt tgaccttcct agatgattcc atctgcacgg gcacctccag tggaaatcaa | 300 |
| gtgaacctca ctatccaagg actgagggca atggacacgg gactctacat ctgcaaggtg | 360 |
| gagctcatgt acccaccgcc atactacctg gcataggca acggaaccca gatttatgta | 420 |
| attgatccag aaccgtgccc agattctgat caggagccca atcttctga caaaactcac | 480 |
| acatccccac cgtcccagc acctgaactc ctggggggat cgtcagtctt cctcttcccc | 540 |
| ccaaaaccca aggacaccct catgatctcc cggaccctg aggtcacatg cgtggtggtg | 600 |
| gacgtgagcc acgaagaccc tgaggtcaag ttcaactggt acgtggacgg cgtggaggtg | 660 |
| cataatgcca agacaaagcc gcgggaggag cagtacaaca gcacgtaccg tgtggtcagc | 720 |
| gtcctcaccg tcctgcacca ggactggctg aatggcaagg agtacaagtg caaggtctcc | 780 |
| aacaaagccc tcccagcccc catcgagaaa accatctcca agccaaaagg cagccccga | 840 |
| gaaccacagg tgtacaccct gcccccatcc cgggatgagc tgaccaagaa ccaggtcagc | 900 |
| ctgacctgcc tggtcaaagg cttctatccc agcgacatcg ccgtggagtg ggagagcaat | 960 |
| gggcagccgg agaacaacta caagaccacg cctcccgtgc tggactccga cggctccttc | 1020 |
| ttcctctaca gcaagctcac cgtggacaag agcaggtggc agcagggaa cgtcttctca | 1080 |
| tgctccgtga tgcatgaggc tctgcacaac cactacacgc agaagagcct ctccctgtct | 1140 |
| ccgggtaaat ga | 1152 |

<210> SEQ ID NO 16
<211> LENGTH: 383
<212> TYPE: PRT
<213> ORGANISM: Artificial Sequence
<220> FEATURE:
<223> OTHER INFORMATION: Description of Artificial Sequence: CTLA4Ig
    sequence

<400> SEQUENCE: 16

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110
```

```
Thr Gly Leu Tyr Ile Cys Lys Val Glu Leu Met Tyr Pro Pro Pro Tyr
            115                 120                 125

Tyr Leu Gly Ile Gly Asn Gly Thr Gln Ile Tyr Val Ile Asp Pro Glu
        130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
            195                 200                 205

Val Lys Phe Asn Trp Tyr Val Asp Gly Val Glu Val His Asn Ala Lys
210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
            245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
            325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Oncostatin
      M CTLA4 (OMCTLA4) forward primer

<400> SEQUENCE: 17
gaggtgataa agcttcacca atgggtgtac tgctcacaca g                        41

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Oncostatin
      M CTLA4 (OMCTLA4) reverse primer

<400> SEQUENCE: 18
gtggtgtatt ggtctagatc aatcagaatc tgggcacggt tc                       42
```